United States Patent [19]

Takiguchi et al.

[11] Patent Number: 5,190,690
[45] Date of Patent: Mar. 2, 1993

[54] MESOMORPHIC COMPOUND, LIQUID CRYSTAL COMPOSITION CONTAINING SAME AND LIQUID CRYSTAL DEVICE USING SAME

[75] Inventors: Takao Takiguchi, Tokyo; Takashi Iwaki, Isehara; Takeshi Togano, Yokohama; Yoko Yamada; Shosei Mori, both of Atsugi, all of Japan

[73] Assignee: Canon Kabushiki Kaisha, Tokyo, Japan

[21] Appl. No.: 511,314

[22] Filed: Apr. 19, 1990

[30] Foreign Application Priority Data

Apr. 20, 1989 [JP] Japan .................. 1-102238

[51] Int. Cl.$^5$ .................. C09K 19/34; G02F 1/13
[52] U.S. Cl. .................. 252/299.61; 359/103
[58] Field of Search .................. 252/299.01, 299.61,
252/299.62, 299.63, 299.64, 299.65, 299.66;
430/76, 270; 528/179, 183; 548/122, 123, 124,
125, 217, 218, 219, 220; 350/350 R, 350 S,
96.34; 544/242, 245; 546/26; 560/116; 549/64

[56] References Cited

U.S. PATENT DOCUMENTS

| | | | |
|---|---|---|---|
| 3,268,543 | 8/1966 | Siegrist et al. | 548/217 |
| 3,336,192 | 8/1967 | Sarett et al. | 514/365 |
| 3,644,345 | 2/1972 | Siegrist et al. | 548/217 |
| 3,725,395 | 4/1973 | Siegrist et al. | 548/217 |
| 4,367,924 | 1/1983 | Clark et al. | 359/56 |
| 4,775,215 | 10/1988 | Teng et al. | 350/96.34 |
| 4,904,410 | 2/1990 | Nohira et al. | 252/299.61 |
| 4,918,213 | 4/1990 | Nohira et al. | 558/271 |

FOREIGN PATENT DOCUMENTS

| | | |
|---|---|---|
| 403486 | 3/1967 | Australia . |
| 478933 | 11/1974 | Australia . |
| 486942 | 4/1976 | Australia . |
| 107216 | 8/1981 | Japan . |
| 193426 | 11/1984 | Japan . |
| 193427 | 11/1984 | Japan . |
| 156047 | 8/1985 | Japan . |
| 245142 | 10/1986 | Japan . |
| 246722 | 10/1986 | Japan . |
| 246723 | 10/1986 | Japan . |
| 246724 | 10/1986 | Japan . |
| 249024 | 11/1986 | Japan . |
| 249025 | 11/1986 | Japan . |
| 542212 | 11/1973 | Switzerland . |

OTHER PUBLICATIONS

CA: 93:186223y, "Synthesis of Heterocyclic Liquid Crystals and Its Significance in Gas Chromatography", Tai et al., Tzu Jan Tsa Chih, (Peking Ind. Univ., Peking, Peop., R. China), 88, 89, 1980.

Primary Examiner—Robert L. Stoll
Assistant Examiner—Shean C. Wu
Attorney, Agent, or Firm—Fitzpatrick, Cella, Harper & Scinto

[57] ABSTRACT

A mesomorphic compound represented by the following formula (I):

$$R_1—X_1—A_1—\bigodot—A_2—X_2—R_2 \quad (I)$$

wherein $R_1$ and $R_2$ respectively denote an alkyl group having 1-16 carbon atoms capable of having a substituent; $X_1$ and $X_2$ respectively denote a single bond, $$—O—, \quad —OC—, \quad —CO—, \quad —OCO— \quad \text{or} \quad —C—;$$
$$\quad\quad\quad \| \quad\quad \| \quad\quad\quad \| \quad\quad\quad\quad \|$$
$$\quad\quad\quad O \quad\quad O \quad\quad\quad O \quad\quad\quad\quad O$$

and $A_1$ and $A_2$ respectively denote (structures shown)

wherein $X_3$ and $X_4$ respectively denote hydrogen, fluorine, chlorine, bromine, $—CH_3$, $—CN$ or $—CF_3$; and $Z$ denotes $—O—$ or $—S—$.

306 Claims, 2 Drawing Sheets

OTHER PUBLICATIONS

Appl. Phys. Lett., vol. 18, No. 4, (Feb. 1971).
Die Praxis des Organischen Chemikers, (1925), 212:217.
Journal of the American Chemical Society, vol. 63, (1941), 196.
Journal of the American Chemical Society, vol. 79, (1957), 427.
Chemical and Pharmaceutical Bulletin, vol. 18, No. 3, (Mar. 1970), 578:590.
Helvetica Chimica Acta, vol. 57, Nos. 7–8, (1974), 81.

MESOMORPHIC COMPOUND, LIQUID CRYSTAL COMPOSITION CONTAINING SAME AND LIQUID CRYSTAL DEVICE USING SAME

FIELD OF THE INVENTION AND RELATED ART

The present invention relates to a novel mesomorphic compound, a liquid crystal composition containing the compound and liquid crystal device using the composition, and more particularly to a novel liquid crystal composition with improved responsiveness to an electric field and a liquid crystal device using the liquid crystal composition for use in a liquid crystal display apparatus, a liquid crystal-optical shutter, etc.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127-128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of milli-seconds, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected or regions where a scanning electrode is not selected and a signal electrode is selected (which regions are so called "half-selected points"). If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. As a result, this leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and are vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. has been already proposed. However, any method is not sufficient to overcome the above-mentioned drawbacks. As a result, it is the present state that the development of large image area or high packaging density with respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216, U.S. Pat. No. 4,367,924, etc.). In this instance, as the liquid crystals having bistability, ferroelectric liquid crystals having chiral smectic C-phase (SmC*) or H-phase (SmH*) are generally used. These liquid crystals have bistable states of first and second optically stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric field and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, ferroelectric liquid crystal materials developed heretofore cannot be said to satisfy sufficient characteristics required for a liquid crystal device including low-temperature operation characteristic, high-speed responsiveness, etc. Among a response time $\tau$, the magnitude of spontaneous polarization Ps and viscosity $\eta$, the following relationship exists: $\tau = \eta/(Ps \cdot E)$, where E is an applied voltage. Accordingly, a high response speed can be obtained by (a) increasing the spontaneous polarization Ps, (b) lowering the viscosity $\eta$, or (c) increasing the applied voltage E. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Further, if it is assumed that the operation temperature of an actual display device is 5°–40° C., the response speed changes by a factor of about 20, so that it actually exceeds the range controllable by driving voltage and frequency.

As described hereinabove, commercialization of a ferroelectric liquid crystal device requires a ferroelectric chiral smectic liquid crystal composition having a low viscosity, a high-speed responsiveness and a small temperature-dependence of response speed.

SUMMARY OF THE INVENTION

An object of the present invention is to provide a mesomorphic compound, a liquid crystal composition, particularly a ferroelectric chiral smectic liquid crystal composition, containing the mesomorphic compound for providing a practical ferroelectric liquid crystal device, and a liquid crystal device using the liquid crystal composition and having a high response speed and a smaller temperature-dependence of the response speed.

According to the present invention, there is provided a mesomorphic compound represented by the following formula (I):

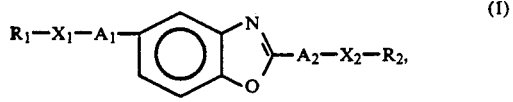

(I)

wherein $R_1$ and $R_2$ respectively denote an alkyl group having 1–16 carbon atoms capable of having a substituent; $X_1$ and $X_2$ respectively denote a single bond,

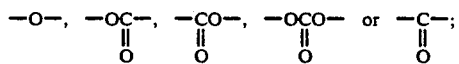

and $A_1$ and $A_2$ respectively denote

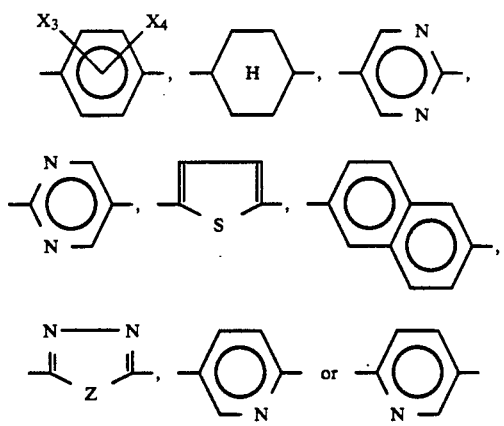

wherein $X_3$ and $X_4$ respectively denote hydrogen, fluorine, chlorine, bromine, $-CH_3$, $-CN$ or $-CF_3$; and Z denotes $-O-$ or $-S-$.

According to the present invention, there is further provided a ferroelectric chiral smectic liquid crystal composition containing at least one species of the mesomorphic compound as described above.

The present invention further provides a liquid crystal device comprising a pair of substrates and such a ferroelectric liquid crystal composition as described above disposed between the electrode plates.

These and other objects, features and advantages of the present invention will become more apparent upon a consideration of the following description of the preferred embodiments of the present invention taken in conjunction with the accompanying drawings.

DETAILED DESCRIPTION OF THE INVENTION

Figure 1:
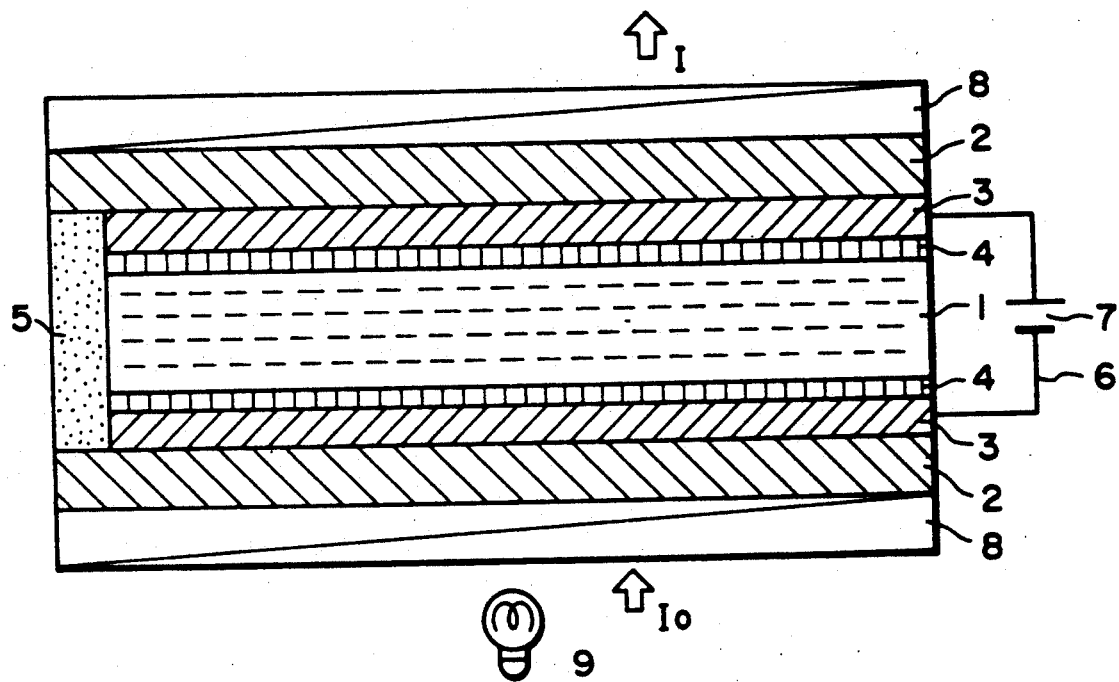
FIG. 1 is a schematic sectional view of a liquid crystal display device using a ferroelectric liquid crystal.

The mesomorphic compounds represented by the general formula (I) may generally be synthesized through the following reaction schemes.

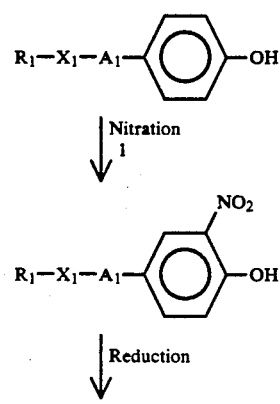

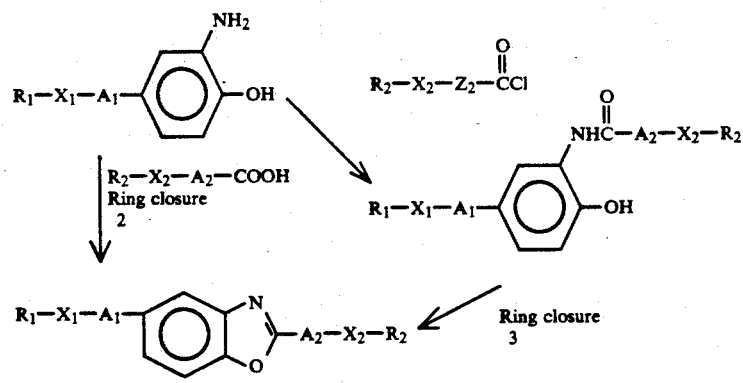

Nitration ① of phenols can be conducted by using methods shown in L. Gattermann, "Die Praxis des Organischen Chemikers", pp. 214, R. Adams et al. "J. Am. Chem. Soc.", 63, 196 (1941), etc. Ring closure ② and ③ wherein o-aminophenols change into compounds having benzoxazole rings can be conducted by using methods shown in D. W. Hein et al., "J. Am. Chem. Soc.", 79, 427 (1957), Y. Kanaoka et al. "Chem. Pharm. Bull.", 18, 587 (1970), etc. In a case wherein $X_1$ and $X_2$ are respectively

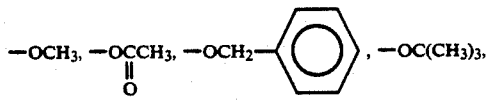

it is also possible to form a group of $R_1-X_1-A_1-$ or $R_2-X_2-A_2-$ through the following steps (a) to (c):
 (a) Hydroxyl group or carboxyl group combined with $A_1$ or $A_2$ is modified with addition of a protective group into a non-reactive or less reactive group such as

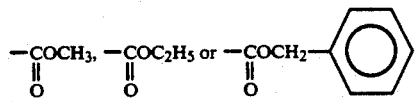

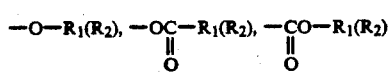

capable of elimination reaction.
 (b) Ring closure ② or ③ is effected.
 (c) The protective group is eliminated and modified into

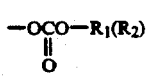

or

to form the $R_1-X_1-A_1-$ or $R_2-X_2-A_2-$ structure.

In the formula (I) as described above, preferred examples of $X_1$ and $X_2$ may respectively include the following combinations:
 $X_1$ is a single bond,

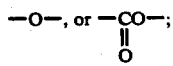

and $X_2$ is a single bond,

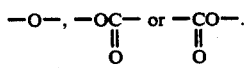

Further, preferred examples of $R_1$ and $R_2$ in the formula (I) may include the following groups (i) to (iv):
(i) n-alkyl group having 1-16 carbon atoms, particularly having 3-12 carbon atoms;

(ii)

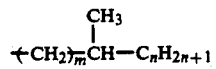

wherein m is 1-6 and n is 2-8 (optically active or inactive);

(iii)

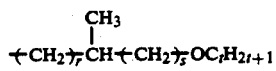

wherein r is 0-6, s is 0 or 1 and t is 1-12) optically active or inactive; and (iv)

$$-CH_2\overset{*}{C}HC_xH_{2x+1}$$
$$\phantom{-CH_2}|\phantom{HC_xH_{2x+1}}$$
$$\phantom{-CH_2C}F$$

wherein x is 1-14. Herein * denotes an optically active center.

Specific examples of the mesomorphic compounds represented by the above-mentioned general formula (I) may include those shown by the following structural formulas.

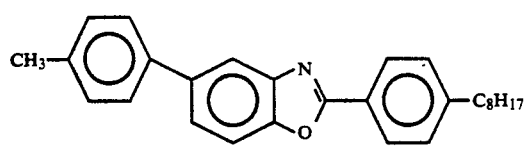 (1-1)
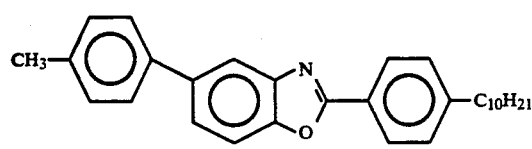 (1-2)
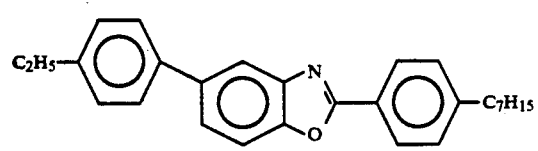 (1-3)
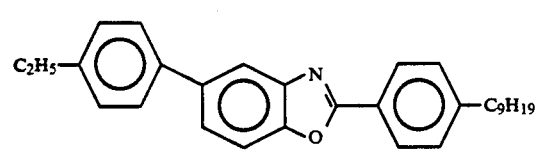 (1-4)
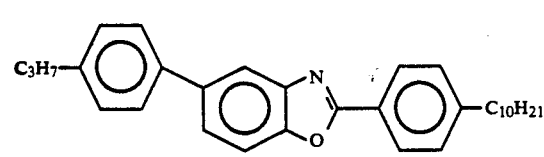 (1-5)
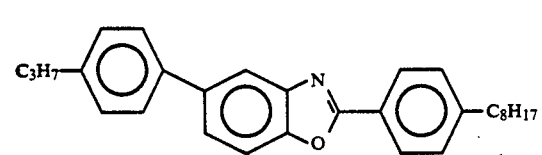 (1-6)
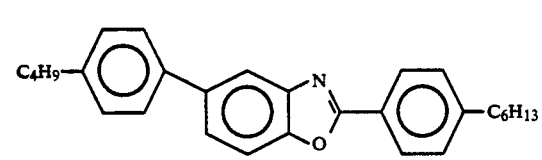 (1-7)
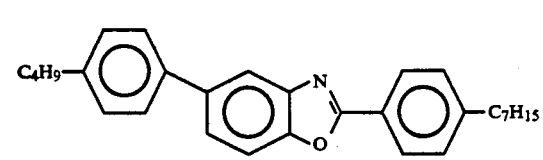 (1-8)
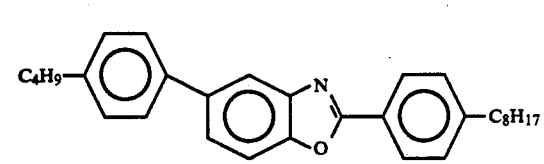 (1-9)
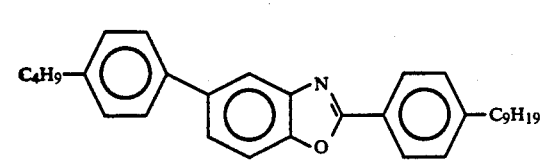 (1-10)

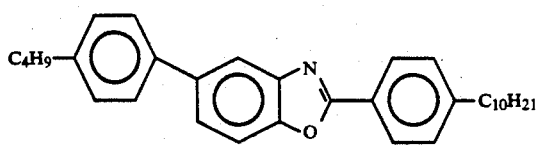
(1-11)
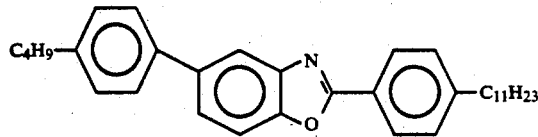
(1-12)
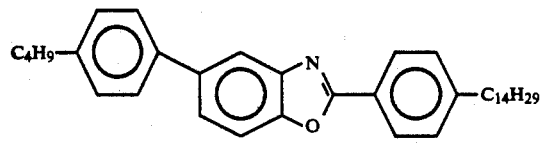
(1-13)
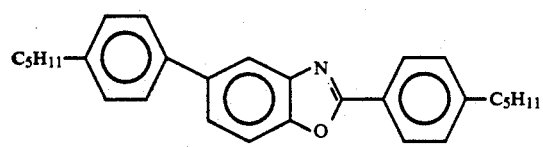
(1-14)
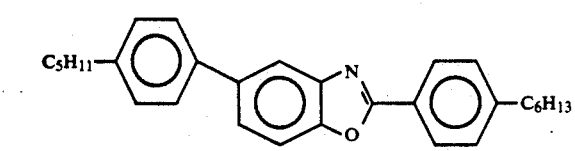
(1-15)
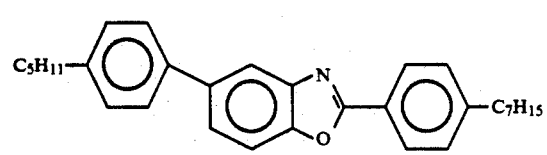
(1-16)
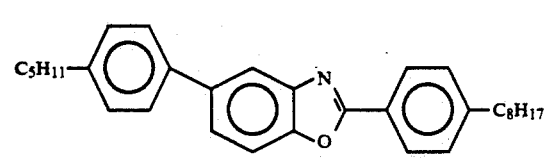
(1-17)
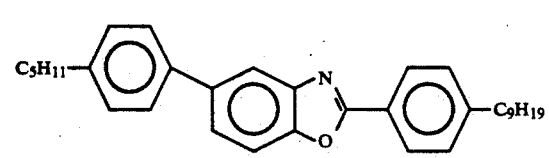
(1-18)
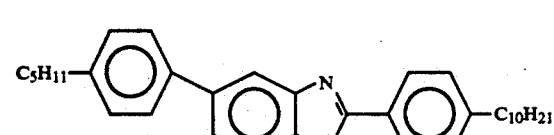
(1-19)
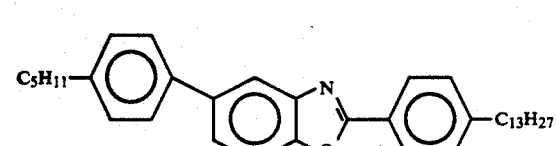
(1-20)

-continued
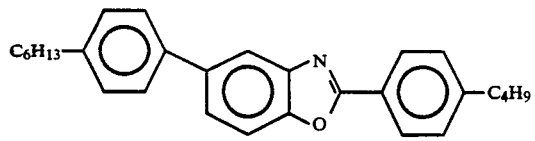 (1-21)
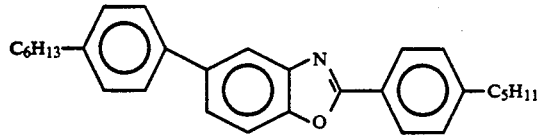 (1-22)
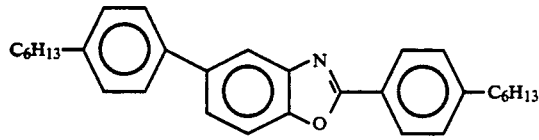 (1-23)
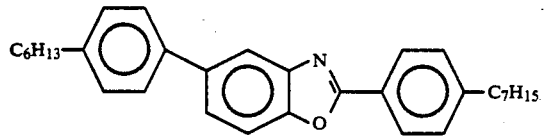 (1-24)
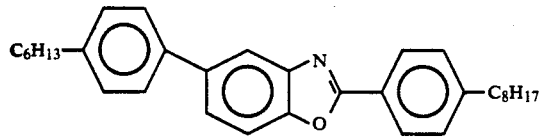 (1-25)
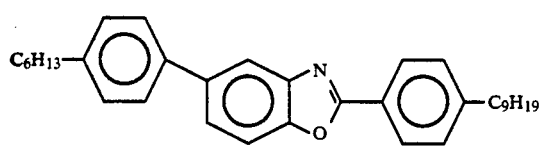 (1-26)
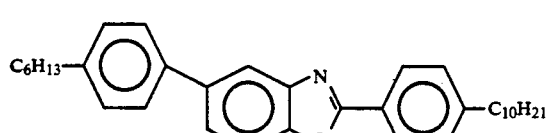 (1-27)
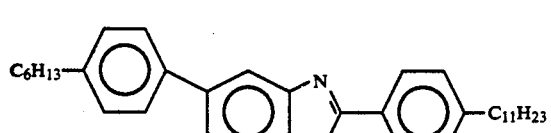 (1-28)
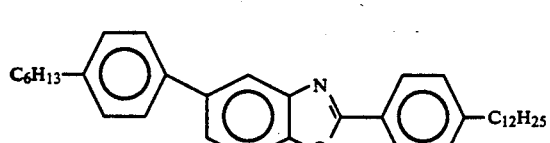 (1-29)
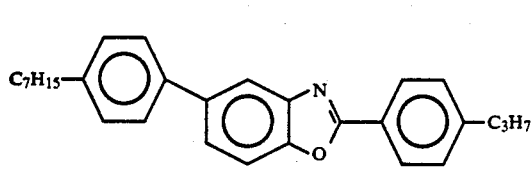 (1-30)

-continued
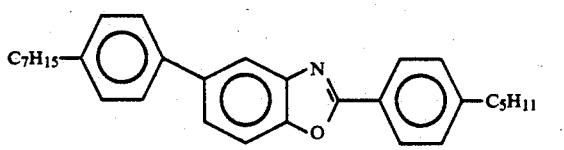 (1-31)
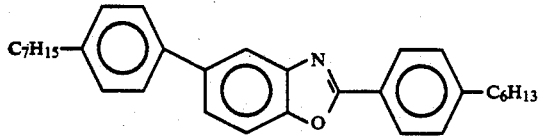 (1-32)
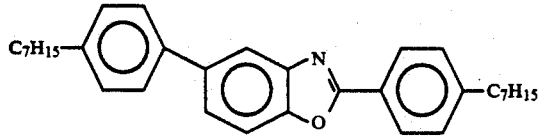 (1-33)
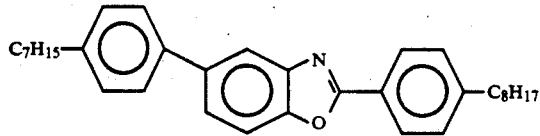 (1-34)
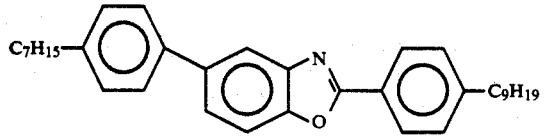 (1-35)
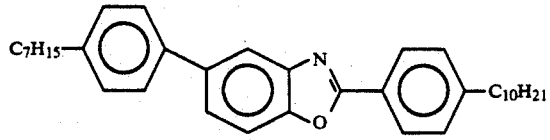 (1-36)
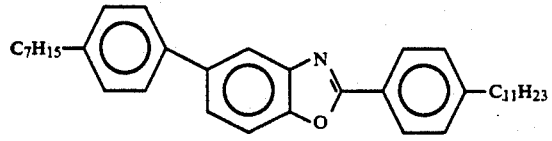 (1-37)
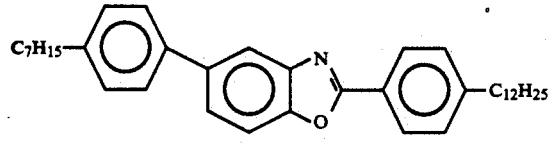 (1-38)
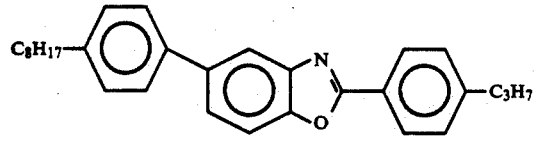 (1-39)
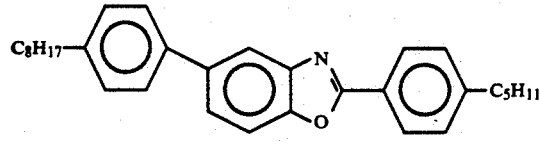 (1-40)

-continued
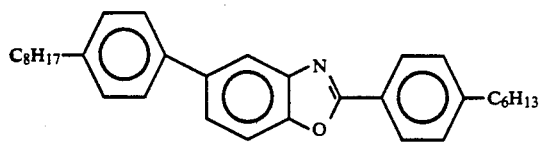
(1-41)
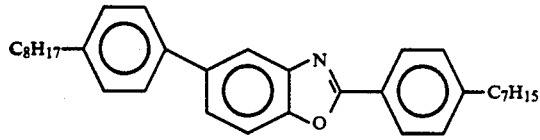
(1-42)
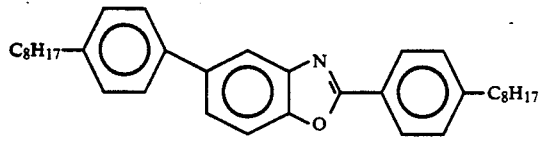
(1-43)
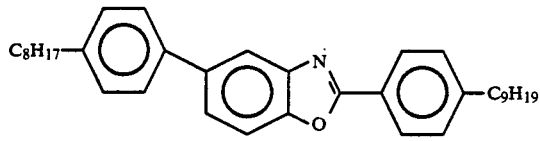
(1-44)
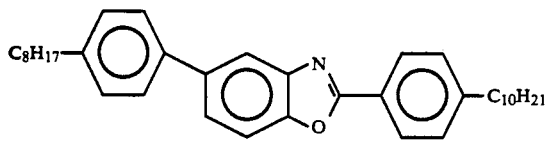
(1-45)
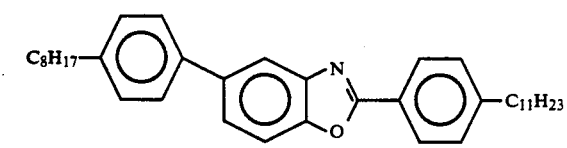
(1-46)
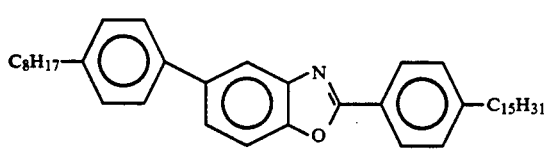
(1-47)
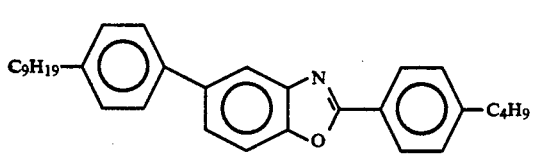
(1-48)
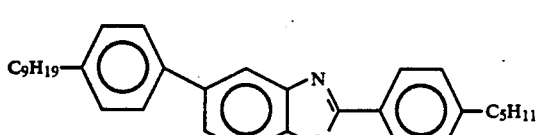
(1-49)
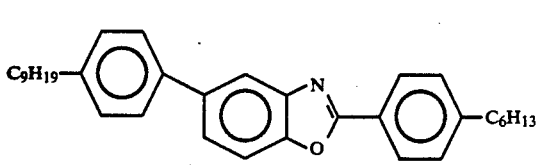
(1-50)

-continued
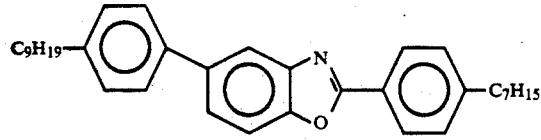
(1-51)
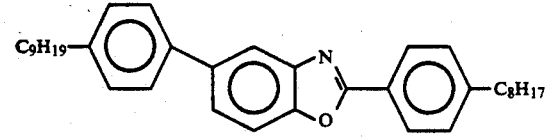
(1-52)
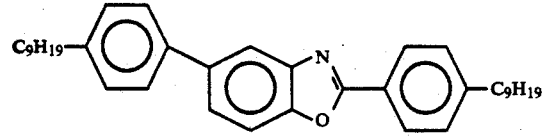
(1-53)
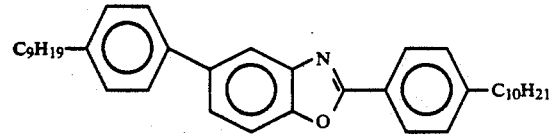
(1-54)
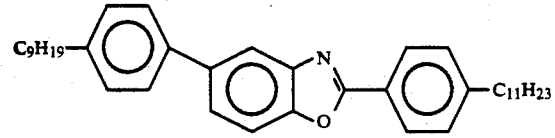
(1-55)
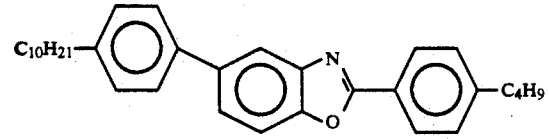
(1-56)
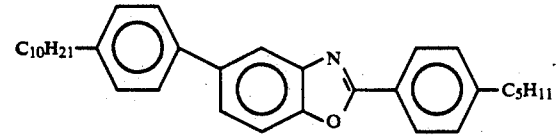
(1-57)
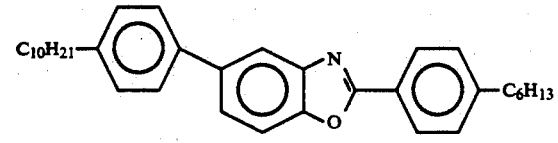
(1-58)
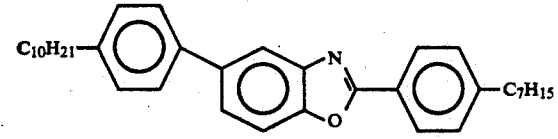
(1-59)
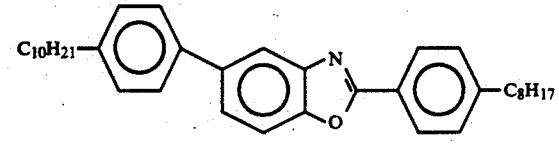
(1-60)

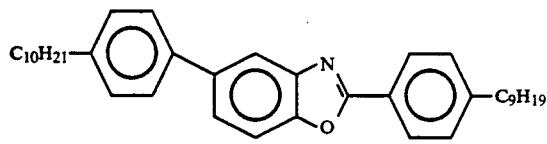 (1-61)
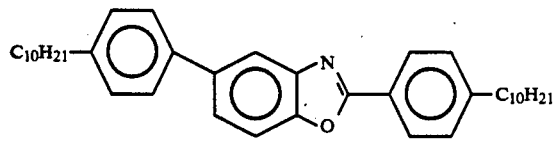 (1-62)
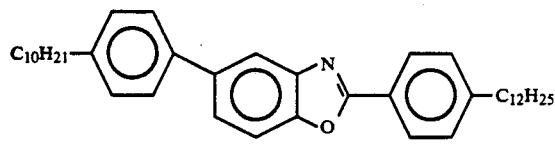 (1-63)
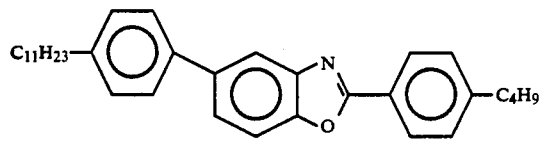 (1-64)
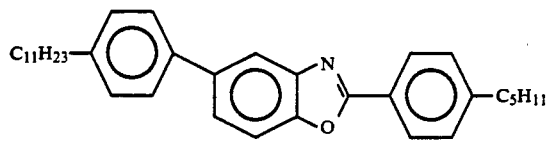 (1-65)
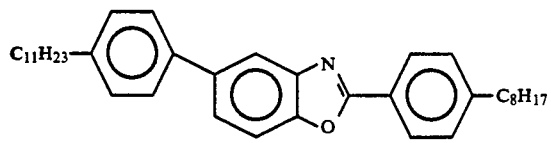 (1-66)
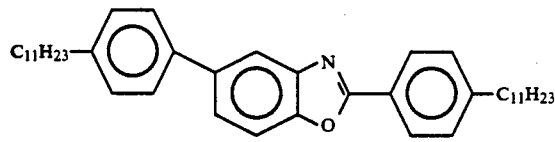 (1-67)
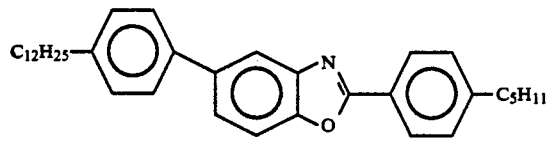 (1-68)
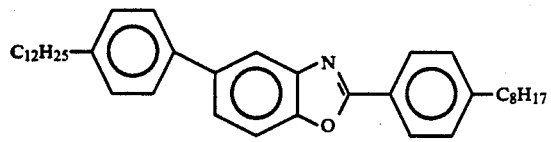 (1-69)
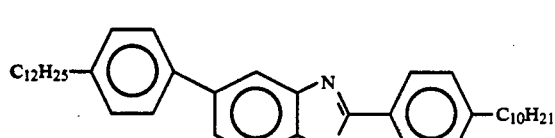 (1-70)

-continued
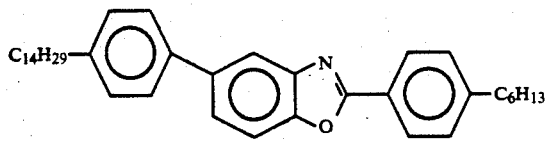 (1-71)
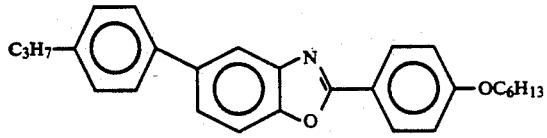 (1-72)
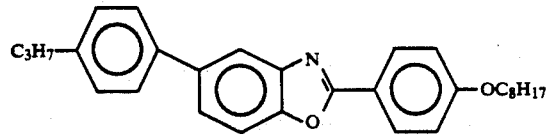 (1-73)
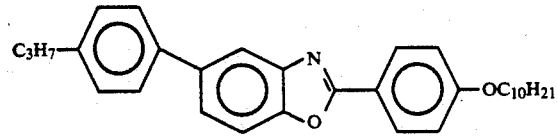 (1-74)
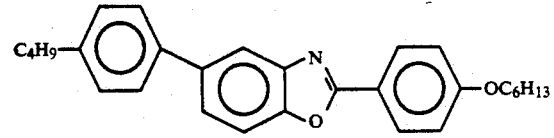 (1-75)
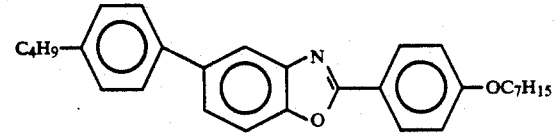 (1-76)
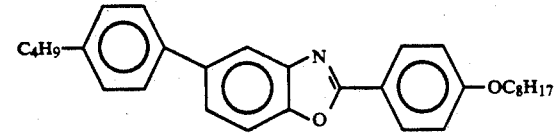 (1-77)
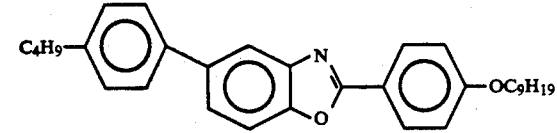 (1-78)
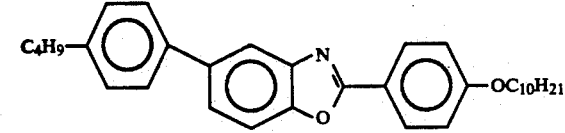 (1-79)
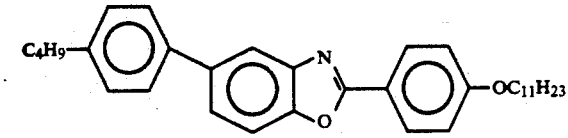 (1-80)

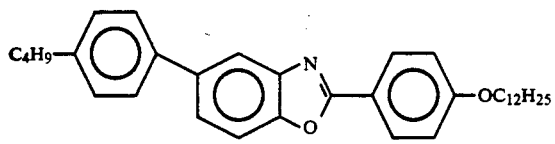
(1-81)
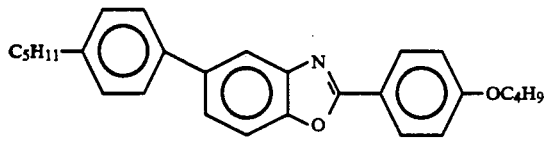
(1-82)
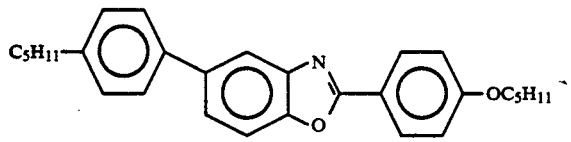
(1-83)
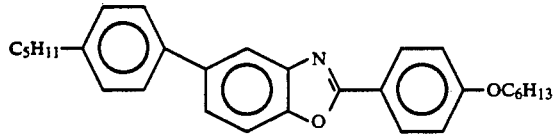
(1-84)
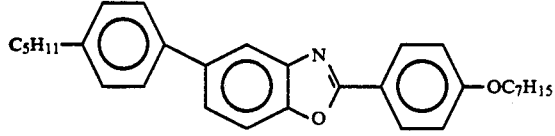
(1-85)
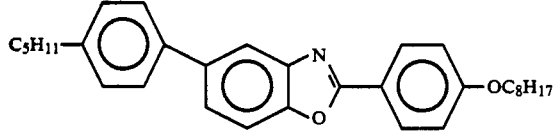
(1-86)
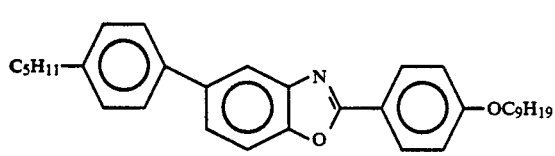
(1-87)
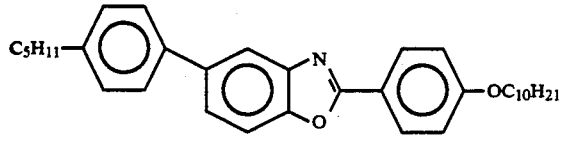
(1-88)
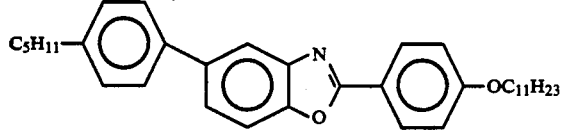
(1-89)
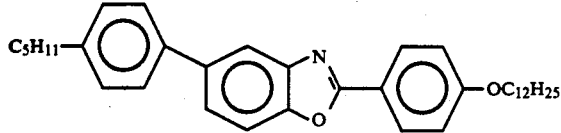
(1-90)

-continued
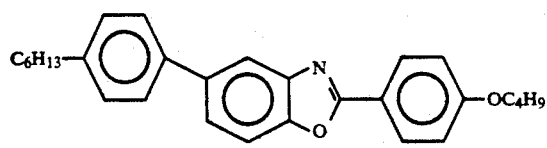 (1-91)
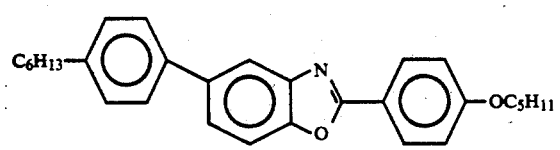 (1-92)
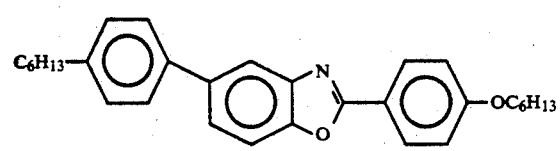 (1-93)
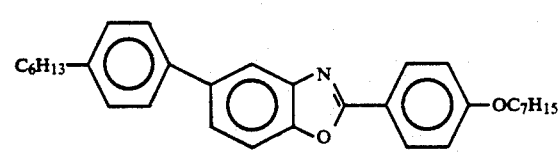 (1-94)
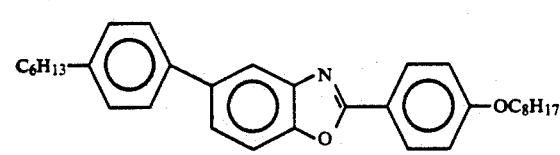 (1-95)
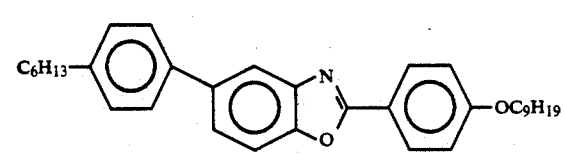 (1-96)
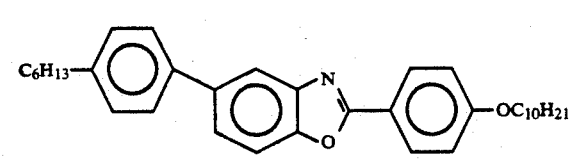 (1-97)
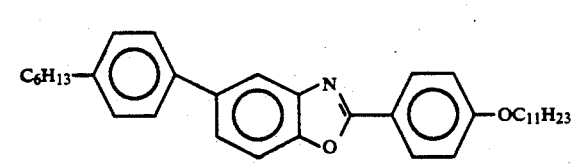 (1-98)
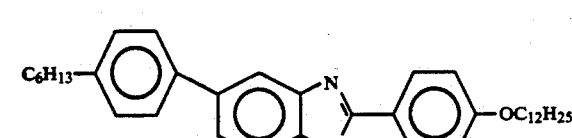 (1-99)
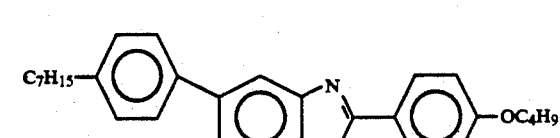 (1-100)

-continued
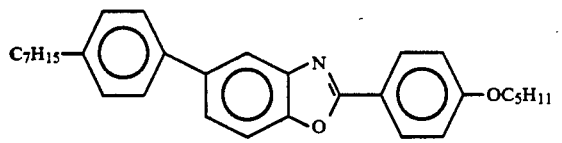 (1-101)
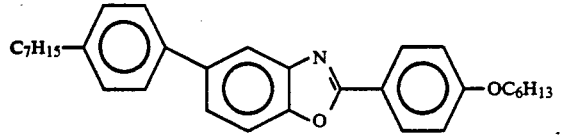 (1-102)
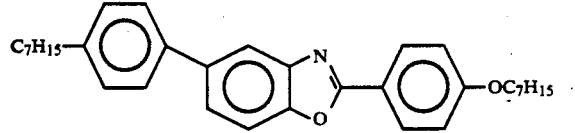 (1-103)
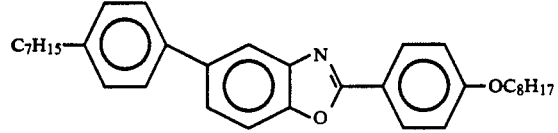 (1-104)
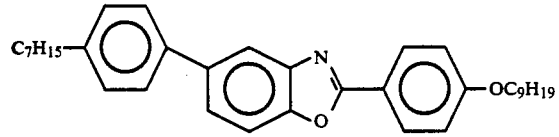 (1-105)
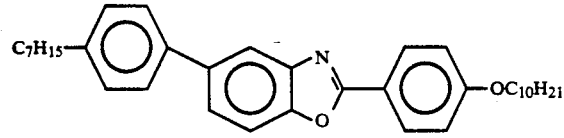 (1-106)
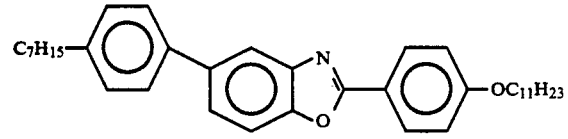 (1-107)
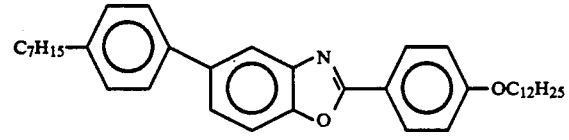 (1-108)
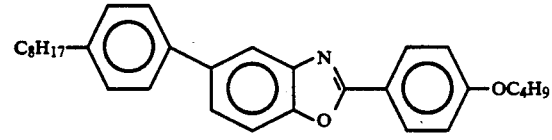 (1-109)
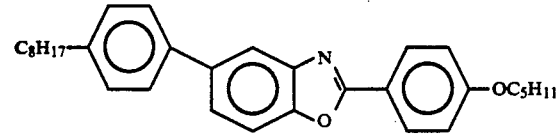 (1-110)

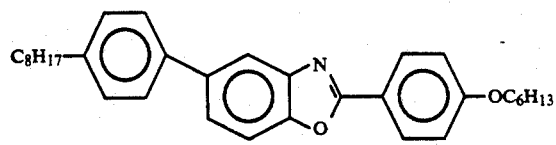 (1-111)
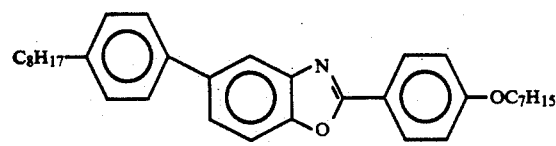 (1-112)
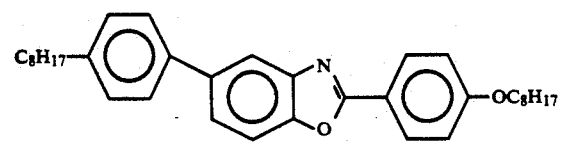 (1-113)
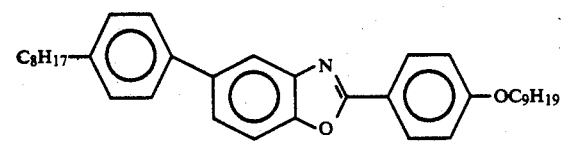 (1-114)
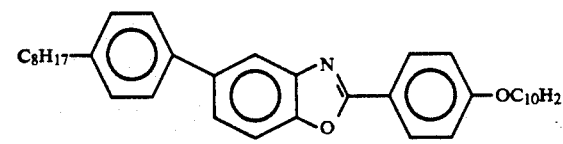 (1-115)
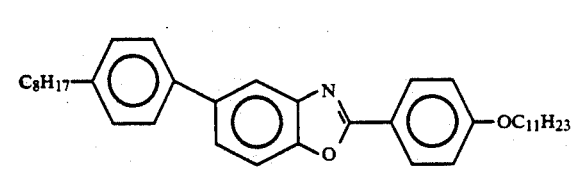 (1-116)
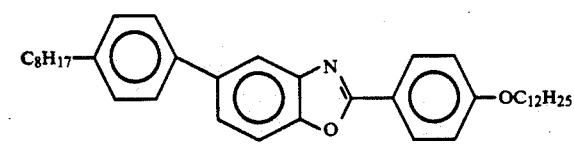 (1-117)
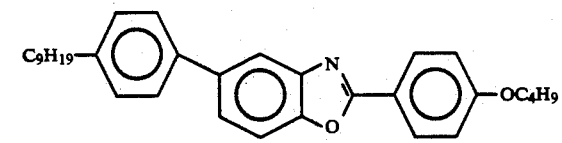 (1-118)
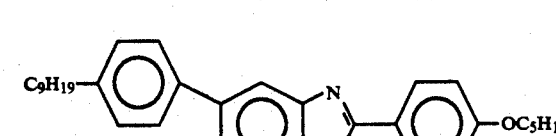 (1-119)
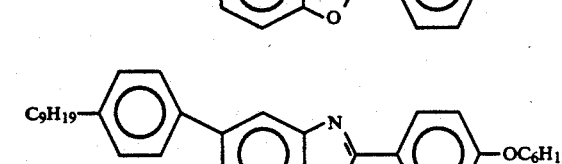 (1-120)

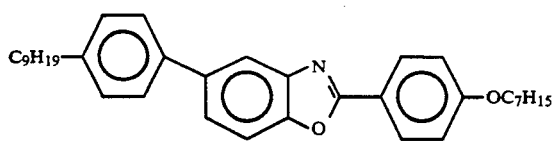
(1-121)
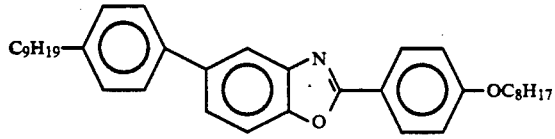
(1-122)
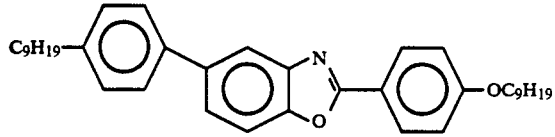
(1-123)
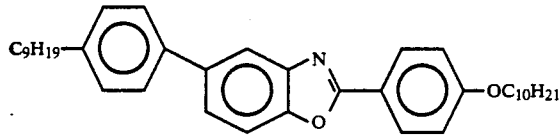
(1-124)
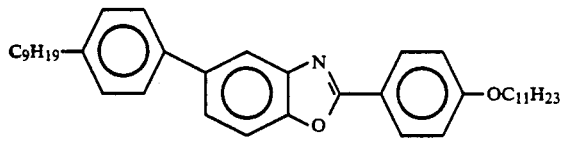
(1-125)
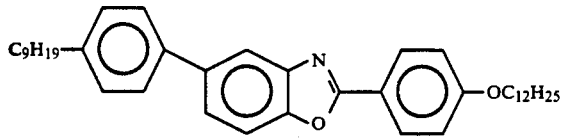
(1-126)
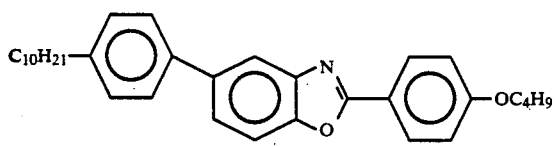
(1-127)
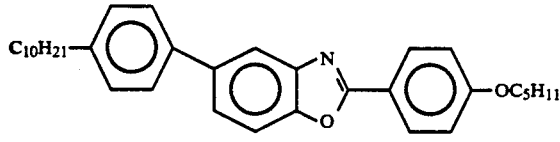
(1-128)
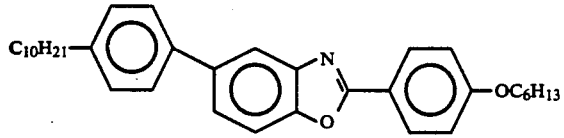
(1-129)
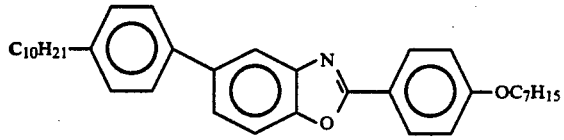
(1-130)

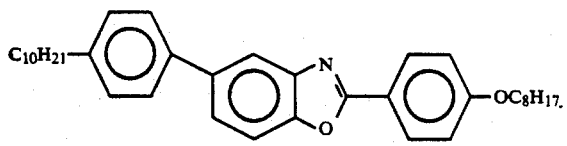
(1-131)
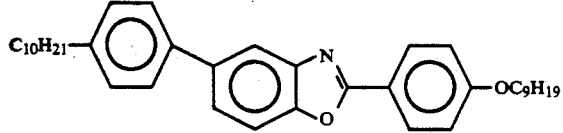
(1-132)
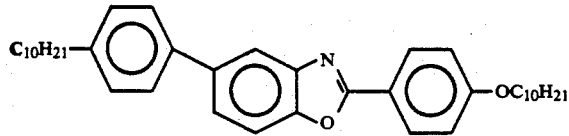
(1-133)
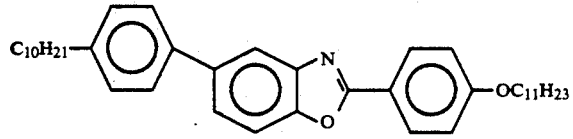
(1-134)
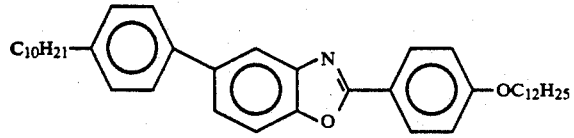
(1-135)
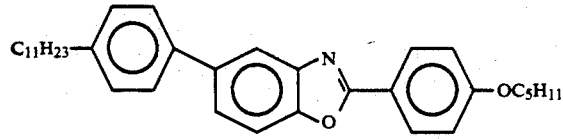
(1-136)
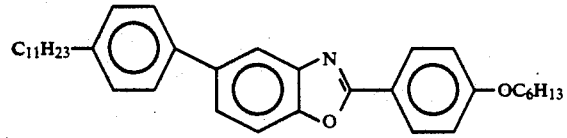
(1-137)
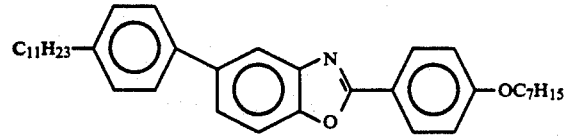
(1-138)
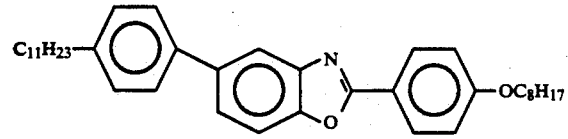
(1-139)
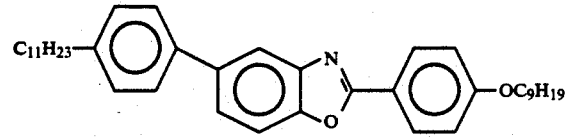
(1-140)

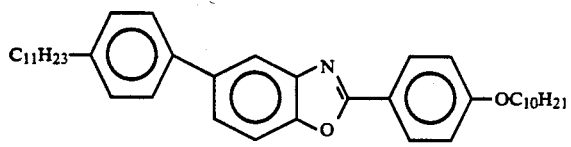 (1-141)
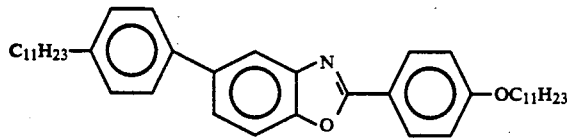 (1-142)
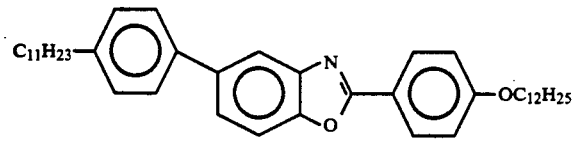 (1-143)
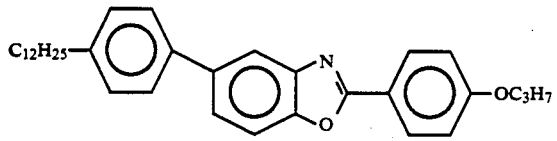 (1-144)
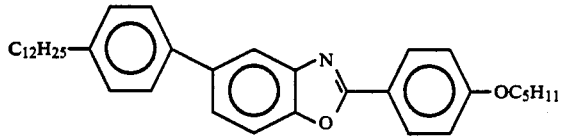 (1-145)
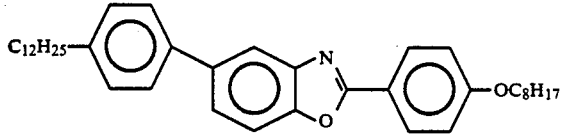 (1-146)
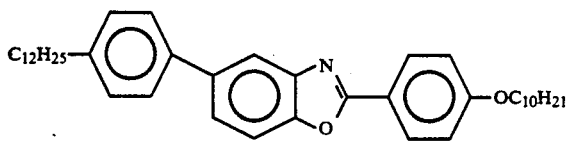 (1-147)
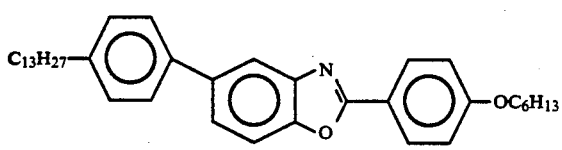 (1-148)
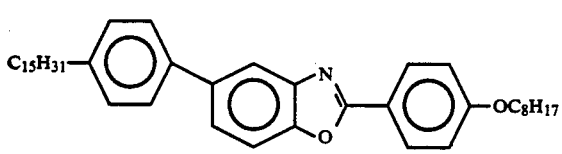 (1-149)
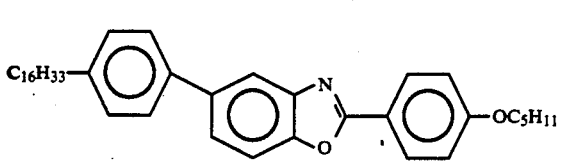 (1-150)

-continued
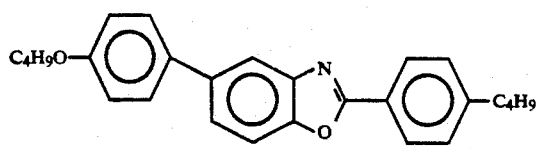 (1-151)
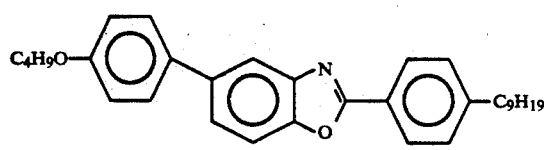 (1-152)
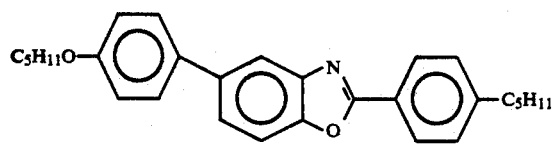 (1-153)
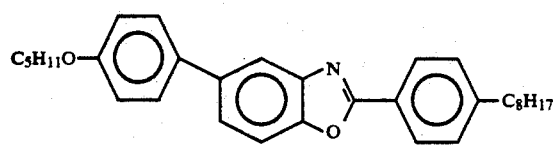 (1-154)
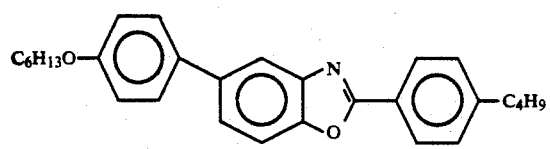 (1-155)
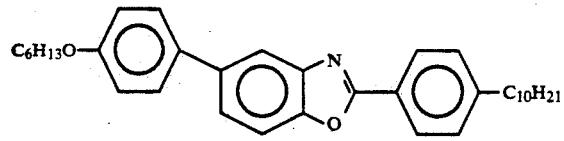 (1-156)
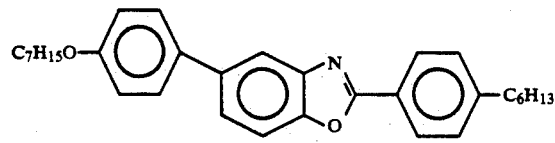 (1-157)
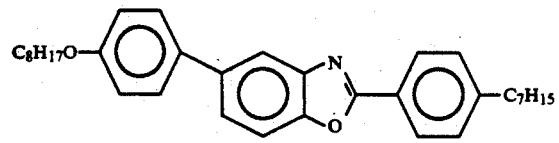 (1-158)
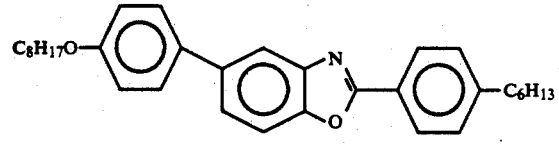 (1-159)
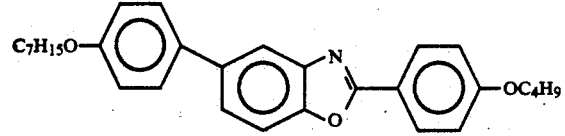 (1-160)

-continued
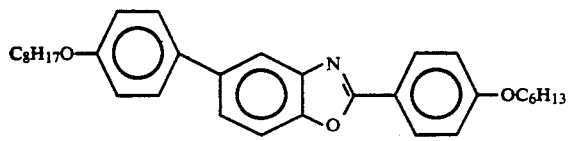 (1-161)
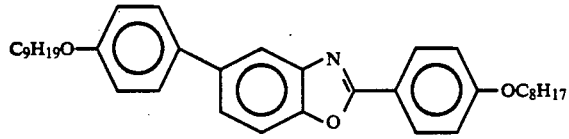 (1-162)
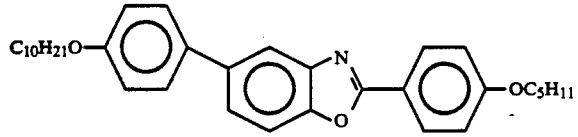 (1-163)
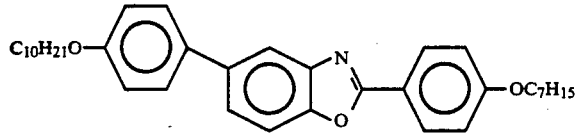 (1-164)
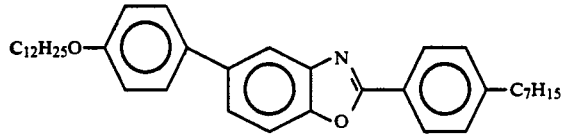 (1-165)
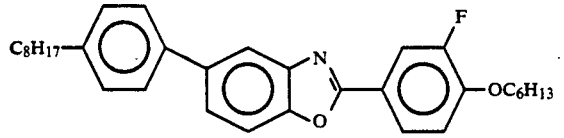 (1-166)
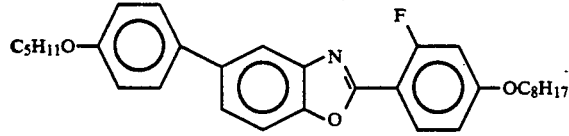 (1-167)
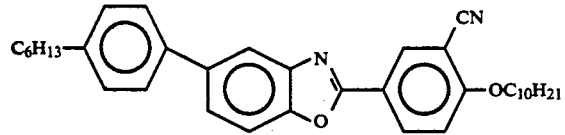 (1-168)
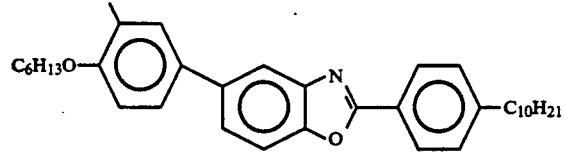 (1-169)
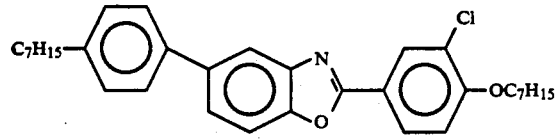 (1-170)

-continued
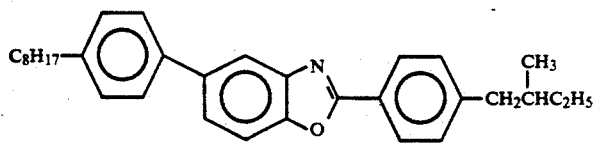 (1-171)
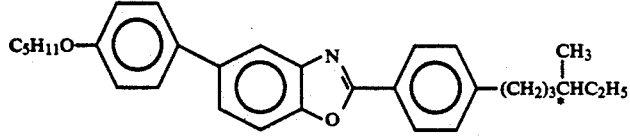 (1-172)
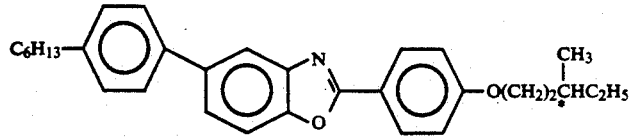 (1-173)
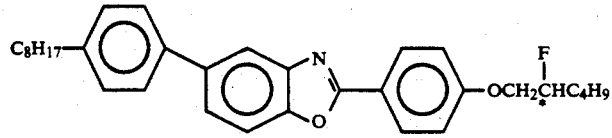 (1-174)
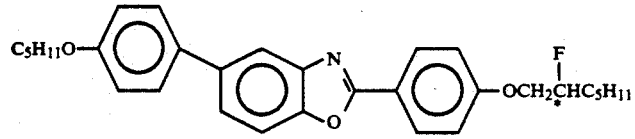 (1-175)
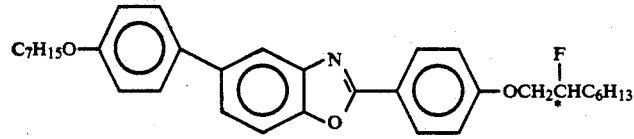 (1-176)
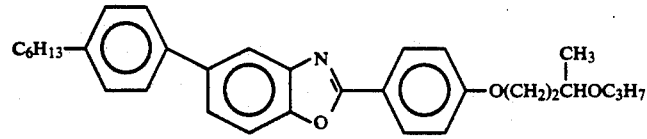 (1-177)
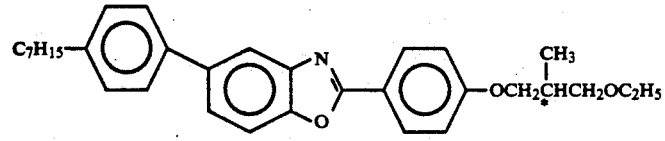 (1-178)
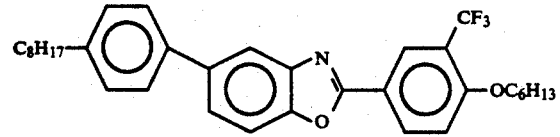 (1-179)
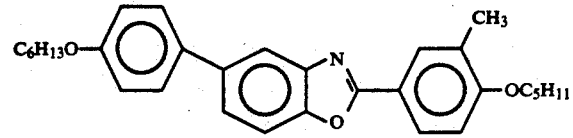 (1-180)

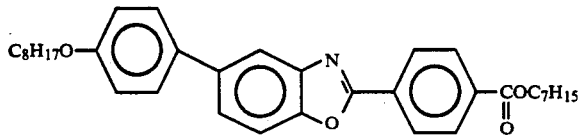 (1-181)
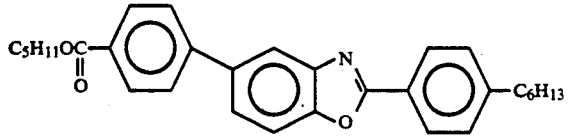 (1-182)
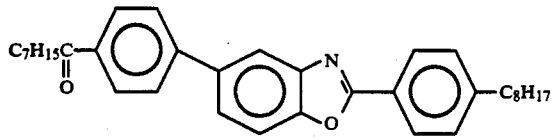 (1-183)
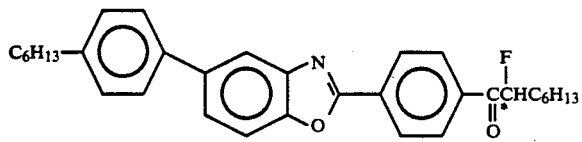 (1-184)
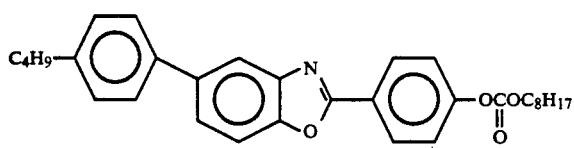 (1-185)
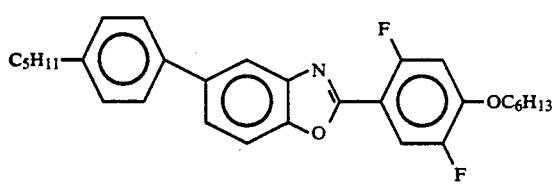 (1-186)
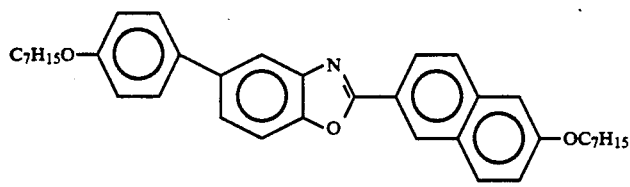 (1-187)
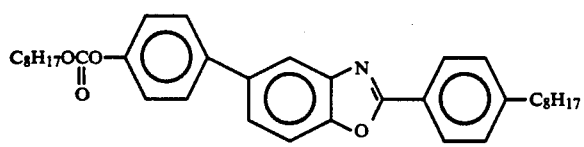 (1-188)
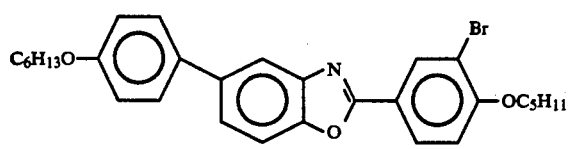 (1-189)
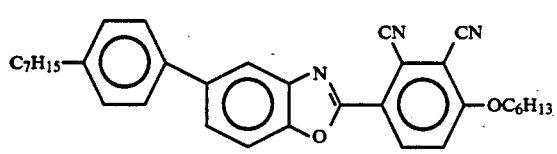 (1-190)

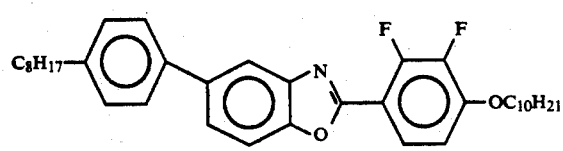
(1-191)
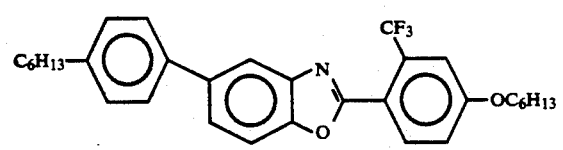
(1-192)
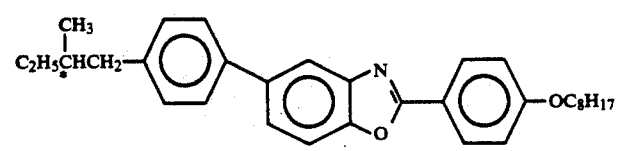
(1-193)
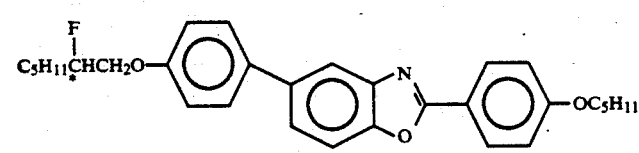
(1-194)
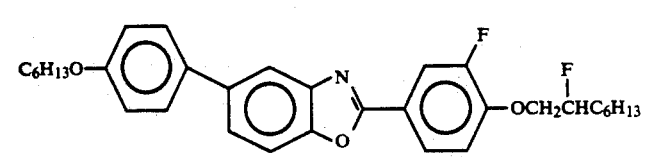
(1-195)
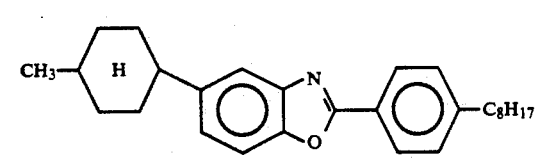
(1-196)
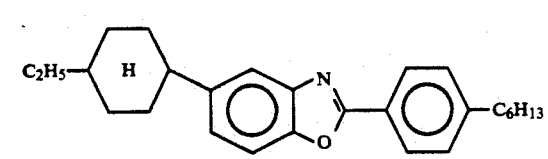
(1-197)
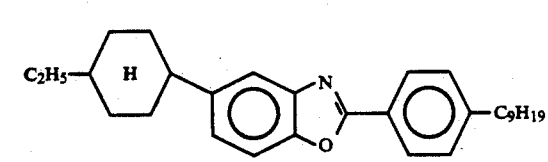
(1-198)
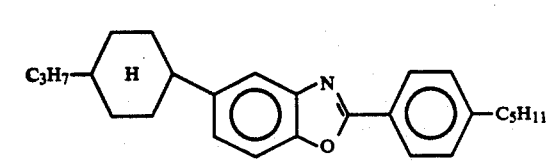
(1-199)
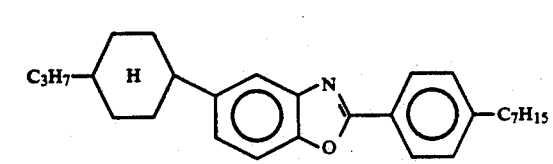
(1-200)

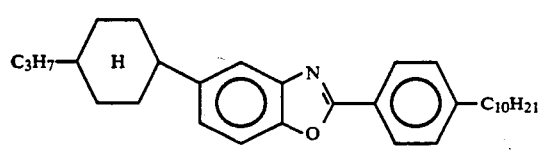
(1-201)
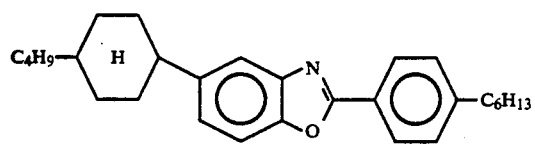
(1-202)
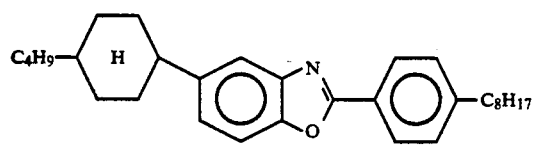
(1-203)
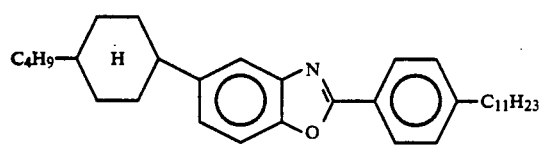
(1-204)
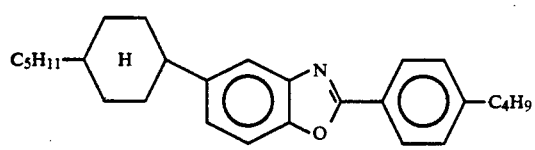
(1-205)
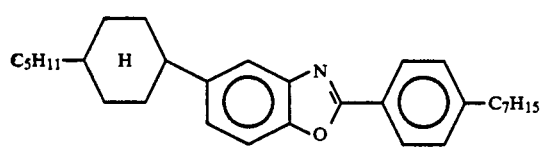
(1-206)
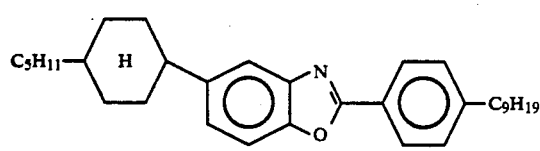
(1-207)
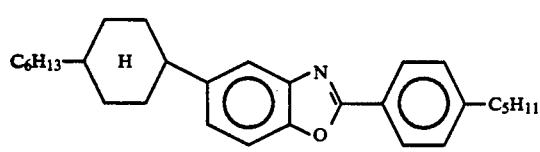
(1-208)
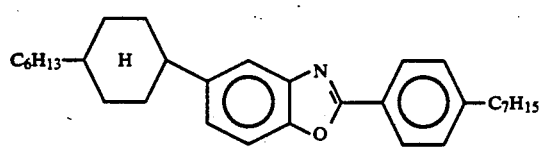
(1-209)
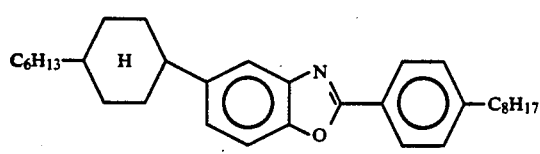
(1-210)

-continued
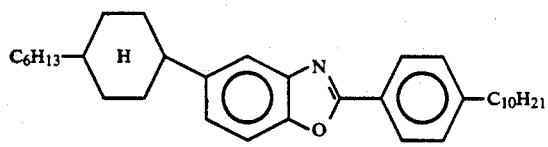 (1-211)
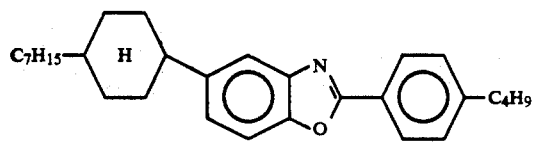 (1-212)
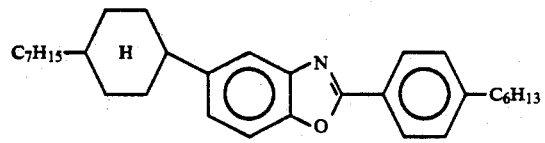 (1-213)
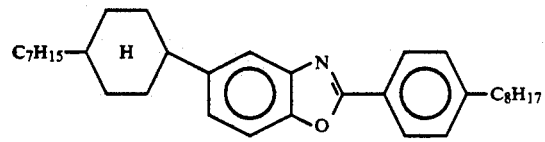 (1-214)
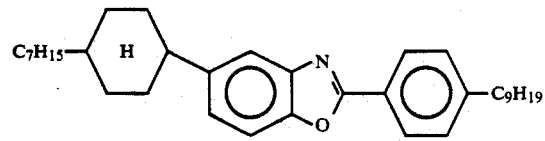 (1-215)
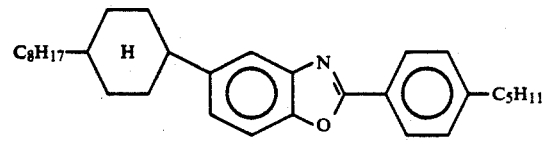 (1-216)
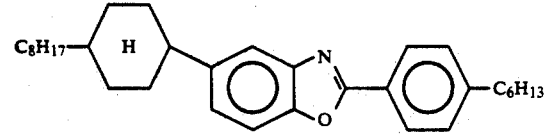 (1-217)
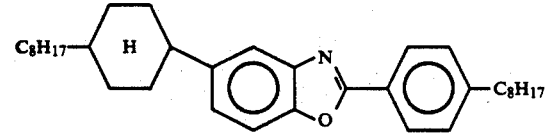 (1-218)
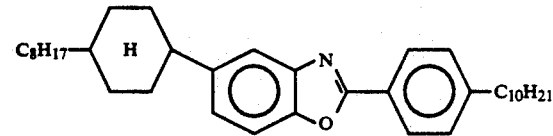 (1-219)
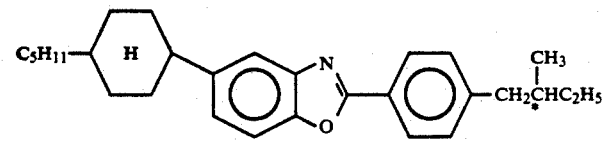 (1-220)

-continued
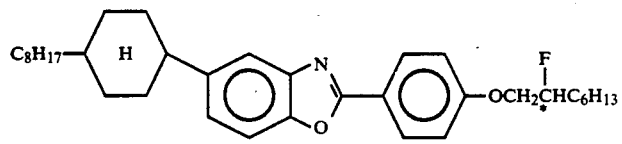 (1-221)
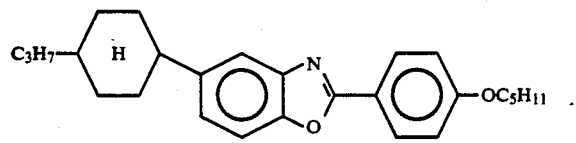 (1-222)
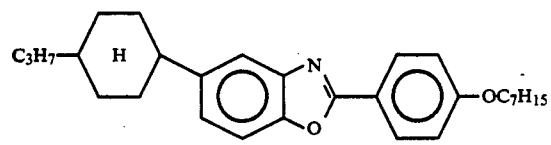 (1-223)
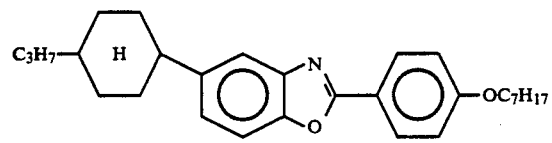 (1-224)
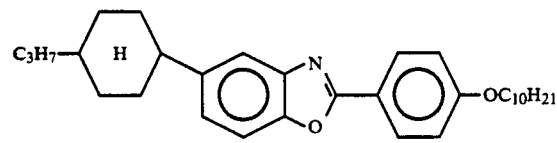 (1-225)
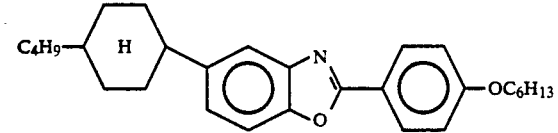 (1-226)
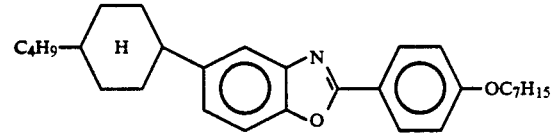 (1-227)
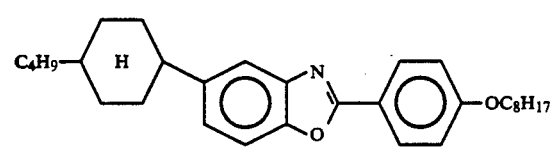 (1-228)
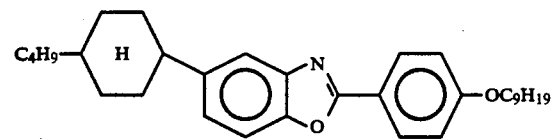 (1-229)
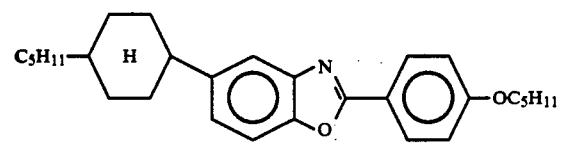 (1-230)

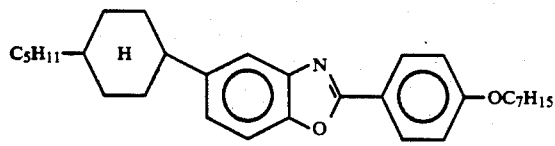 (1-231)
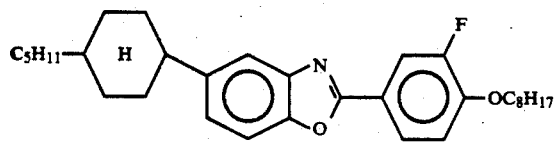 (1-232)
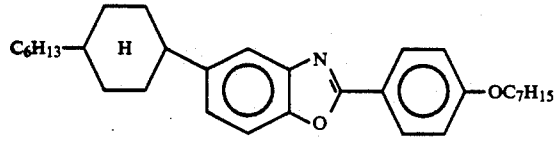 (1-233)
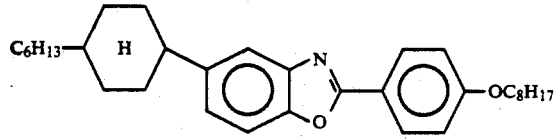 (1-234)
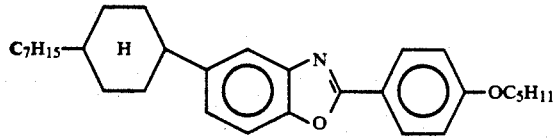 (1-235)
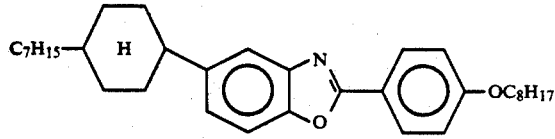 (1-236)
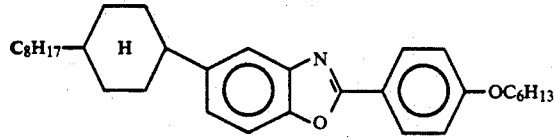 (1-237)
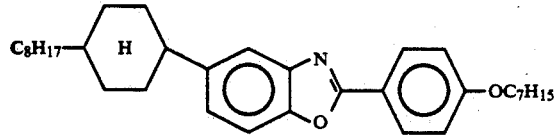 (1-238)
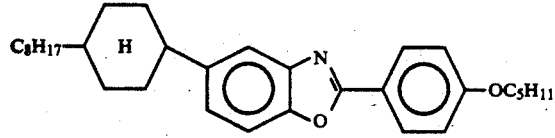 (1-239)
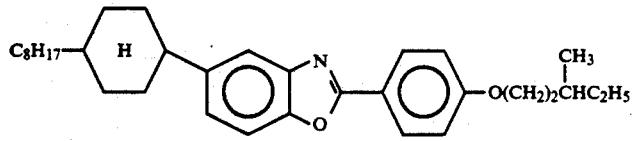 (1-240)

-continued
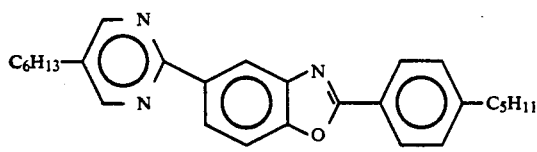 (1-241)
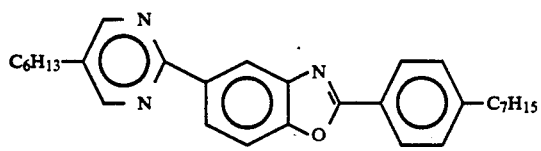 (1-242)
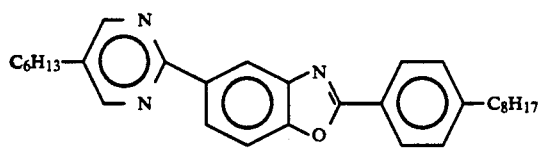 (1-243)
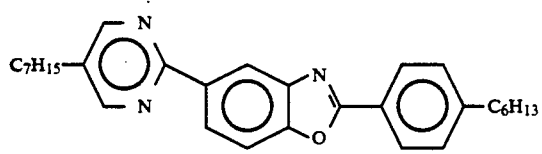 (1-244)
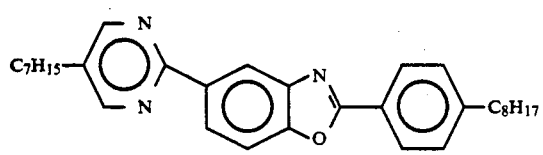 (1-245)
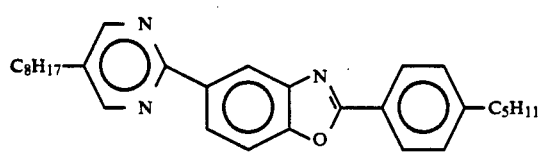 (1-246)
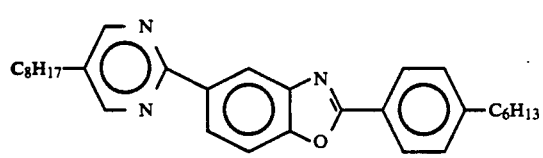 (1-247)
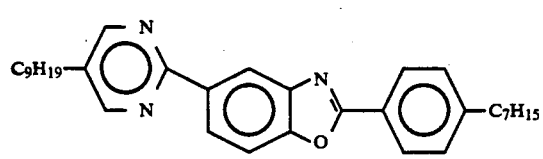 (1-248)
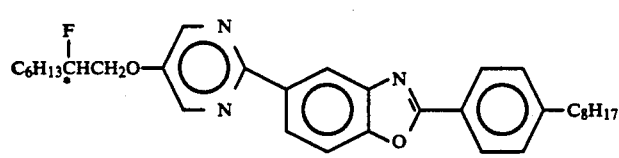 (1-249)
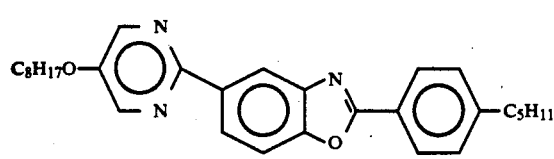 (1-250)

-continued
(1-251) 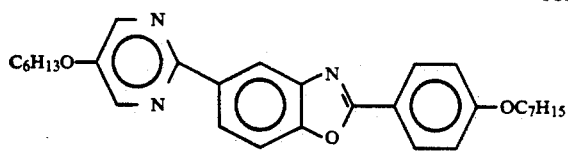
(1-252) 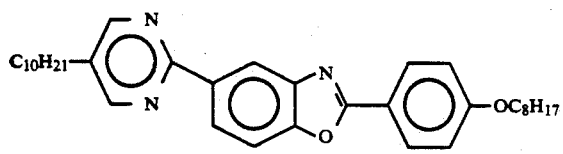
(1-253) 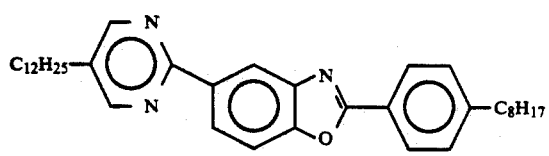
(1-254) 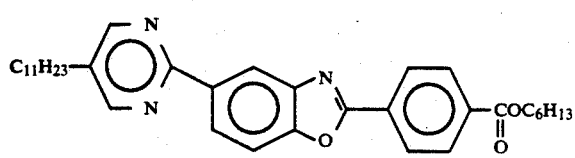
(1-255) 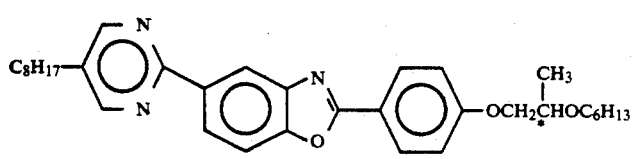
(1-256) 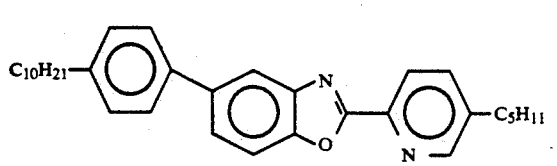
(1-257) 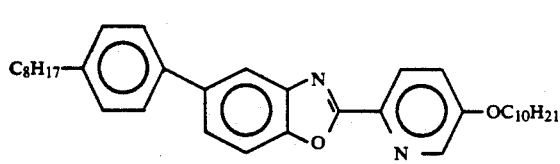
(1-258) 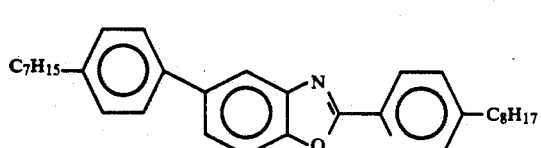
(1-259) 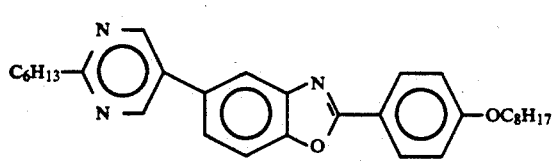
(1-260) 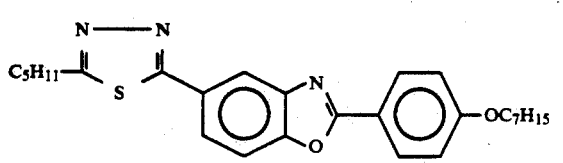

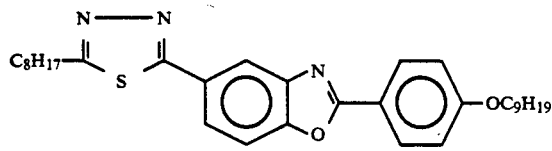
(1-261)
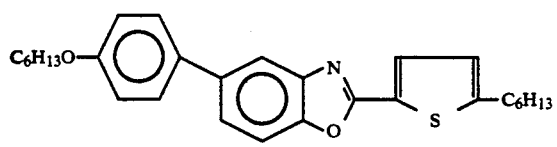
(1-262)
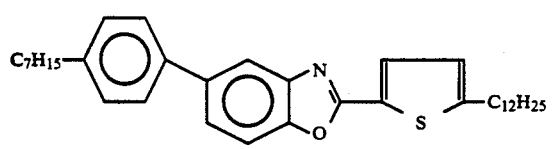
(1-263)
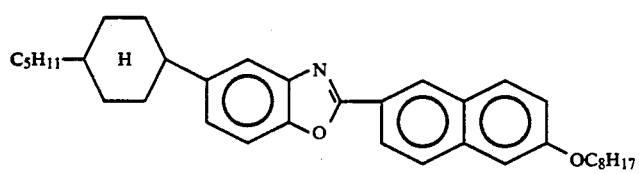
(1-264)
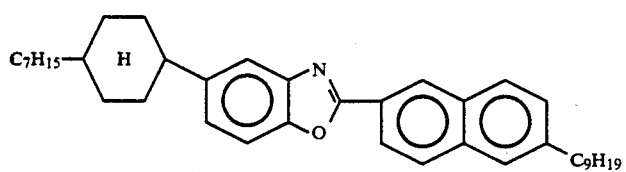
(1-265)
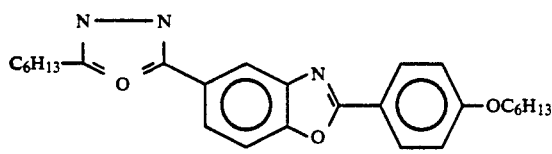
(1-266)
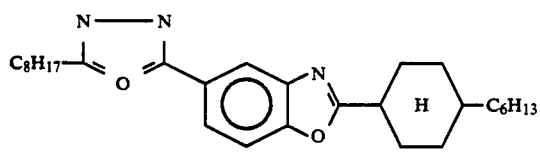
(1-267)
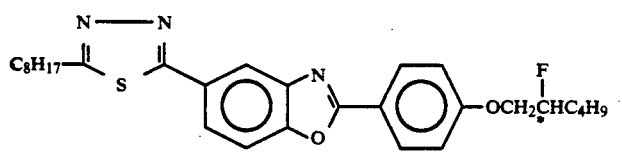
(1-268)
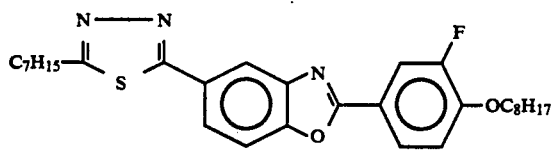
(1-269)
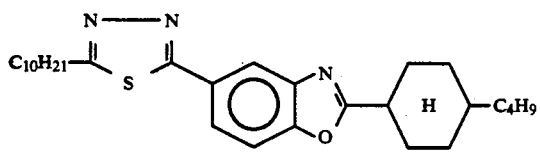
(1-270)

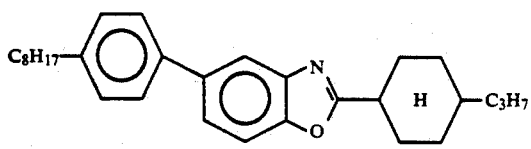
(1-271)
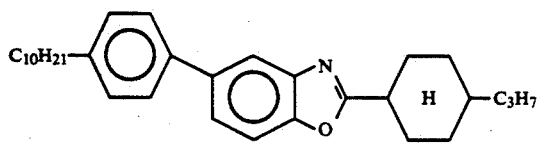
(1-272)
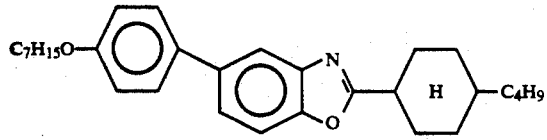
(1-273)
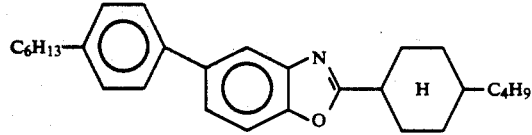
(1-274)
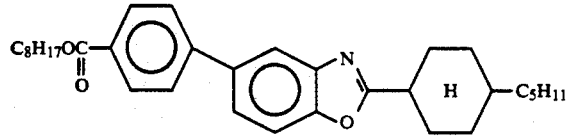
(1-275)
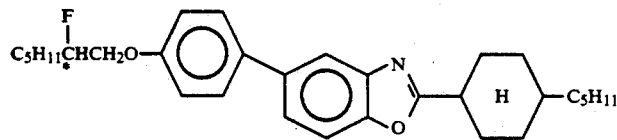
(1-276)
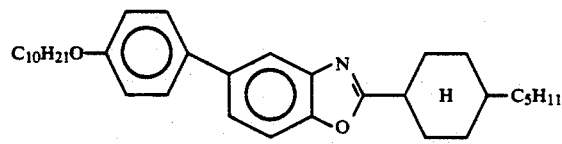
(1-277)
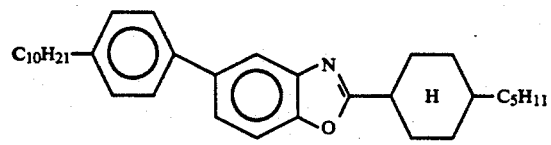
(1-278)
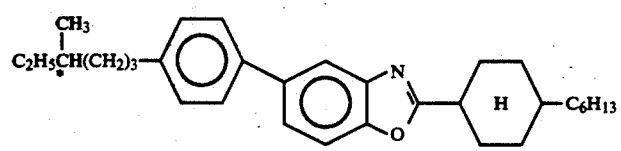
(1-279)
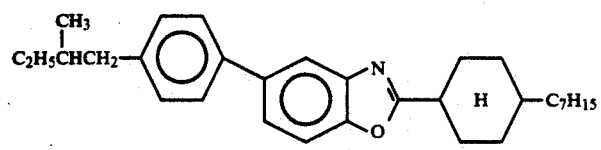
(1-280)

-continued
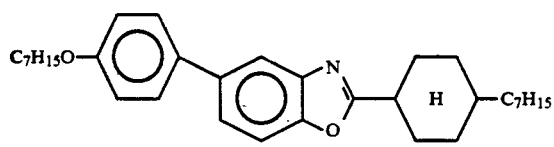 (1-281)
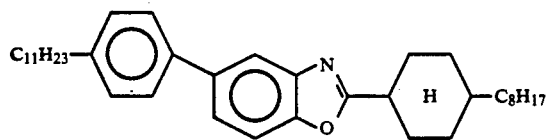 (1-282)
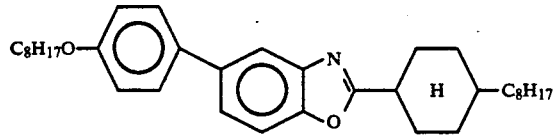 (1-283)
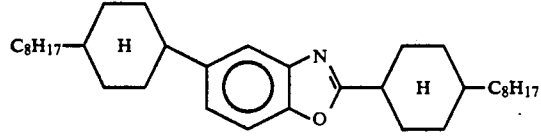 (1-284)
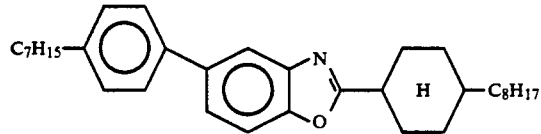 (1-285)
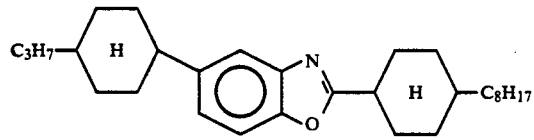 (1-286)
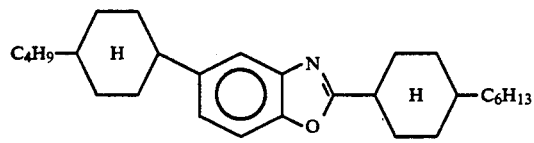 (1-287)
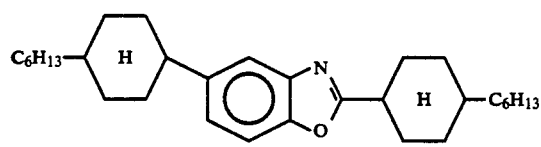 (1-288)
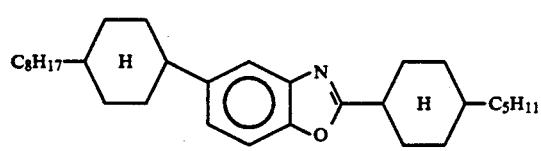 (1-289)
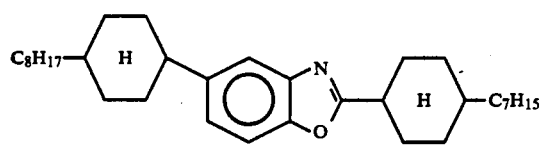 (1-290)

-continued

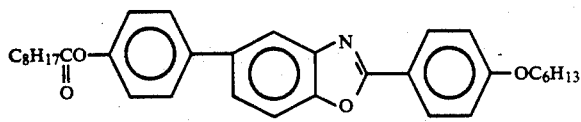
(1-291)

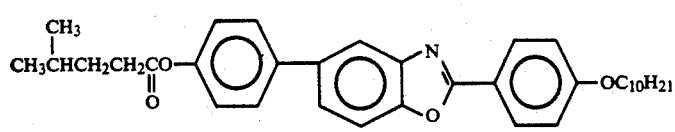
(1-292)

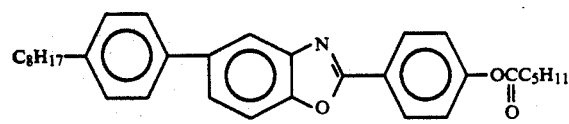
(1-293)

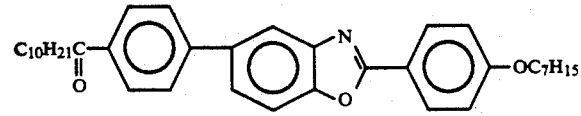
(1-294)

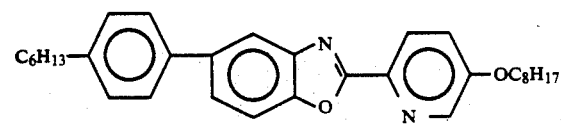
(1-295)

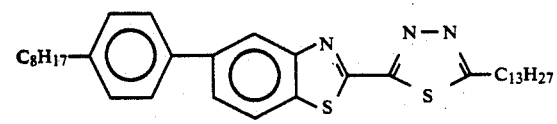
(1-296)

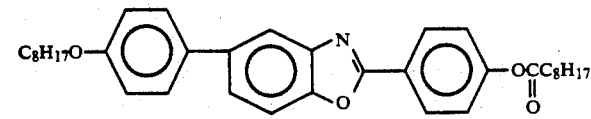
(1-297)

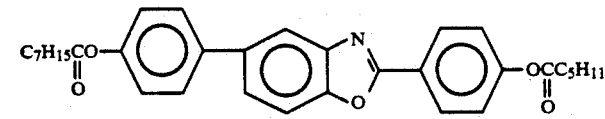
(1-298)

The liquid crystal composition according to the present invention may be obtained by mixing at least one species of the compound represented by the formula (I) and at least one species of another mesomorphic compound in appropriate proportions. The liquid crystal composition according to the present invention may preferably be formulated as a ferroelectric liquid crystal composition, particularly a ferroelectric chiral smectic liquid crystal composition.

Specific examples of another mesomorphic compound as described above may include those denoted by the following structural formulas.

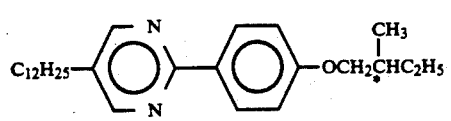
(1)

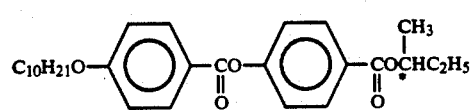
(2)

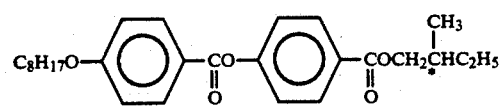
(3)

-continued
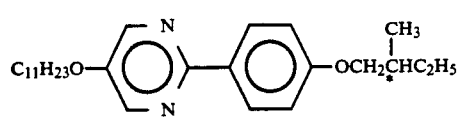 (4)
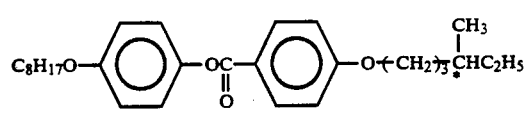 (5)
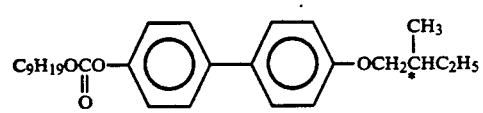 (6)
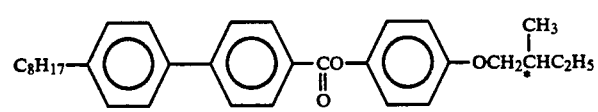 (7)
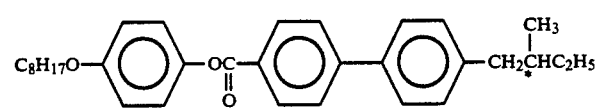 (8)
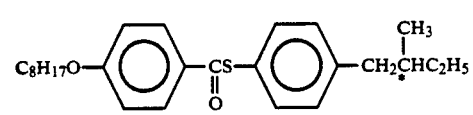 (9)
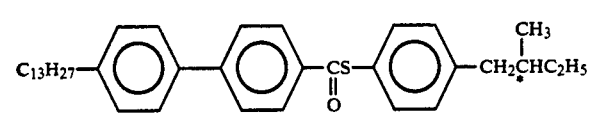 (10)
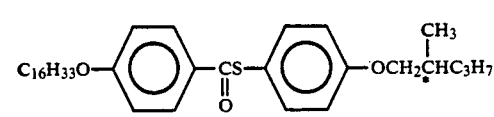 (11)
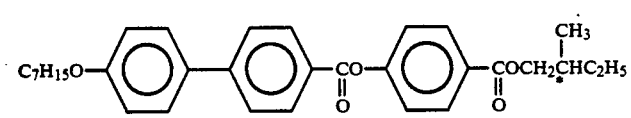 (12)
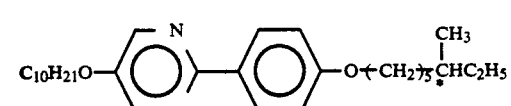 (13)
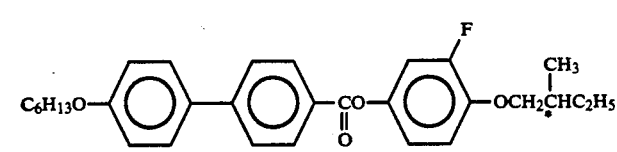 (14)
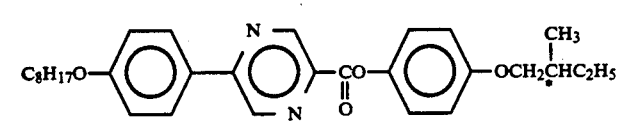 (15)
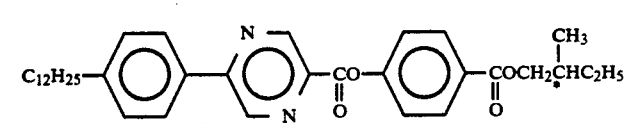 (16)

-continued
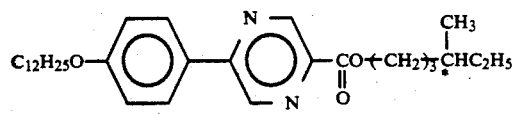 (17)
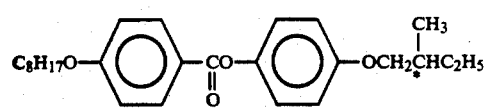 (18)
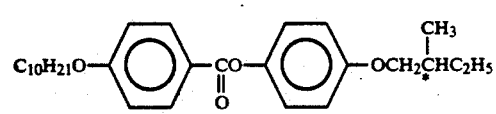 (19)
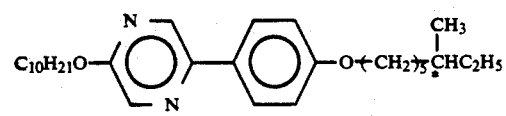 (20)
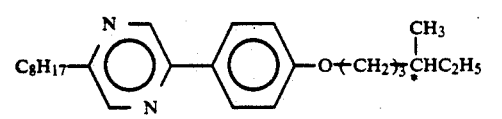 (21)
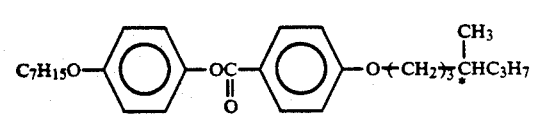 (22)
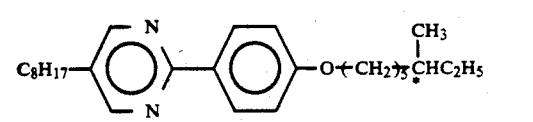 (23)
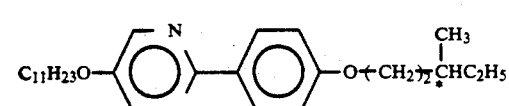 (24)
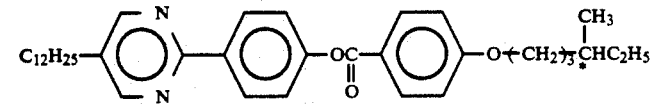 (25)
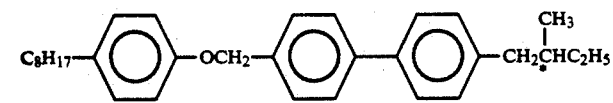 (26)
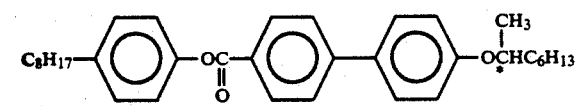 (27)
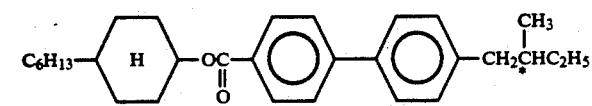 (28)
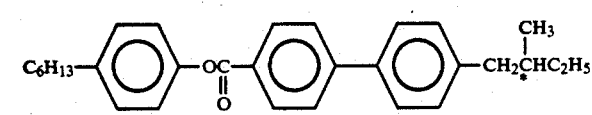 (29)

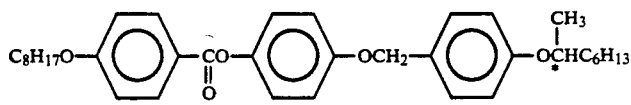 (30)
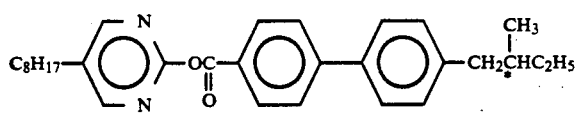 (31)
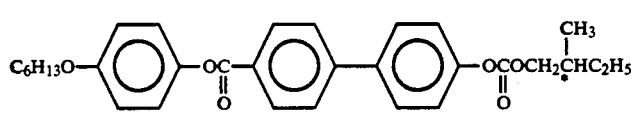 (32)
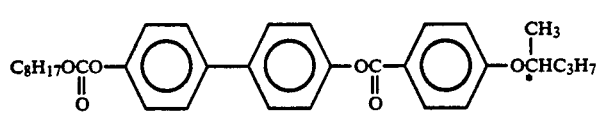 (33)
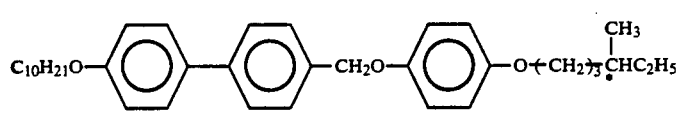 (34)
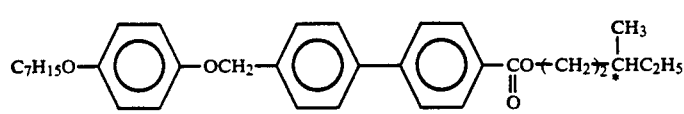 (35)
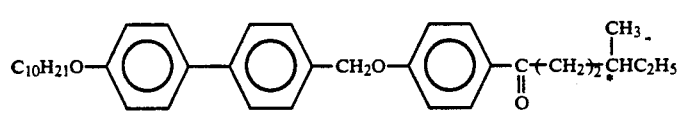 (36)
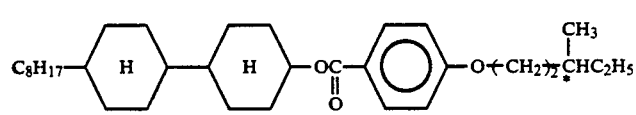 (37)
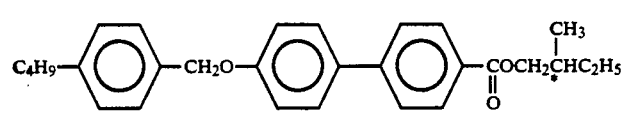 (38)
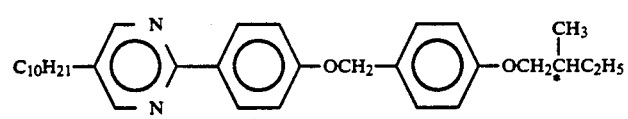 (39)
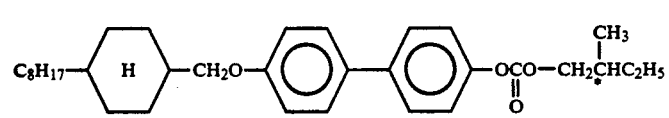 (40)
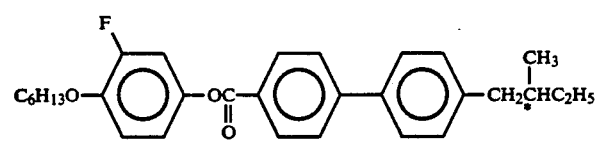 (41)
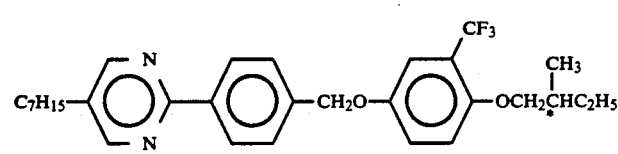 (42)

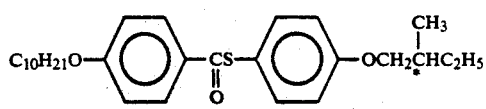 (43)
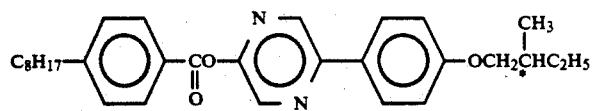 (44)
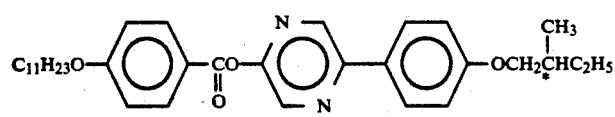 (45)
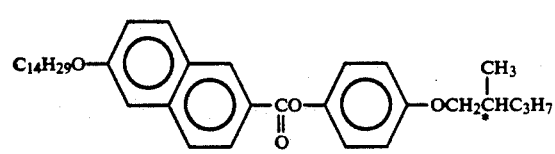 (46)
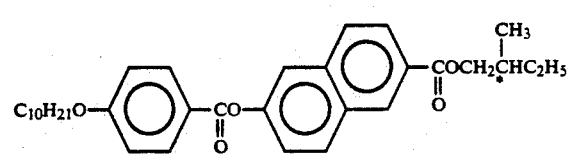 (47)
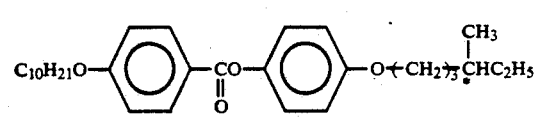 (48)
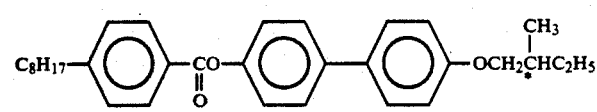 (49)
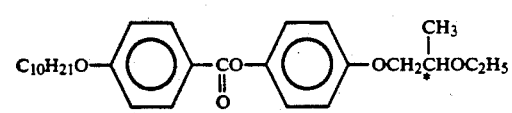 (50)
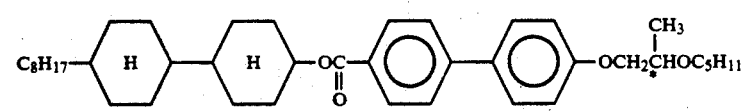 (51)
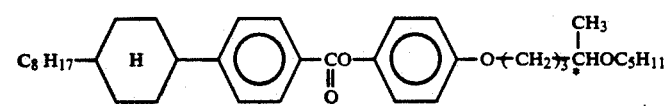 (52)
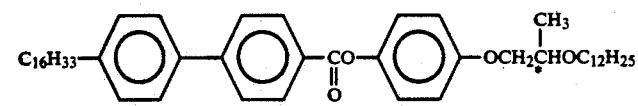 (53)
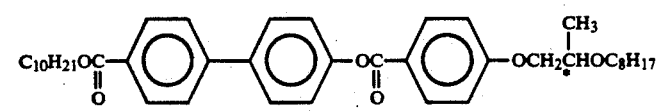 (54)
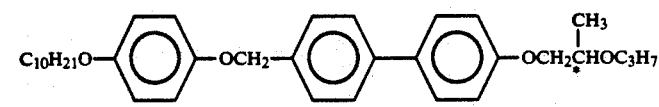 (55)

-continued
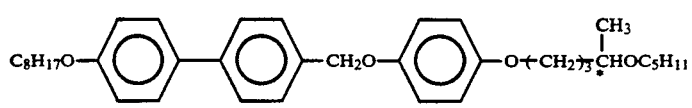 (56)
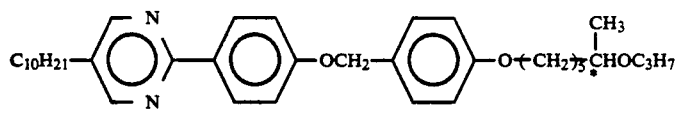 (57)
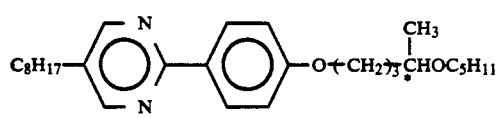 (58)
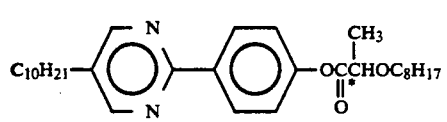 (59)
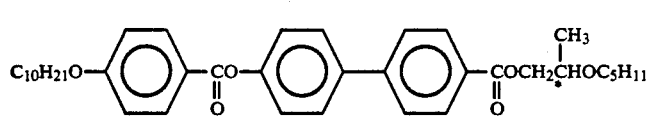 (60)
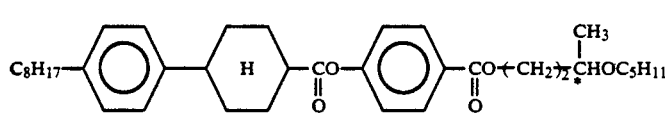 (61)
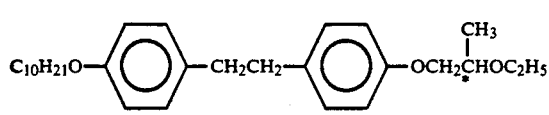 (62)
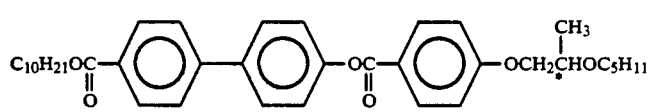 (63)
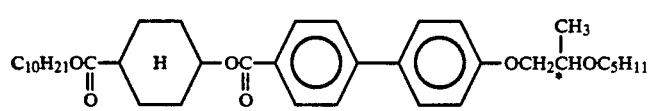 (64)
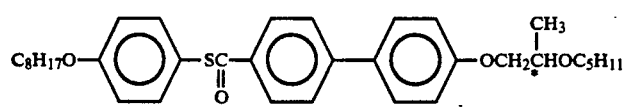 (65)
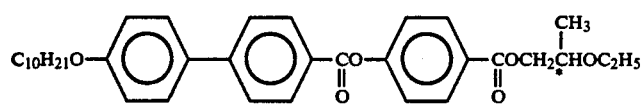 (66)
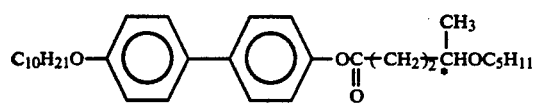 (67)
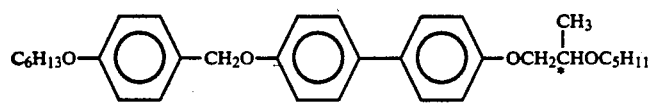 (68)

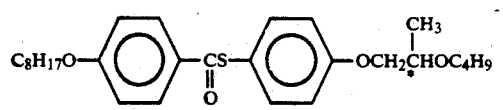
(69)
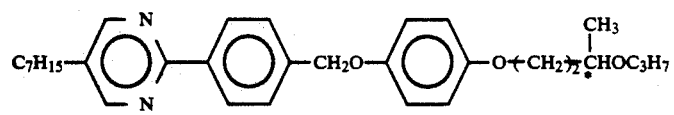
(70)
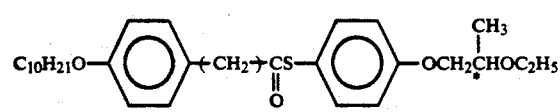
(71)
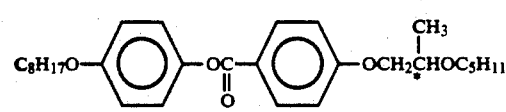
(72)
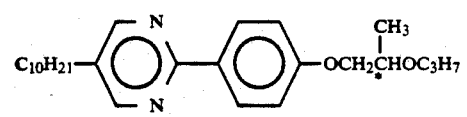
(73)
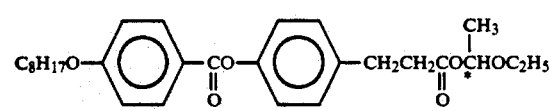
(74)
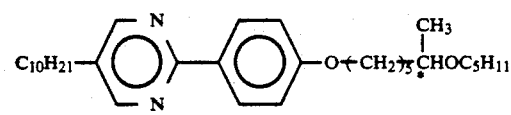
(75)
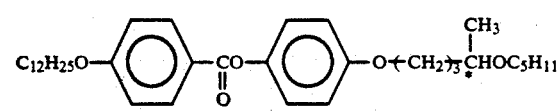
(76)
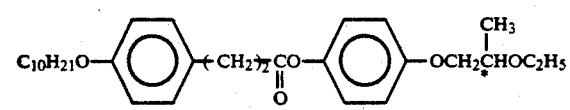
(77)
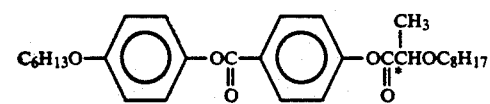
(78)
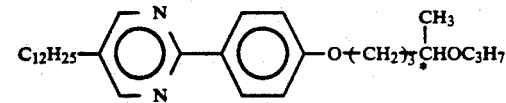
(79)
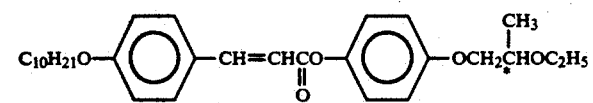
(80)
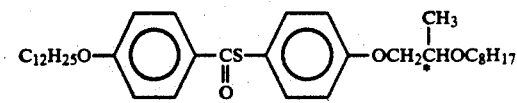
(81)

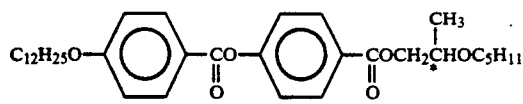
(82)
(83)
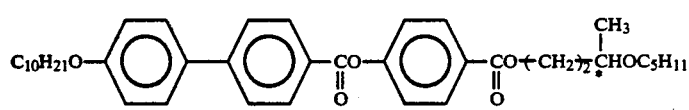
(84)
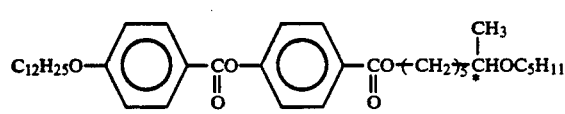
(85)
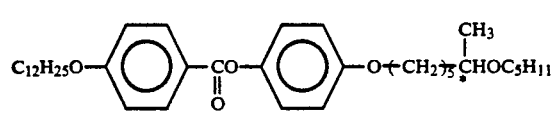
(86)
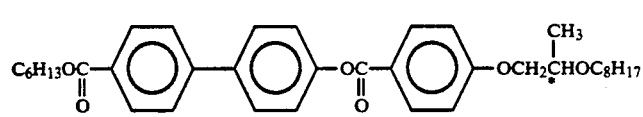
(87)
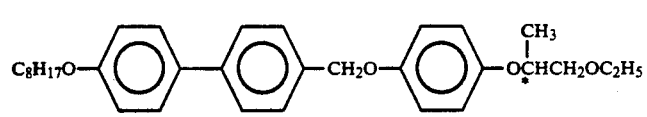
(88)
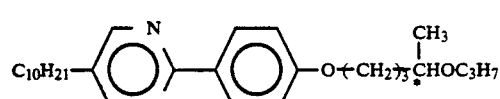
(89)
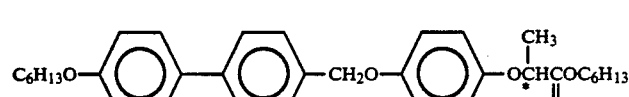
(90)
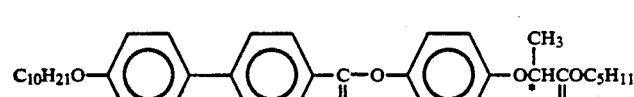
(91)
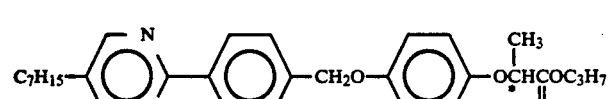
(92)
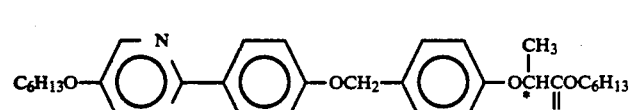
(93)
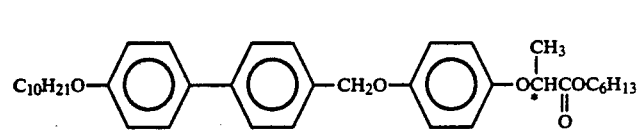
(94)

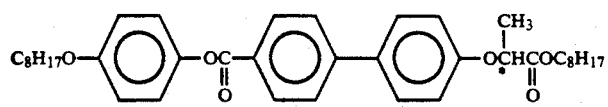 (95)
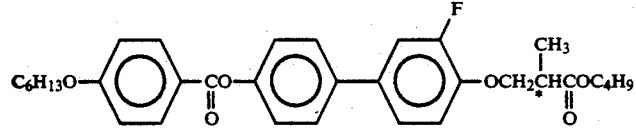 (96)
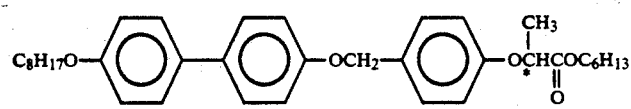 (97)
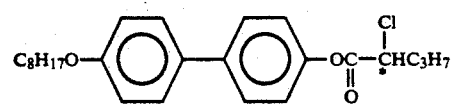 (98)
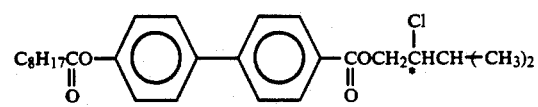 (99)
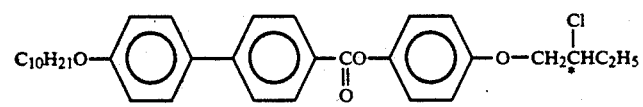 (100)
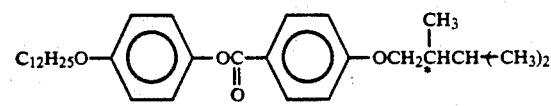 (101)
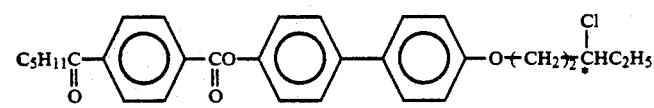 (102)
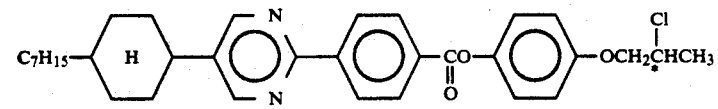 (103)
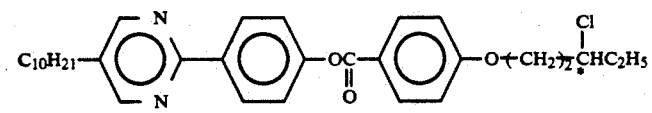 (104)
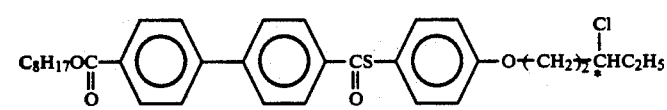 (105)
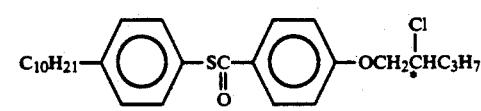 (106)
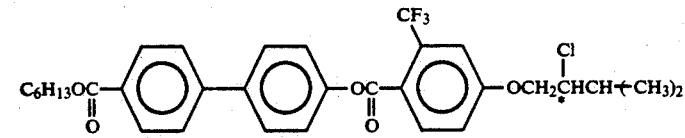 (107)

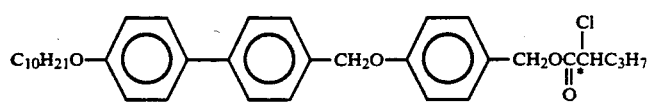 (108)
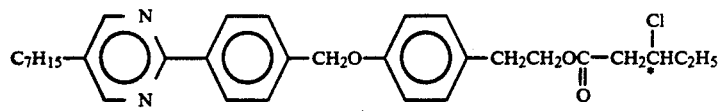 (109)
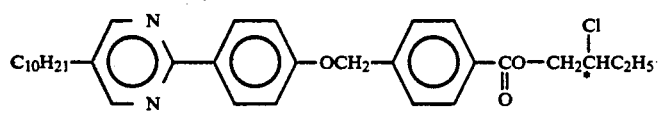 (110)
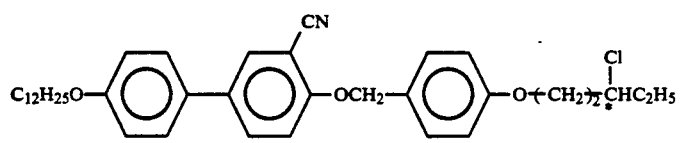 (111)
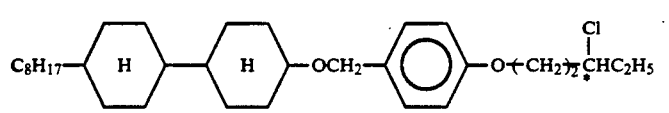 (112)
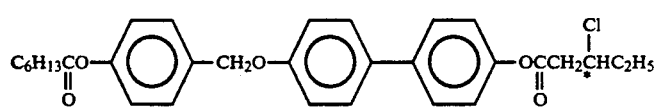 (113)
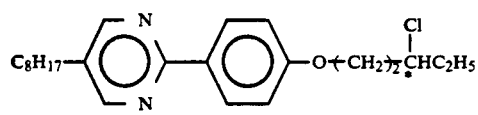 (114)
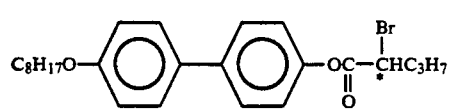 (115)
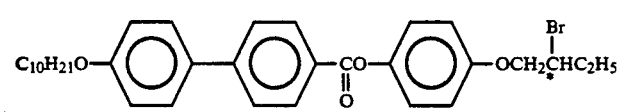 (116)
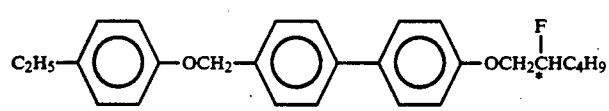 (117)
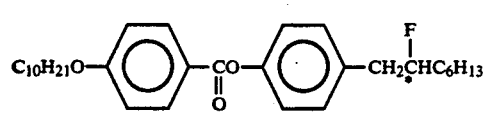 (118)
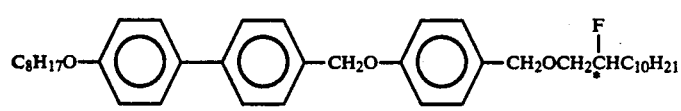 (119)
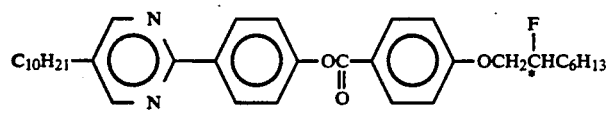 (120)

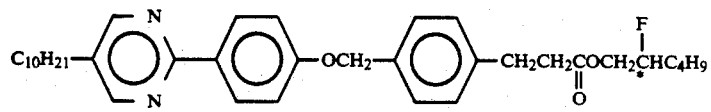 (121)
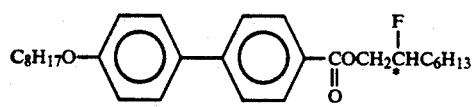 (122)
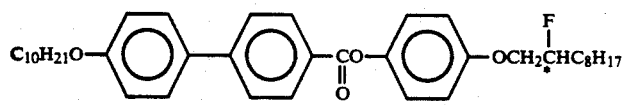 (123)
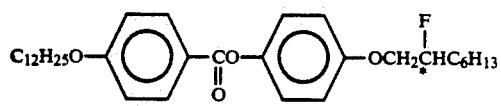 (124)
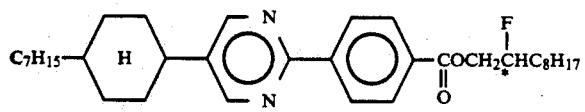 (125)
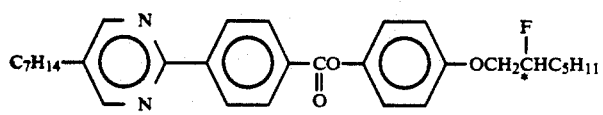 (126)
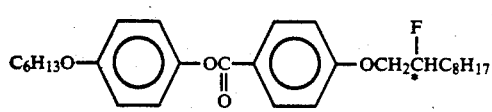 (127)
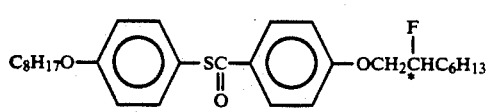 (128)
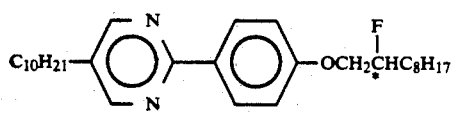 (129)
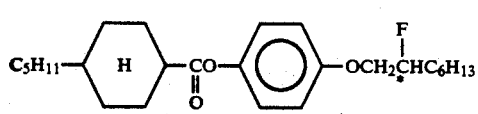 (130)
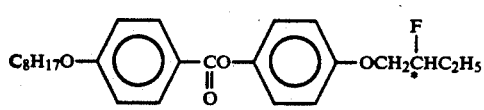 (131)
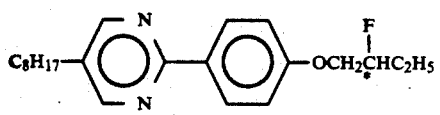 (132)
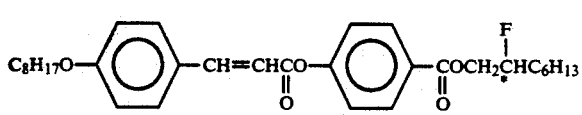 (133)

-continued
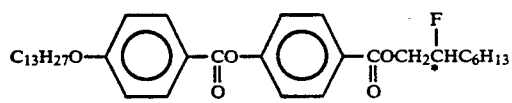 (134)
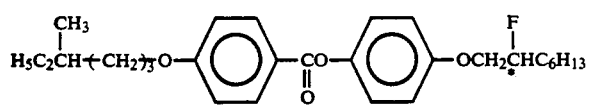 (135)
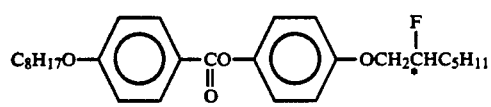 (136)
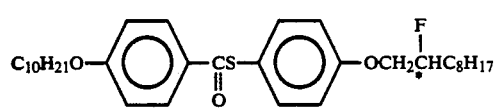 (137)
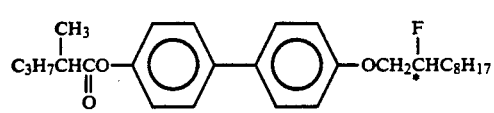 (138)
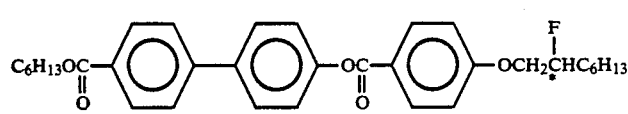 (139)
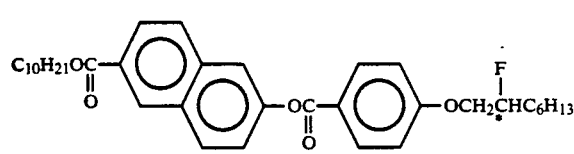 (140)
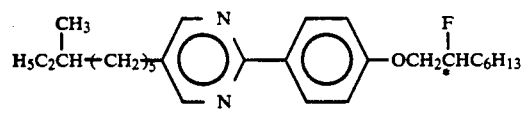 (141)
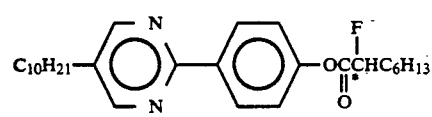 (142)
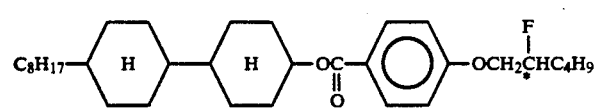 (143)
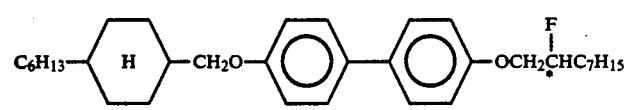 (144)
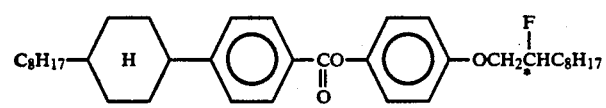 (145)
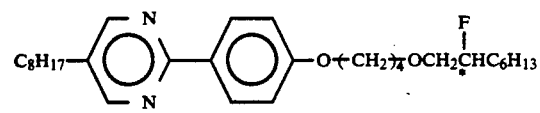 (146)

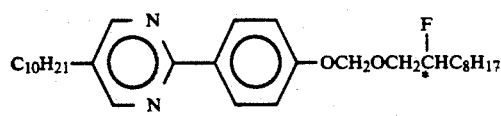 (147)
 (148)
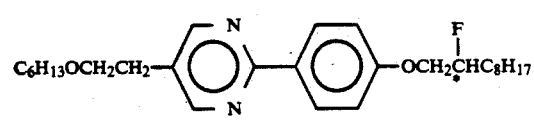 (149)
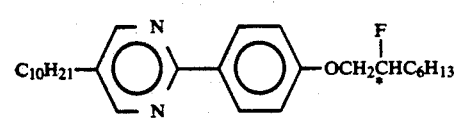 (150)
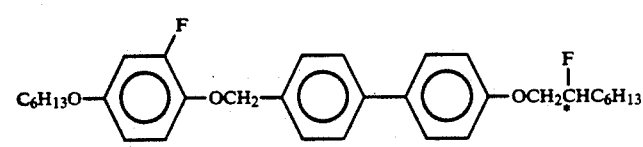 (151)
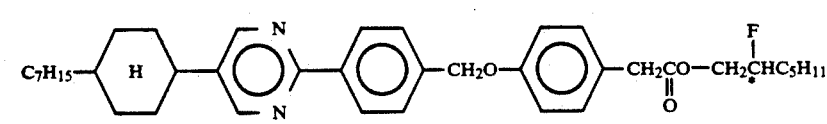 (152)
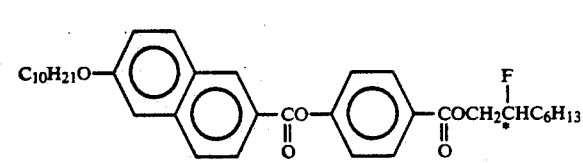 (153)
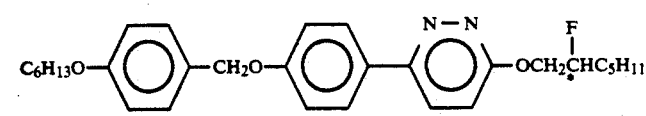 (154)
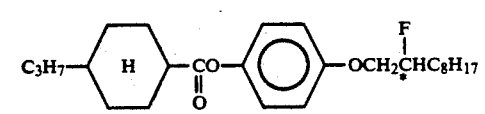 (155)
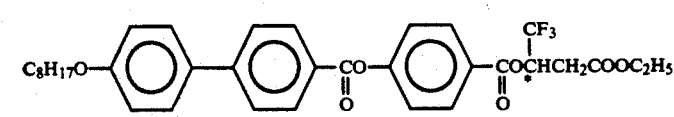 (156)
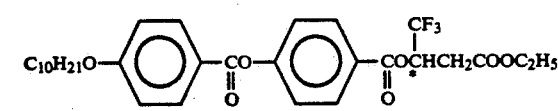 (157)
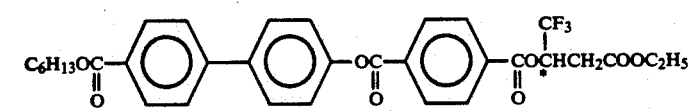 (158)
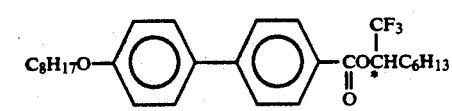 (159)

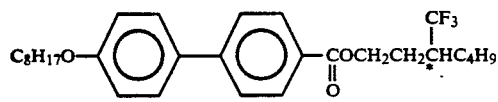 (160)
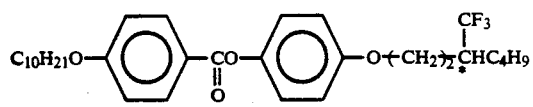 (161)
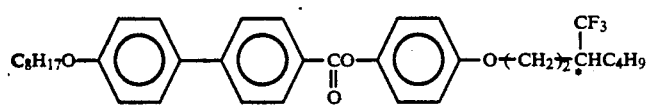 (162)
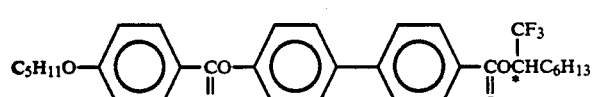 (163)
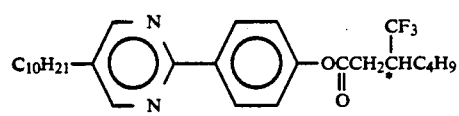 (164)
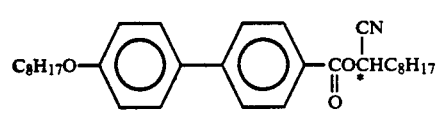 (165)
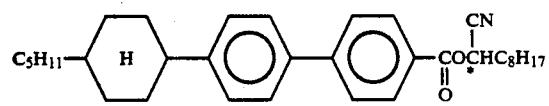 (166)
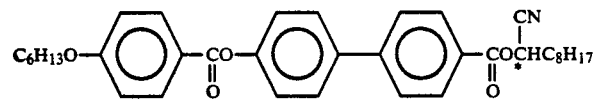 (167)
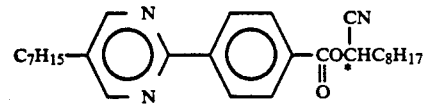 (168)
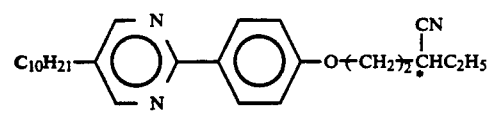 (169)
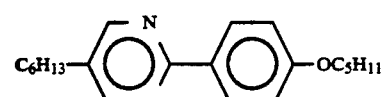 (170)
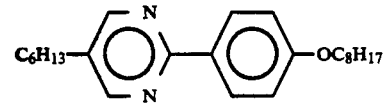 (171)
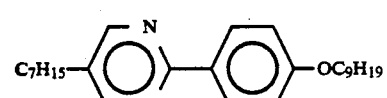 (172)

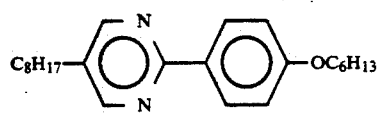 (173)
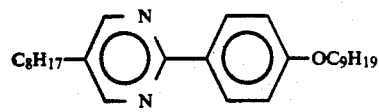 (174)
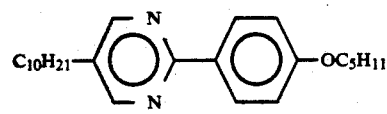 (175)
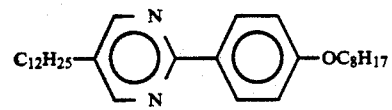 (176)
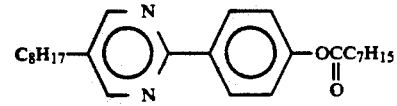 (177)
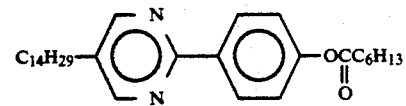 (178)
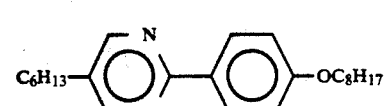 (179)
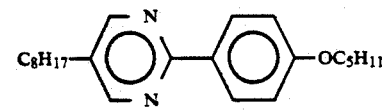 (180)
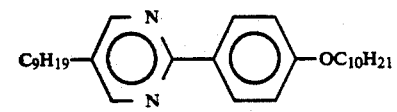 (181)
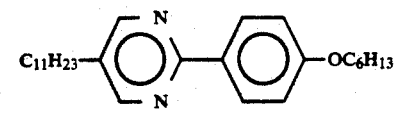 (182)
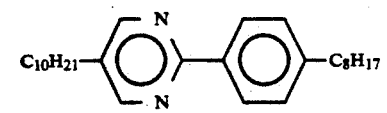 (183)
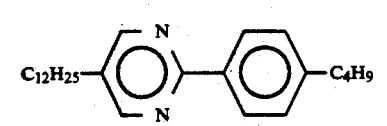 (184)
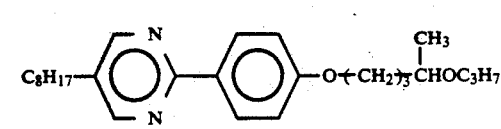 (185)

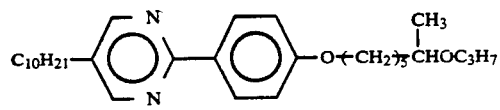 (186)
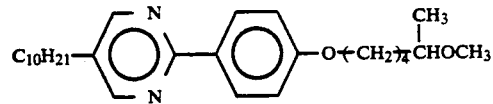 (187)
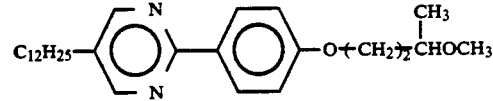 (188)
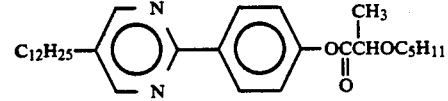 (189)
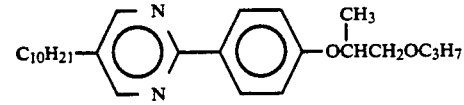 (190)
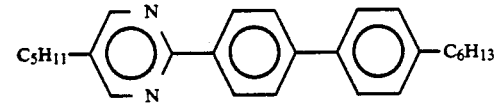 (191)
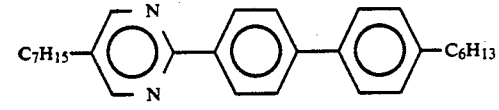 (192)
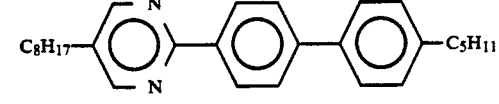 (193)
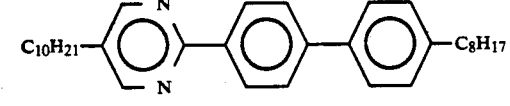 (194)
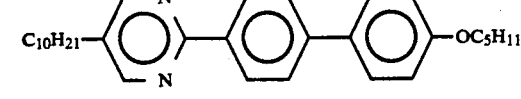 (195)
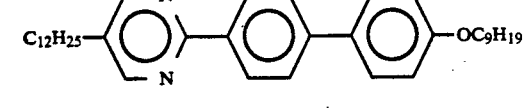 (196)
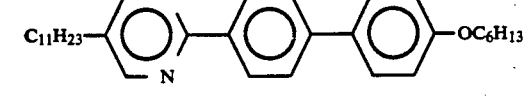 (197)
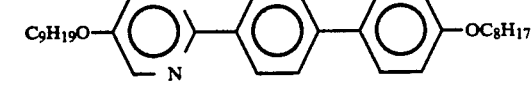 (198)

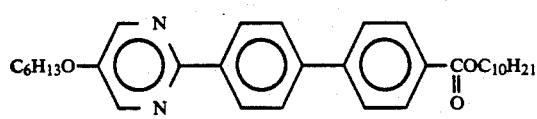 (199)
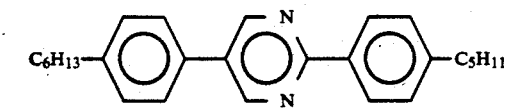 (200)
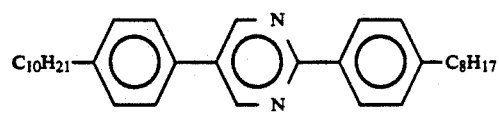 (201)
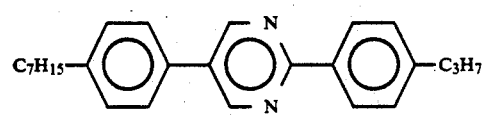 (202)
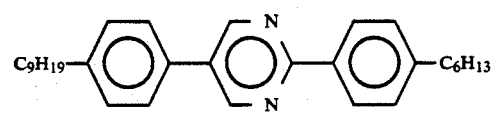 (203)
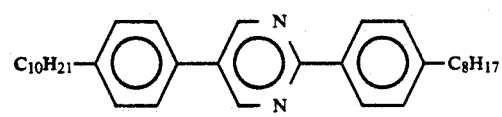 (204)
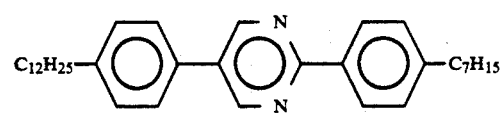 (205)
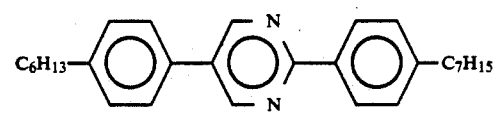 (206)
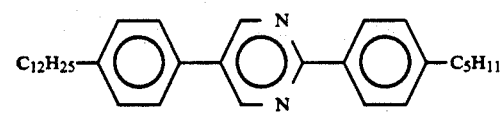 (207)
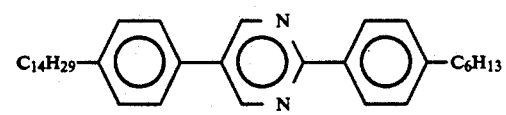 (208)
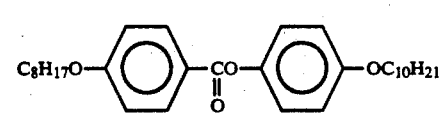 (209)
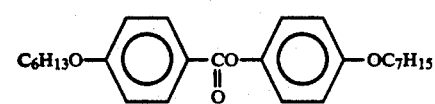 (210)
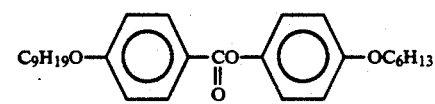 (211)

-continued
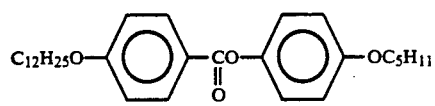
(212)
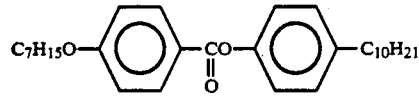
(213)
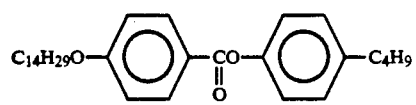
(214)
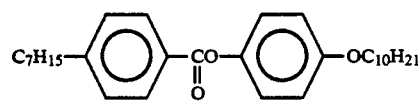
(215)
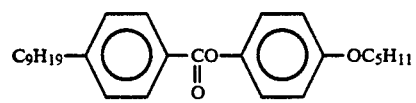
(216)
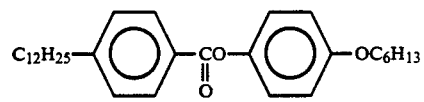
(217)
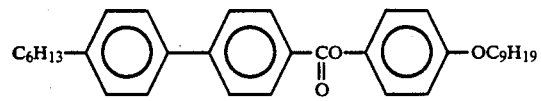
(218)
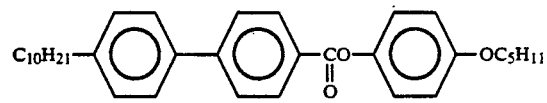
(219)
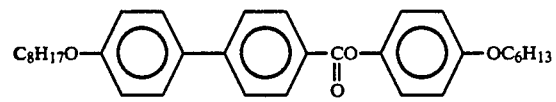
(220)
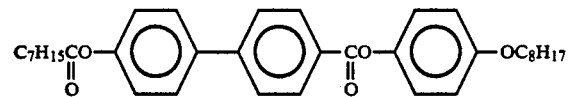
(221)
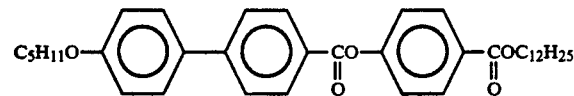
(222)
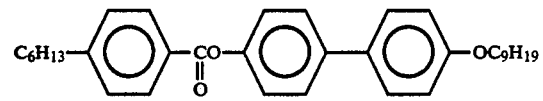
(223)
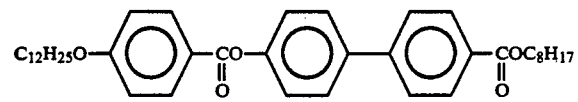
(224)
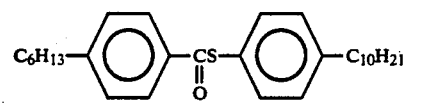
(225)

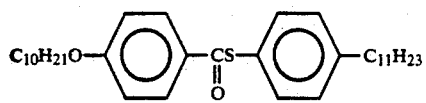 (226)
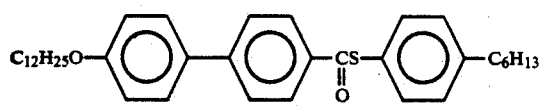 (227)
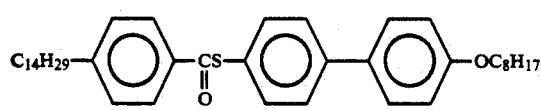 (228)
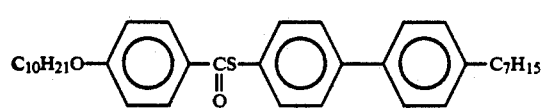 (229)
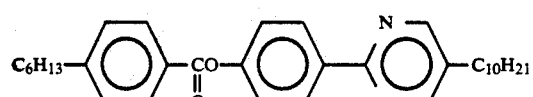 (230)
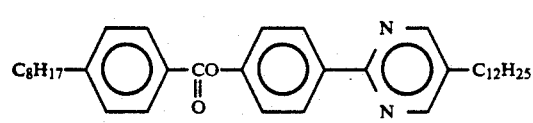 (231)
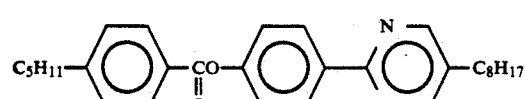 (232)
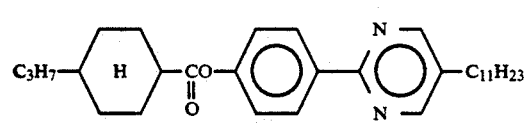 (233)
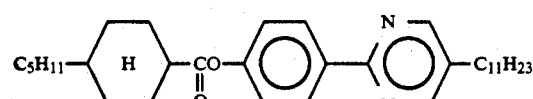 (234)
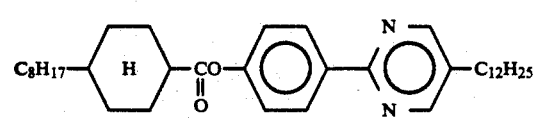 (235)
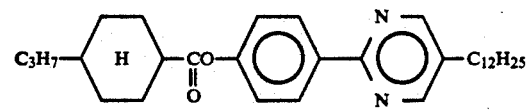 (236)
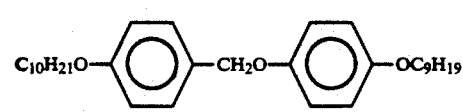 (237)
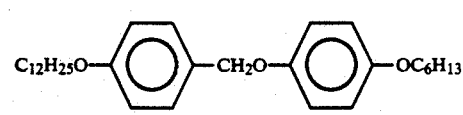 (238)

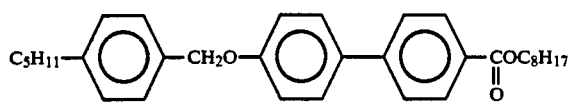

(239)

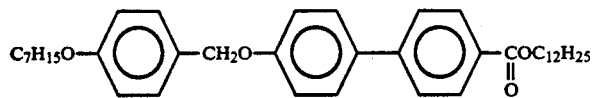

(240)

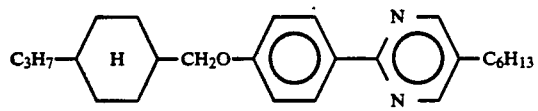

(241)

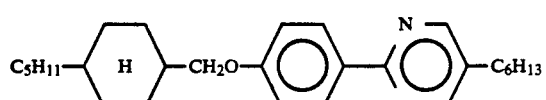

(242)

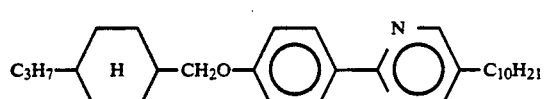

(243)

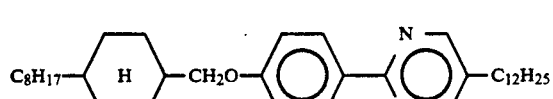

(244)

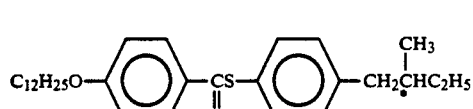

(245)

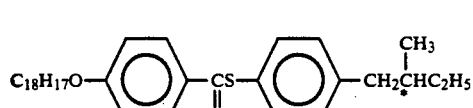

(246)

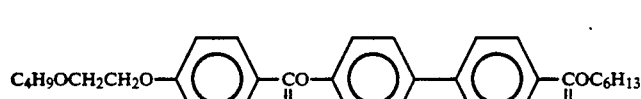

(247)

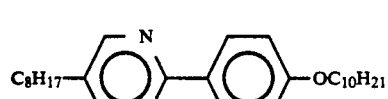

(248)

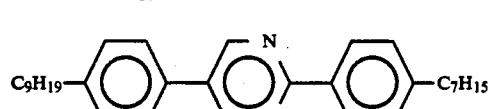

(249)

In formulating the liquid crystal composition according to the present invention, it is desirable to mix 1-500 wt. parts preferably 2-100 wt. parts, of a compound represented by the formula (I) with 100 wt. parts of at least one species of another mesomorphic compound as mentioned above or a liquid crystal composition containing another mesomorphic compound (hereinafter, simply referred to as "liquid crystal material").

Further, when two or more species of the compounds represented by the formulas (I) are used, the two or more species of the compound of the formula (I) may be used in a total amount of 1-500 wt. parts, preferably 2-100 wt. parts, per 100 wt. parts of the liquid crystal material.

The ferroelectric liquid crystal device according to the present invention may preferably be prepared by heating the liquid crystal composition prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the ferroelectric liquid crystal device prepared as described above for explanation of the structure thereof.

Referring to FIG. 1, the ferroelectric liquid crystal device includes a ferroelectric liquid crystal layer 1 disposed between a pair of glass substrates 2 each having thereon a transparent electrode 3 and an insulating alignment control layer 4. Lead wires 6 are connected to the electrodes so as to apply a driving voltage to the liquid crystal layer 1 from a power supply 7. Outside the substrates 2, a pair of polarizers 8 are disposed so as to modulate incident light $I_O$ form a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a selection of an organic insulating material or a precursor thereof in a concentration of 0.1 to 20 wt. %, preferably 0.2–10 wt. %, by spinner coating, dip coating, screen printing, spray coating or roller coating, followed by curing or hardening under prescribed hardening condition (e.g., by heating). The insulating alignment control layer may have a thickness of ordinarily 30 Å–1 micron, preferably 30–3000 Å, further preferably 50–1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a ferroelectric liquid crystal is sealed up to provide a ferroelectric liquid crystal layer 1 in a thickness of generally 0.5 to 20 microns, preferably 1 to 5 microns.

The ferroelectric liquid crystal provided by the composition of the present invention may desirably assume a SmC* phase (chiral smectic C phase) in a wide temperature range including room temperature (particularly, broad in a lower temperature side) and also shows a high-speed responsiveness, small temperature-dependence of response speed and wide drive voltage margin when contained in a device.

Particularly, in order to show a good alignment characteristic to form a uniform monodomain, the ferroelectric liquid crystal may show a phase transition series comprising isotropic phase —Ch phase (cholesteric phase)—SmA phase (smectic A phase)—SmC* phase (chiral smectic C phase) on temperature decrease.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

Figure 2:
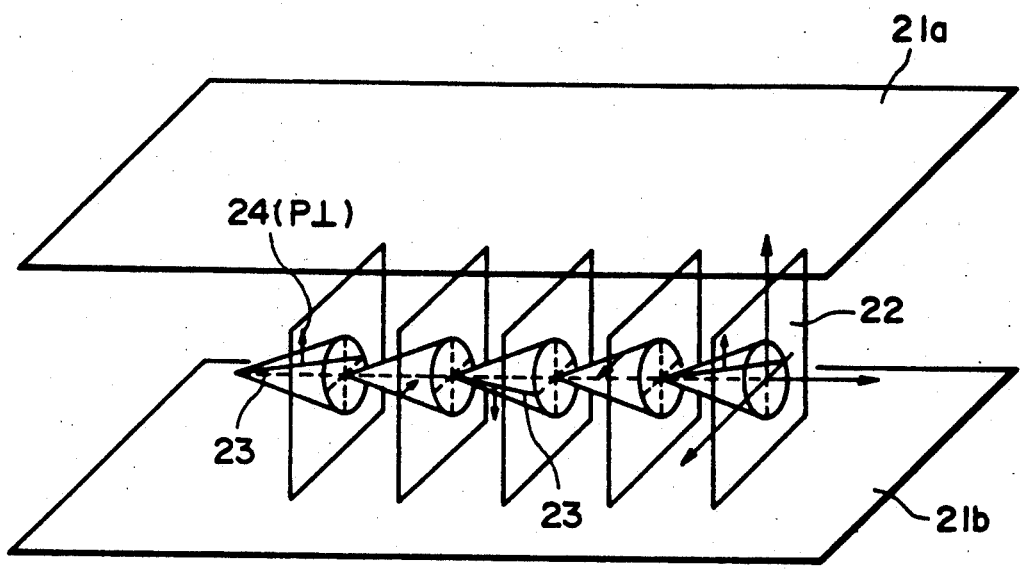
FIGS. 2 and 3 are schematic perspective views of a device cell embodiment for illustrating the operation principle of a ferroelectric liquid crystal device.

FIG. 2 is a schematic illustration of a ferroelectric liquid crystal cell (device) for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic H phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment (P) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments (P⊥) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
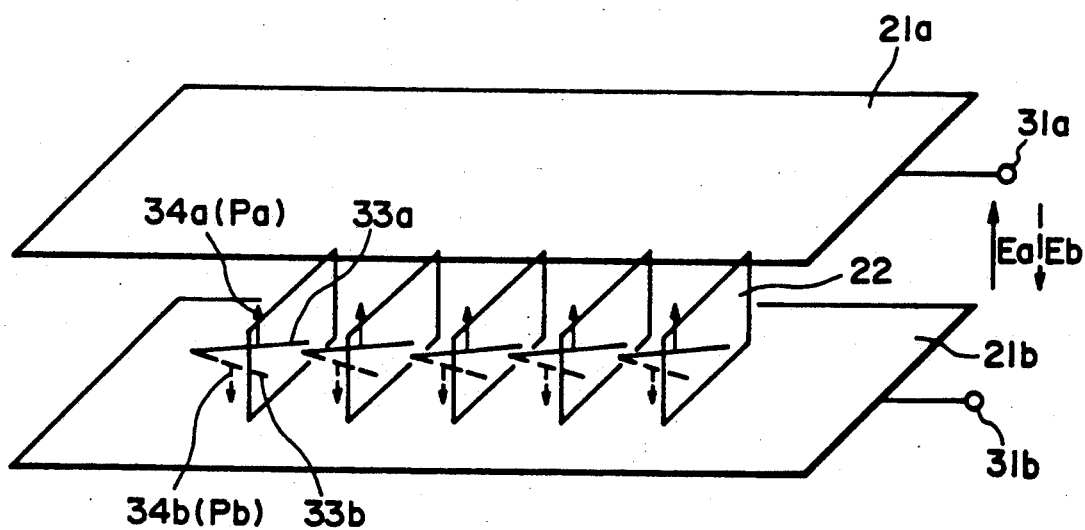

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics, the dipole moment is directed either in the upper direction 34a or in the lower direction 34b, depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

When such a ferroelectric liquid crystal device comprising a ferroelectric liquid crystal composition as described above between a pair of electrode plates is constituted as a simple matrix display device, the device may be driven by a driving method as disclosed in Japanese Laid-Open Patent Applications (KOKAI) Nos. 193426/1984, 193427/1984, 156046/1985, 156047/1985, etc.

Hereinbelow, the present invention will be explained more specifically with reference to examples. It is however to be understood that the present invention is not restricted to these examples.

EXAMPLE 1

2-(4-octylphenyl)-5-(trans-4-octylcyclohexyl)-benzoxazole (Example Compound No. 1-218) was synthesized through the following steps i)–iii). Step i) 3.00 g (10.4 mM) of 4-(trans-4-octylcyclohexyl)phenol was dispersed in a mixture solvent of 8.8 ml of benzene and 5.2 ml of acetic acid. To the dispersion, 1.2 ml of nitric acid (60%, density=1.38) was gradually added dropwise under cooling with iced water and stirring below 8° C. After the reaction, the reaction mixture was poured into water and extracted with ethyl acetate. The organic layer was dried with anhydrous sodium sulfate and subjected to reduced-pressure distillation into a solid. The solid was recrystallized from methanol to obtain 2.05 g of 2-nitro-4-(trans-4-octylcyclohexyl)-phenol (yield: 59.1%).

Step ii) In a 50 ml-three-necked flask, 1.90 g (5.70 mM) of 2-nitro-4-(trans-4-octylcyclohexyl)phenol, 0.35 g of activated carbon, 0.04 g of $FeCl_3 \cdot 6H_2O$ and 15 ml of ethanol were placed and heated to 55°–65° C. under stirring. To the mixture, 1.8 ml of 80% hydrazine hydrate was gradually added dropwise and heated to 70° C., followed by stirring for 20 min at 70° C. After the reaction, the reaction mixture was filtered under heating to remove the activated carbon and the filtrate was cooled to room temperature to precipitate a crystal. The crystal was recovered by filtration and recrystallized from ethanol to obtain 1.49 g of 2-amino-4-(trans-4-octylcyclohexyl)phenol (yield: 86.2%).

Step iii) In a 50 ml-round-bottomed flask, 10 g of polyphosphoric acid, 0.40 g (1.32 mM) of 2-amino-4-(trans-4-octylcyclohexyl)phenol and 0.31 g (1.32 mM) of 4-octylbenzoic acid were placed, followed by stirring for 4 hours at about 250 ° C. After the reaction, the reaction mixture was poured into water and an insoluble matter was recovered by filtration. The insoluble matter was added to 10% $K_2CO_3$ and sufficiently stirred, followed by recovery of a solid. The solid was washed with water and purified by silica gel column chromatography (eluent: toluene) to obtain 0.11 g of 2-(4-octylphenyl)-5-(trans-4-octylcyclohexyl)benzoxazole (yield: 16.7%).

Phase transition temperature (°C.)

$$\text{Cryst.} \underset{52.8}{\overset{77.8}{\rightleftarrows}} \text{SmC} \underset{100.7}{\overset{101.4}{\rightleftarrows}} \text{N} \underset{121.1}{\overset{121.8}{\rightleftarrows}} \text{Iso.}$$

Cryst.: crystal,
SmC: smectic C phase,
N: nematic phase, and
Iso.: isotropic phase.

EXAMPLE 2

2-(4-octylphenyl)-5-(4-decylphenyl)benzoxazole (Example Compound No. 1–60) was synthesized through the following steps i)–iv).

Step i) 5.00 g of 4-(4-decylphenyl)phenol was nitrated in the same manner as in Step i) of Example 1 to obtain 3.50 g of 2-nitro-4-(4-decylphenyl)phenol (yield: 61.1%

Step ii) 3.40 g of 2-nitro-4-(4-decylphenyl)phenol was reduced in the same manner as in Step ii) of Example 1 to obtain 2.42 g of 2-amino-4-(4-decylphenyl)phenol (yield: 77.7%).

Step iii) In a 50 ml-three-necked flask, 0.85 g (2.61 mM), 0.68 g of 4-octylbenzoyl chloride and 25 ml of dioxane were placed and heated. To the mixture, 0.94 ml of pyridine was gradually added dropwise at around 90° C. under stirring, followed by further stirring for 1 hour at around 90° C. After the reaction, the reaction mixture was poured into 150 ml of water to precipitate a crystal. The crystal was recovered by filtration and washed with methanol to obtain 1.34 g of 2-(4-octylbenzoylamino)-4-(4-decylphenyl)phenol (yield: 94.7%).

Step iv) In a 50 ml-round-bottomed flask, 1.30 g (2.40 mM) of 2-(4-octylbenzoylamino)-4-(4-decylphenyl)-phenol, 0.13 g (0.68 mM) of p-toluenesulfonic acid and 20 ml of o-dichlorobenzene were placed, followed by stirring for 40 min. at 189°–192° C. After the reaction, o-dichlorobenzene was distilled off under reduced pressure. The residue was purified by silica gel column chromatography (eluent: toluene) to obtain 0.62 g of 2-(4-octylphenyl)-5-(4-decylphenyl)benzoxazole (yield: 49.3%).

Phase transition temperature (°C.)

$$\text{Cryst.} \underset{69.6}{\overset{77.5}{\rightleftarrows}} \text{SmC} \underset{114.4}{\overset{114.9}{\rightleftarrows}} \text{N} \underset{123.2}{\overset{123.8}{\rightleftarrows}} \text{Iso.}$$

EXAMPLE 3

2-(4-decyloxyphenyl)-5-(4-decylphenyl)benzoxazole (Example Compound No. 1-133) was provided in a similar manner as in Example 2.

Phase transition temperature (°C.)

$$\text{Cryst.} \underset{70.3}{\overset{92.2}{\rightleftarrows}} \text{SmC} \underset{132.1}{\overset{132.8}{\rightleftarrows}} \text{SmA} \underset{135.2}{\overset{135.9}{\rightleftarrows}} \text{N} \underset{142.5}{\overset{143.4}{\rightleftarrows}} \text{Iso.}$$

SmA: smectic A phase

EXAMPLE 4

2-(4-octylphenyl)-5-(5-dodecylpyrimidine-2-yl)benzoxazole (Example Compound No. 1-253) was synthesized through the following steps i)–iii).

Step i) 2.00 g (5.87 mM) of 4-(5-dodecylpyrimidine-2-yl)phenol was dispersed in 20 ml of conc. sulfuric acid.

To the dispersion, 0.50 ml of nitric acid (60%, density=1.38) was gradually added dropwise under cooling and stirring at 2°-8° C. After the addition, the mixture was stirred for 30 min. at about 5° C. After the reaction, the reaction mixture was poured into 150 ml of iced water to precipitate a crystal. The crystal was recovered by filtration, washed with water and recrystallized from ethanol to obtain 1.85 g of 2-nitro-4-(5-dodecylpyrimidine-2-yl)phenol (yield:81.7%).

Step ii) 1.80 g of 2-nitro-4-(5-dodecylpyrimidine-2-yl)phenol was reduced in the same manner as in Step ii) of Example 1 to obtain 1.51 g of 2-amino-4-(5-dodecylpyrimidine-2-yl)phenol (yield: 91.0%).

Step iii) 2-(4-octylphenyl)-5-(5-dodecylpyrimidine-2-yl)benzoxazole was obtained in the same manner as in Step iii) and Step iv) of Example 2.

Phase transition temperature (°C.)

$$\text{Cryst.} \xrightarrow[60.8]{76.6} \text{SmC} \xrightarrow[98.5]{99.4} \text{N} \xrightarrow[127.4]{128.2} \text{Iso.}$$

EXAMPLE 5

A liquid crystal composition A was prepared by mixing the following compounds in respectively indicated proportions.

| Ex. Comp. No. | Structural formula | wt. parts |
|---|---|---|
| 20 | 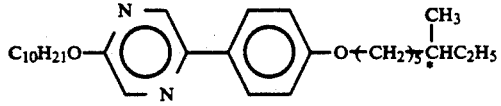 | 15 |
| 21 | 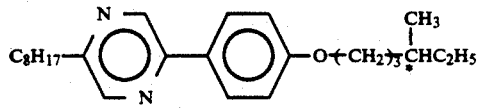 | 15 |
| 58 | 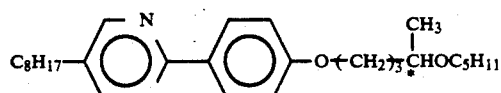 | 10 |
| 89 | 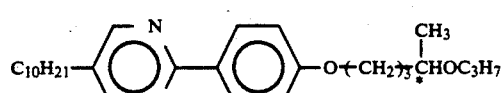 | 20 |
| 120 | 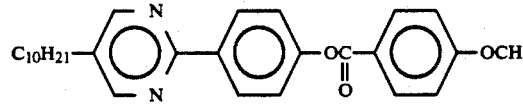 | 13 |
| 129 | 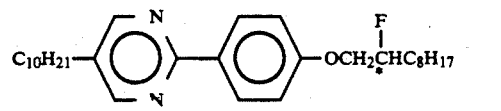 | 7 |
| 236 | 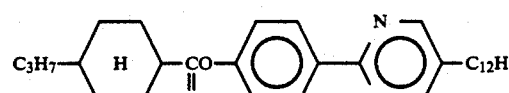 | 15 |
| 242 | 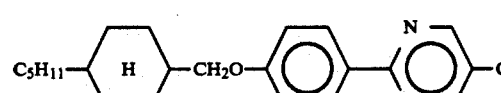 | 5 |

The liquid crystal composition A was further mixed with the following Example Compounds in the proportions respectively indicated below to provide a liquid crystal composition B.

| Ex. Comp. No. | Structural formula | wt. parts |
|---|---|---|
| 1-7 | 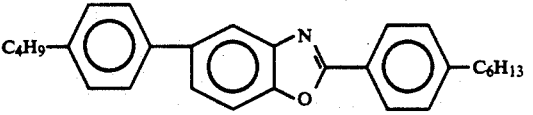 | 2 |

| Ex. Comp. No. | Structural formula | wt. parts |
| --- | --- | --- |
| 1-133 | $C_{10}H_{21}$—⟨phenyl⟩—⟨benzoxazole⟩—⟨phenyl⟩—$OC_{10}H_{21}$ | 4 |
| Composition A | | 94 |

Two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After alumina beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell. The cell gap was found to be about 2 microns as measured by a Berek compensator.

Then, the liquid crystal composition B was heated into an isotropic liquid, and injected into the above prepared cell under vacuum and, after sealing, was gradually cooled at a rate of 20° C./hour to 25° C. to prepare a ferroelectric liquid crystal device.

The ferroelectric liquid crystal device was subjected to measurement of an optical response time (time from voltage application until the transmittance change reaches 90% of the maximum under the application of a peak-to-peak voltage Vpp of 20 V in combination with right-angle cross-nicol polarizers).

The results are shown below.

| | 15° C. | 25° C. | 35° C. |
| --- | --- | --- | --- |
| Response time (μsec) | 131 | 90 | 75 |

COMPARATIVE EXAMPLE 1

A ferroelectric liquid crystal device was prepared in the same manner as in Example 5 except that the liquid crystal composition A prepared in Example 5 was injected into a cell. The measured values of the response time of the device were as follows.

| | 15° C. | 25° C. | 35° C. |
| --- | --- | --- | --- |
| Response time (μsec) | 155 | 100 | 80 |

EXAMPLE 6

A liquid crystal composition C was prepared in the same manner as in Example 5 except that the following Example Compounds were used instead of Example Compounds Nos. 1-7 and 1-133 in respectively indicated proportions.

| Ex. Comp. No. | Structural formula | wt. parts |
| --- | --- | --- |
| 1-75 | $C_4H_9$—⟨phenyl⟩—⟨benzoxazole⟩—⟨phenyl⟩—$OC_6H_{13}$ | 2 |
| 1-161 | $C_8H_{17}O$—⟨phenyl⟩—⟨benzoxazole⟩—⟨phenyl⟩—$OC_6H_{13}$ | 3 |
| 1-174 | $C_8H_{17}$—⟨phenyl⟩—⟨benzoxazole⟩—⟨phenyl⟩—$OCH_2\overset{*}{C}HC_4H_9$ (F) | 2 |
| Composition A | | 93 |

A ferroelectric liquid crystal device was prepared in the same manner as in Example 5 except for using the liquid crystal composition C, and subjected to measurement of response time in the same manner as in EXAMPLE 5, whereby the following results were obtained.

|  | 15° C. | 25° C. | 35° C. |
|---|---|---|---|
| Response time (μsec) | 133 | 92 | 78 |

|  | 15° C. | 25° C. | 35° C. |
|---|---|---|---|
| Response time (μsec) | 115 | 78 | 66 |

EXAMPLE 7

A liquid crystal composition D was prepared in the same manner as in Example 5 except that the following Example Compounds were used instead of Example Compounds Nos. 1-7 and 1-133 in respectively indicated proportions.

| Ex. Comp. No. | Structural formula | wt. parts |
|---|---|---|
| 1-15 | $C_5H_{11}$—〇—[benzoxazole]—〇—$C_6H_{13}$ | 3 |
| 1-177 | $C_6H_{13}$—〇—[benzoxazole]—〇—O(CH$_2$)$_2$CH(CH$_3$)OC$_3$H$_7$ | 2 |
| 1-218 | $C_8H_{17}$—[H]—[benzoxazole]—〇—$C_8H_{17}$ | 4 |
| 1-245 | $C_7H_{15}$—[pyrimidine]—[benzoxazole]—〇—$C_8H_{17}$ | 3 |
| Composition A | | 88 |

EXAMPLE 8

A liquid crystal composition E was prepared in the same manner as in Example 5 except that the following Example Compounds were used instead of Example Compounds Nos. 1-7 and 1-133 in respectively indicated proportions.

| Ex. Comp. No. | Structural formula | wt. parts |
|---|---|---|
| 1-60 | $C_{10}H_{21}$—〇—[benzoxazole]—〇—$C_8H_{17}$ | 2 |
| 1-84 | $C_5H_{11}$—〇—[benzoxazole]—〇—$OC_6H_{13}$ | 4 |
| 1-210 | $C_6H_{13}$—[H]—[benzoxazole]—〇—$C_8H_{17}$ | 3 |
| Composition A | | 91 |

A ferroelectric liquid crystal device was prepared in the same manner as in Example 5 except for using the liquid crystal composition D, and subjected to measurement of response time in the same manner as in Example 5, whereby the following results were obtained.

A ferroelectric liquid crystal device was prepared in the same manner as in Example 5 except for using the liquid crystal composition E, and subjected to measurement of response time in the same manner as in Example 5, whereby the following results were obtained.

| | 15° C. | 25° C. | 35° C. |
|---|---|---|---|
| Response time (μsec) | 127 | 88 | 72 |

EXAMPLE 9

A liquid crystal composition F was prepared in the same manner as in Example 5 except that the following Example Compounds were used instead of Compounds Nos. 1-7 and 1-133 in respectively indicated proporations.

| Ex. Comp. No. | Structural formula | wt. parts |
|---|---|---|
| 1-166 | $C_8H_{17}$—〇—[benzoxazole]—〇(F)—$OC_6H_{13}$ | 5 |
| 1-182 | $C_5H_{11}OC(=O)$—〇—[benzoxazole]—〇—$C_6H_{13}$ | 2 |
| 1-253 | $C_{12}H_{25}$—[pyrazine]—[benzoxazole]—〇—$C_8H_{17}$ | 3 |
| Composition A | | 90 |

A ferroelectric liquid crystal device was prepared in the same manner as in Example 5 except for using the liquid crystal composition F, and subjected to measurement of response time in the same manner as in Example 5, whereby the following results were obtained.

| | 15° C. | 25° C. | 35° C. |
|---|---|---|---|
| Response time (μsec) | 135 | 87 | 71 |

EXAMPLE 10

A liquid crystal composition G was prepared in the same manner as in Example 5 except that the following Example Compounds were used instead of Example Compounds Nos. 1-7 and 1-133 in respectively indicated proportions.

| Ex. Comp. No. | Structural formula | wt. parts |
|---|---|---|
| 1-83 | $C_5H_{11}$—〇—[benzoxazole]—〇—$OC_5H_{11}$ | 4 |
| 1-264 | $C_5H_{11}$—[H]—[benzoxazole]—〇—$OC_8H_{17}$ | 3 |
| 1-268 | $C_8H_{17}$—[thiadiazole]—[benzoxazole]—〇—$OCH_2\overset{*}{C}HC_4H_9$ (F) | 2 |
| Composition A | | 91 |

A ferroelectric liquid crystal device was prepared in the same manner as in Example 5 except for using the liquid crystal composition G, and subjected to measurement of response time in the same manner as in Example 5, whereby the following results were obtained.

| | 15° C. | 25° C. | 35° C. |
|---|---|---|---|
| Response time (μsec) | 134 | 91 | 72 |

EXAMPLE 11

A liquid crystal composition H was prepared by mixing the following compounds in respectively indicated proportions.

| Ex. Comp. No. | Structural formula | wt. parts |
|---|---|---|
| 8 | $C_8H_{17}O$-⬡-$OC$(=O)-⬡-⬡-$CH_2\overset{*}{C}H(CH_3)C_2H_5$ | 16 |
| 9 | $C_8H_{17}O$-⬡-$CS$(=O)-⬡-$CH_2\overset{*}{C}H(CH_3)C_2H_5$ | 22.5 |
| 18 | $C_8H_{17}O$-⬡-$CO$(=O)-⬡-$OCH_2\overset{*}{C}H(CH_3)C_2H_5$ | 64 |
| 23 | $C_8H_{17}$-(pyrimidine)-⬡-$O(CH_2)_3\overset{*}{C}H(CH_3)C_2H_5$ | 10 |
| 24 | $C_{11}H_{23}O$-(pyrimidine)-⬡-$O(CH_2)_2\overset{*}{C}H(CH_3)C_2H_5$ | 10 |
| 43 | $C_{10}H_{21}O$-⬡-$CS$(=O)-⬡-$OCH_2\overset{*}{C}H(CH_3)C_2H_5$ | 22.5 |
| 63 | $C_{10}H_{21}OC$(=O)-⬡-⬡-$OC$(=O)-⬡-$OCH_2\overset{*}{C}H(CH_3)OC_5H_{11}$ | 15 |
| 87 | $C_6H_{13}OC$(=O)-⬡-⬡-$OC$(=O)-⬡-$OCH_2\overset{*}{C}H(CH_3)OC_8H_{17}$ | 15 |
| 124 | $C_{12}H_{25}O$-⬡-$CO$(=O)-⬡-$OCH_2\overset{*}{C}H(F)C_6H_{13}$ | 6.75 |
| 136 | $C_8H_{17}O$-⬡-$CO$(=O)-⬡-$OCH_2\overset{*}{C}H(F)C_5H_{11}$ | 18.75 |
| 236 | $C_3H_7$-(H cyclohexyl)-$CO$(=O)-⬡-(pyrimidine)-$C_{12}H_{25}$ | 20 |

The liquid crystal composition H was further mixed with the following Example Compounds in the proportions respectively indicated below to provide a liquid crystal composition I.

| Ex. Comp. No. | Structural formula | wt. parts |
|---|---|---|
| 1-15 | $C_5H_{11}$—〈phenyl〉—〈benzoxazole N,O〉—〈phenyl〉—$C_6H_{13}$ | 2 |
| 1-17 | $C_5H_{11}$—〈phenyl〉—〈benzoxazole N,O〉—〈phenyl〉—$C_8H_{17}$ | 2 |
| 1-221 | $C_8H_{17}$—〈H (cyclohexyl)〉—〈benzoxazole N,O〉—〈phenyl〉—$OCH_2\overset{*}{C}HC_4H_9$ with F on the chiral carbon | 4 |
| Composition H | | 92 |

A ferroelectric liquid crystal device was prepared in the same manner as in Example 5 except for using the composition I. In the ferroelectric liquid crystal device, a monodomain with a good and uniform alignment characteristic was observed. The ferroelectric liquid crystal device was subjected to measurement of response time and observation of a switching state, etc. in the same manner as in Example 5, whereby the following results were obtained.

|  | 15° C. | 25° C. | 35° C. |
|---|---|---|---|
| Response time (μsec) | 450 | 270 | 195 |

EXAMPLE 12

A liquid crystal composition J was prepared in the same manner as in Example 11 except that the following Example Compounds were used instead of Example Compounds Nos. 1-15, 1-17 and 1-221 in respectively indicated proportions.

| Ex. Comp. No. | Structural formula | wt. parts |
|---|---|---|
| 1-87 | $C_5H_{11}$—〈phenyl〉—〈benzoxazole N,O〉—〈phenyl〉—$OC_9H_{19}$ | 3 |
| 1-163 | $C_{10}H_{21}O$—〈phenyl〉—〈benzoxazole N,O〉—〈phenyl〉—$OC_5H_{11}$ | 2 |
| 1-263 | $C_7H_{15}$—〈phenyl〉—〈benzoxazole N,O〉—〈thiophene S〉—$C_{12}H_{25}$ | 3 |
| Composition H | | 92 |

| Response time (μsec) | 344 | 215 | 163 |
|---|---|---|---|

COMPARATIVE EXAMPLE 2

A ferroelectric liquid crystal device was prepared in the same manner as in Example 5 except that the liquid crystal composition H prepared in Example 11 was injected into a cell. The measured values of the response time of the device were as follows.

A ferroelectric liquid crystal device was prepared in the same manner as in Example 5 except for using the composition J. In the ferroelectric liquid crystal device, a monodomain with a good and uniform alignment characteristic was observed. The ferroelectric liquid crystal device was subjected to measurement of response time and observation of a switching state, etc. in the same manner as in Example 5, whereby the following results were obtained.

|  | 15° C. | 25° C. | 35° C. |
|---|---|---|---|
| Response time (μsec) | 370 | 231 | 173 |

Further, when the device was driven, a clear switching action was observed, and good bistability was shown after the termination of the voltage application.

EXAMPLE 13

A liquid crystal composition K was prepared in the same manner as in Example 11 except that the following Example Compounds were used instead of Example Compounds Nos. 1-15, 1-17 and 1-221 in respectively indicated proportions.

| Ex. Comp. No. | Structural formula | wt. parts |
|---|---|---|
| 1-173 | $C_6H_{13}$—⌬—⌬(N,O benzoxazole)—⌬—O(CH$_2$)$_2$CH(CH$_3$)C$_2$H$_5$ | 3 |
| 1-179 | $C_8H_{17}$—⌬—⌬(N,O benzoxazole)—⌬(CF$_3$)—OC$_6$H$_{13}$ | 4 |
| 1-184 | $C_6H_{13}$—⌬—⌬(N,O benzoxazole)—⌬—C(=O)CF(*)C$_6$H$_{13}$ | 2 |
| Composition H | | 91 |

A ferroelectric liquid crystal device was prepared in the same manner as in Example 5 except for using the composition K. In the ferroelectric liquid crystal device, a monodomain with a good and uniform alignment characteristic was observed. The ferroelectric liquid crystal device was subjected to measurement of response time and observation of a switching state, etc. in the same manner as in Example 5, whereby the following results were obtained.

|  | 15° C. | 25° C. | 35° C. |
|---|---|---|---|
| Response time (μsec) | 351 | 223 | 170 |

Further, when the device was driven, a clear switching action was observed, and good bistability was shown after the termination of the voltage application.

EXAMPLE 14

A liquid crystal composition L was prepared in the same manner as in Example 11 except that the following Example Compounds were used instead of Example Compounds Nos. 1-15, 1-17 and 1-221 in respectively indicated proportions.

| Ex. Comp. No. | Structural formula | wt. parts |
|---|---|---|
| 1-23 | $C_6H_{13}$—⌬—⌬(N,O benzoxazole)—⌬—$C_6H_{13}$ | 3 |
| 1-76 | $C_4H_9$—⌬—⌬(N,O benzoxazole)—⌬—OC$_7$H$_{15}$ | 3 |
| 1-176 | $C_7H_{15}$O—⌬—⌬(N,O benzoxazole)—⌬—OCH$_2$CF(*)C$_6$H$_{13}$ | 3 |
| Composition H | | 91 |

A ferroelectric liquid crystal device was prepared in the same manner as in Example 5 except for using the composition L. In the ferroelectric liquid crystal device, a monodomain with a good and uniform alignment characteristic was observed. The ferroelectric liquid crystal device was subjected to measurement of response time and observation of a switching state, etc. in the same manner as in Example 5, whereby the following results were obtained.

|  | 15° C. | 25° C. | 35° C. |
|---|---|---|---|
| Response time (μsec) | 340 | 219 | 170 |

Further, when the device was driven, a clear switching action was observed, and good bistability was shown after the termination of the voltage application.

EXAMPLE 15

A liquid crystal composition M was prepared in the same manner as in Example 11 except that the following Example Compounds were used instead of Example Compounds Nos. 1-15, 1-17 and 1-221 in respectively indicated proportions.

| Ex. Comp. No. | Structural formula | wt. parts |
|---|---|---|
| 1-272 | $C_{10}H_{21}$—〇—〇(N,O)—〇—$C_3H_7$ | 4 |
| 1-284 | $C_8H_{17}$—〈H〉—〇(N,O)—〈H〉—$C_8H_{17}$ | 3 |
| 1-260 | $C_5H_{11}$—(N=N,S)—〇(N,O)—〇—$OC_7H_{15}$ | 3 |
| Composition H | | 90 | sponse time and observation of a switching state, etc. in the same manner as in Example 5, whereby the following results were obtained.

|  | 15° C. | 25° C. | 35° C. |
|---|---|---|---|
| Response time (μsec) | 352 | 220 | 170 |

Further, when the device was driven, a clear switching action was observed, and good bistability was shown after the termination of the voltage application.

EXAMPLE 16

A liquid crystal composition N was prepared in the same manner as in Example 11 except that the following Example Compounds were used instead of Compounds Nos. 1-15, 1-17 and 1-221 in respectively indicated proportions.

| Ex. Comp. No. | Structural formula | wt. parts |
|---|---|---|
| 1-11 | $C_4H_9$—〇—〇(N,O)—〇—$C_{10}H_{21}$ | 2 |
| 1-193 | $C_2H_5\underset{*}{C}HCH_2$— (with $CH_3$) —〇—〇(N,O)—〇—$OC_8H_{17}$ | 3 |
| 1-249 | $C_6H_{13}\underset{*}{C}HCH_2O$— (with F) —(N,N)—〇(N,O)—〇—$C_8H_{17}$ | 4 |
| Composition H | | 91 |

A ferroelectric liquid crystal device was prepared in the same manner as in Example 5 except for using the composition M. In the ferroelectric liquid crystal device, a monodomain with a good and uniform alignment characteristic was observed. The ferroelectric liquid crystal device was subjected to measurement of re- A ferroelectric liquid crystal device was prepared in the same manner as in Example 5 except for using the composition N. In the ferroelectric liquid crystal device, a monodomain with a good and uniform alignment characteristic was observed. The ferroelectric liquid crystal device was subjected to measurement of response time and observation of a switching state, etc. in the same manner as in Example 5, whereby the following results were obtained.

|  | 15° C. | 25° C. | 35° C. |
|---|---|---|---|
| Response time (μsec) | 341 | 210 | 161 |

Further, when the device was driven, a clear switching action was observed, and good bistability was shown after the termination of the voltage application.

EXAMPLE 17

A liquid crystal composition 0 was prepared in the same manner as in Example 11 except that the following Example Compounds were used instead of Example Compounds Nos. 1-15, 1-17 and 1-221 in respectively indicated proportions.

| Ex. Comp. No. | Structural formula | wt. parts |
|---|---|---|
| 1-35 | $C_7H_{15}$—⟨◯⟩—⟨◯⟩—⟨◯⟩—$C_9H_{19}$ (benzoxazole) | 3 |
| 1-130 | $C_{10}H_{21}$—⟨◯⟩—⟨◯⟩—⟨◯⟩—$OC_7H_{15}$ (benzoxazole) | 5 |
| 1-280 | $CH_3$ \| $C_2H_5CHCH_2$—⟨◯⟩—⟨◯⟩—⟨H⟩—$C_7H_{15}$ (benzoxazole) | 2 |
| Composition H | | 90 |

A ferroelectric liquid crystal device was prepared in the same manner as in Example 5 except for using the composition 0. In the ferroelectric liquid crystal device, a monodomain with a good and uniform alignment characteristic was observed. The ferroelectric liquid crystal device was subjected to measurement of response time and observation of a switching state, etc. in the same manner as in Example 5, whereby the following results were obtained.

|  | 15° C. | 25° C. | 35° C. |
|---|---|---|---|
| Response time (μsec) | 360 | 228 | 173 |

Further, when the device was driven, a clear switching action was observed, and good bistability was shown after the termination of the voltage application.

EXAMPLES 18-21

Liquid crystal compositions P to S were prepared by replacing the Example Compounds and the liquid crystal compositions used in Example 5 with Example Compounds and liquid crystal compositions shown in the following Table 1. Ferroelectric liquid crystal devices were prepared in the same manner as in Example 5 by respectively using these compositions instead of the composition B, and subjected to measurement of optical response time and observation of switching states. In the devices, a monodomain with a good and uniform alignment characteristic was observed. The results of the measurement are shown in the following Table 1.

TABLE 1

| Ex. No. (Comp. Name) | Example Compound No. or liquid crystal composition name (weight parts) | | | | | Response time (μsec) | | |
|---|---|---|---|---|---|---|---|---|
| | | | | | | 15° C. | 25° C. | 35° C. |
| 18 (P) | 1-171 (3) | 1-181 (3) | 1-288 (2) | | A (92) | 128 | 85 | 70 |
| 19 (Q) | 1-5 (3) | 1-221 (2) | 1-259 (3) | 1-265 (3) | A (89) | 115 | 79 | 66 |
| 20 (R) | 1-121 (5) | 1-162 (2) | 1-261 (3) | | H (90) | 351 | 225 | 172 |
| 21 (S) | 1-114 (2) | 1-256 (2) | 1-266 (3) | 1-282 (2) | H (91) | 338 | 221 | 180 |

As is apparent from the results shown in the above Examples 18-21, the ferroelectric liquid crystal devices containing the liquid crystal compositions P to S showed an improved low-temperature operation characteristic, a high-speed responsiveness, and a decreased temperature dependence of the response speed.

EXAMPLE 22

A blank cell was prepared in the same manner as in Example 5 by using a 2% aqueous solution of polyvinyl alcohol resin (PVA-117, available from Kuraray K.K.) instead of the 1.5%-solution of polyimide resin precursor in dimethylacetoamide on each electrode plate. A ferroelectric liquid crystal device was prepared by filling the blank cell with the liquid crystal composition B prepared in Example 5. The liquid crystal device was subjected to measurement of optical response time in the same manner as in Example 5. The results are shown below.

|  | 15° C. | 25° C. | 35° C. |
|---|---|---|---|
| Response time (μsec) | 125 | 82 | 73 |

EXAMPLE 23

A blank cell was prepared in the same manner as in Example 5 except for omitting the SiO$_2$ layer to form an alignment control layer composed of the polyimide resin layer alone on each electrode plate. A ferroelectric liquid crystal device was prepared by filling the blank cell with the liquid crystal composition B prepared in Example 5. The liquid crystal device was subjected to measurement of optical response time in the same manner as in Example 5. The results are shown below.

|  | 15° C. | 25° C. | 35° C. |
|---|---|---|---|
| Response time (μsec) | 121 | 79 | 70 |

As is apparent from the above Examples 22 and 23, also in the cases of different device structures, the devices containing the ferroelectric liquid crystal composition B according to the present invention respectively provided a remarkably improved operation characteristic at a lower temperature and also a decreased temperature-dependence of the response speed.

EXAMPLE 24

A liquid crystal composition T was prepared by mixing the following compounds in respectively indicated proportions.

| Ex. Comp. No. | Structural formula | wt. parts |
|---|---|---|
| 9 | 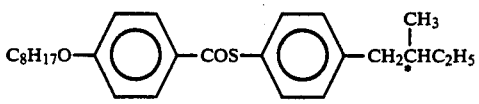 | 18 |
| 245 | 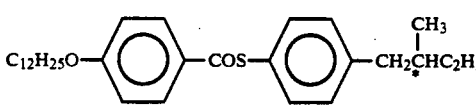 | 18 |
| 246 | 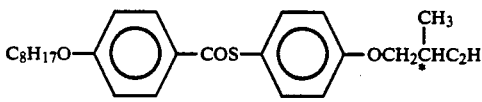 | 8 |
| 43 | 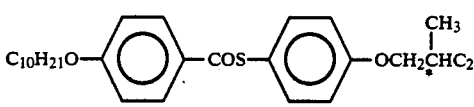 | 8 |
| 87 | 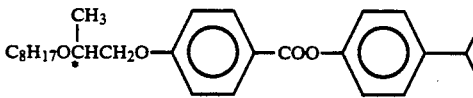 | 12 |
| 247 | 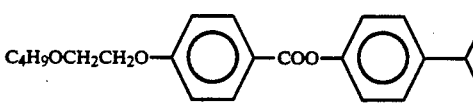 | 12 |
| 63 | 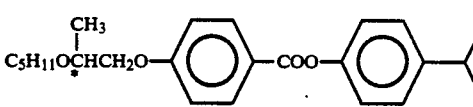 | 6 |
| 171 | 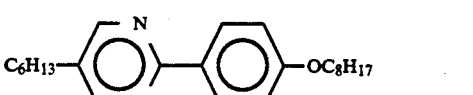 | 6 |
| 248 | 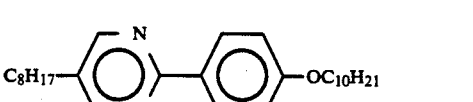 | 6 |

-continued

| Ex. Comp. No. | Structural formula | wt. parts |
|---|---|---|
| 191 | C$_5$H$_{11}$–[pyridazine]–[phenyl]–[phenyl]–C$_6$H$_{13}$ | 4 |
| 249 | C$_9$H$_{19}$–[phenyl]–[pyrimidine]–[phenyl]–C$_7$H$_{15}$ | 2 |

The liquid crystal composition T was further mixed with the following Example Compounds in the proportions respectively indicated below to provide a liquid crystal composition U.

| Ex. Comp. No. | Structural formula | wt. parts |
|---|---|---|
| 1-25 | C$_6$H$_{13}$–[phenyl]–[benzoxazole]–[phenyl]–C$_8$H$_{17}$ | 3 |
| 1-109 | C$_8$H$_{17}$–[phenyl]–[benzoxazole]–[phenyl]–OC$_4$H$_9$ | 3 |
| 1-128 | C$_{10}$H$_{21}$–[phenyl]–[benzoxazole]–[phenyl]–OC$_5$H$_{11}$ | 2 |
| Composition T | | 92 |

A ferroelectric liquid crystal device was prepared in the same manner as in Example 5 except for using the composition U. In the ferroelectric liquid crystal device, a monodomain with a good and uniform alignment characteristic was observed. The ferroelectric liquid crystal device was subjected to measurement of response time and observation of a switching state, etc. in the same manner as in Example 5, whereby the following results were obtained.

| | 15° C. | 25° C. | 35° C. |
|---|---|---|---|
| Response time (μsec) | 978 | 433 | 215 |

COMPARATIVE EXAMPLE 3

A ferroelectric liquid crystal device was prepared in the same manner as in Example 5 except that the liquid crystal composition T prepared in Example 24 was injected into a cell. The measured values of the response time of the device were as follows.

| | 15° C. | 25° C. | 35° C. |
|---|---|---|---|
| Response time (μsec) | 1260 | 535 | 245 |

EXAMPLE 25

A liquid crystal composition V was prepared in the same manner as in Example 24 except that the following Example Compounds were used instead of Example Compounds Nos. 1-25, 1-109 and 1-128 in respectively indicated proportions.

| Ex. Comp. No. | Structural formula | wt. parts |
|---|---|---|
| 1-45 | C$_8$H$_{17}$–[phenyl]–[benzoxazole]–[phenyl]–C$_{10}$H$_{21}$ | 3 |

-continued

| Ex. Comp. No. | Structural formula | wt. parts |
|---|---|---|
| 1-166 | C$_8$H$_{17}$–⟨phenyl⟩–⟨benzoxazole⟩–⟨phenyl(F)⟩–OC$_6$H$_{13}$ | 4 |
| 1-230 | C$_5$H$_{11}$–⟨cyclohexyl(H)⟩–⟨benzoxazole⟩–⟨phenyl⟩–OC$_5$H$_{11}$ | 2 |
| Composition T | | 91 |

A ferroelectric liquid crystal device was prepared in the same manner as in Example 5 except for using the composition V. In the ferroelectric liquid crystal device, a monodomain with a good and uniform alignment characteristic was observed. The ferroelectric liquid crystal device was subjected to measurement of response time and observation of a switching state, etc. in the same manner as in Example 5, whereby the following results were obtained.

|  | 15° C. | 25° C. | 35° C. |
|---|---|---|---|
| Response time (μsec) | 929 | 403 | 197 |

Further, when the device was driven, a clear switching action was observed, and good bistability was shown after the termination of the voltage application.

EXAMPLE 26

A liquid crystal composition W was prepared in the same manner as in Example 24 except that the following Example Compounds were used instead of Example Compounds Nos. 1-25, 1-109 and 1-128 in respectively indicated proportions.

sponse time and observation of a switching state, etc. in the same manner as in Example 5, whereby the following results were obtained.

|  | 15° C. | 25° C. | 35° C. |
|---|---|---|---|
| Response time (μsec) | 1024 | 457 | 228 |

Further, when the device was driven, a clear switching action was observed, and good bistability was shown after the termination of the voltage application.

EXAMPLE 27

2-(trans-4-pentylcyclohexyl)-5-(4-decylphenyl)benzoxazole (Example Compound No. 1-278) was synthesized through the following steps i) and ii).

Step i) In a 50 ml-three-necked flask, 0.70 g (2.15 mM) of 2-amino-4-(4-decylphenyl)phenol, 0.48 g (2.21 mM) of trans-4-pentylcyclohexylcarbonyl chloride and 20 ml of dioxane were placed. To the mixture, 0.77 ml of pyridine was gradually added dropwise at about 87° C. under stirring, followed by heat-stirring for 1.5 hours at about 87° C. After the reaction, the reaction mixture was poured into 150 ml of water to precipitate a crystal.

| Ex. Comp. No. | Structural formula | wt. parts |
|---|---|---|
| 1-31 | C$_7$H$_{15}$–⟨phenyl⟩–⟨benzoxazole⟩–⟨phenyl⟩–C$_5$H$_{11}$ | 3 |
| 1-156 | C$_6$H$_{13}$O–⟨phenyl⟩–⟨benzoxazole⟩–⟨phenyl⟩–C$_{10}$H$_{21}$ | 2 |
| 1-246 | C$_8$H$_{17}$–⟨pyrazine⟩–⟨benzoxazole⟩–⟨phenyl⟩–C$_5$H$_{11}$ | 2 |
| Composition T | | 93 |

A ferroelectric liquid crystal device was prepared in the same manner as in Example 5 except for using the composition W. In the ferroelectric liquid crystal device, a monodomain with a good and uniform alignment characteristic was observed. The ferroelectric liquid crystal device was subjected to measurement of re- The crystal was recovered by filtration, washed with methanol and recrystallized from toluene to obtain 0.61 g of 2-(trans-4-pentylcyclohexylcarbonylamino)-4-(4-decylphenyl)phenol (yield: 56.1%).

Step ii) In a 30 ml-round-bottomed flask, 0.60 g (1.19 mM) of 2-(trans-4-pentylcyclohexylcarbonylamino)-4-(4decylphenyl)phenol, 0.07 g (0.37 mM) of p-toluenesulfonic acid and 10 ml of o-dichlorobenzene were placed, followed by stirring for 40 min. at 188°-192° C. After the reaction, o-dichlorobenzene was distilled-off under reduced pressure. The residue was purified by silica gel column chromatography (eluent: toluene) to obtain 0.28 g of 2-(trans-4-pentylcyclohexyl)-5-(4-decylphenyl)benzoxazole (yield: 48.4%).

Phase transition temperature (°C.)

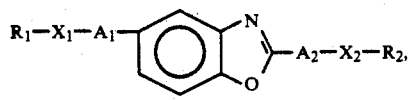

As described above, according to the present invention, there are provided a ferroelectric liquid crystal composition and a ferroelectric liquid crystal device containing the composition, which shows a good switching characteristic, an improved low-temperature operation characteristic and a decreased temperature-dependence of response speed.

What is claimed is:

1. A liquid crystal composition comprising at least two mesomorphic compounds, at least one of which is a mesomorphic compound having the following formula (I):

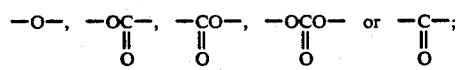

wherein $R_1$ and $R_2$ each is an alkyl group having 1-16 carbon atoms optionally substituted with fluoro or alkoxy group having 2-6 carbon atoms; $X_1$ and $X_2$ each is a single bond, $$-O-, \quad -OC-, \quad -CO-, \quad -OCO- \text{ or } -C-;$$
$$\quad\quad\quad \overset{\|}{O} \quad\quad \overset{\|}{O} \quad\quad \overset{\|}{O} \quad\quad\quad \overset{\|}{O}$$

and $A_1$ is

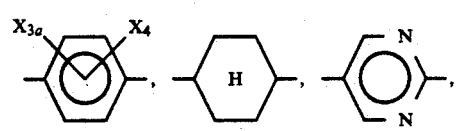

wherein $X_3a$ and $X_4a$ each is hydrogen or fluorine and Z is —O— or —S—; and $A_2$ is

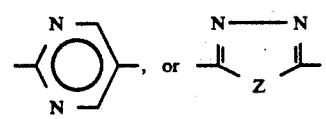

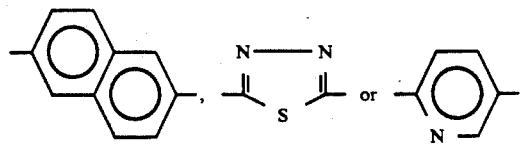

wherein $X_{3b}$ and $X_{4b}$ each is hydrogen, fluorine, chlorine, bromine, —CH$_3$, —CN or —CF$_3$.

2. A composition according to claim 1, wherein $X_1$ is any one of a single bond, $$-O- \text{ and } -CO-;$$
$$\quad\quad\quad\quad \overset{\|}{O}$$

$X_2$ is any one of a single bond, $$-O-, \quad -OC- \text{ and } -CO-;$$
$$\quad\quad \overset{\|}{O} \quad\quad\quad \overset{\|}{O}$$

and $R_1$ and $R_2$ are respectively any one of groups (i) to (iv) shown below:

(i) n-alkyl group having 1-16 carbon atoms;

(ii)

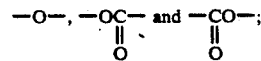

wherein m is 1-6 and n is 2-8 (optically active or inactive);

(iii)

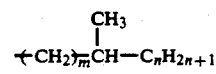

wherein r is 0-6, s is 0 or 1 and t is 1-12 (optically active or inactive); and (iv)

wherein x is 1-14.

3. A composition according to claim 1, wherein said at least one mesomorphic compound has the formula:

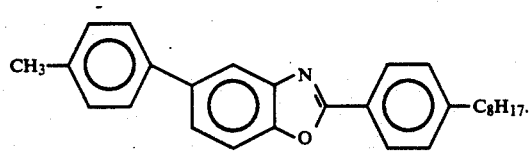

4. A composition according to claim 1, wherein said at least one mesomorphic compound has the formula:

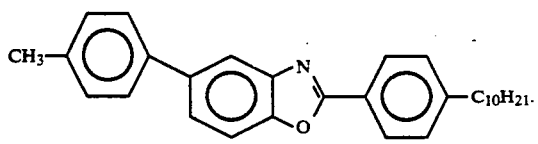

5. A composition according to claim 1, wherein said at least one mesomorphic compound has the formula:

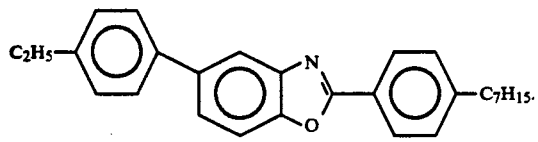

6. A composition according to claim 1, wherein said at least one mesomorphic compound has the formula:

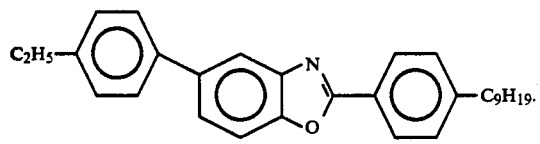

7. A composition according to claim 1, wherein said at least one mesomorphic compound has the formula:

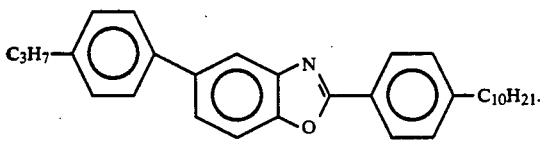

8. A composition according to claim 1, wherein said at least one mesomorphic compound has the formula:

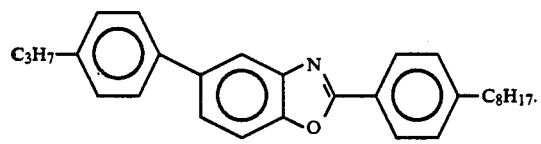

9. A composition according to claim 1, wherein said at least one mesomorphic compound has the formula:

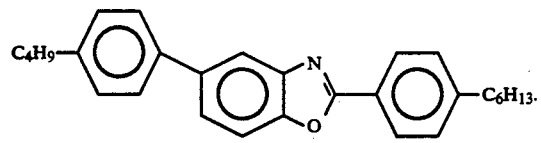

10. A composition according to claim 1, wherein said at least one mesomorphic compound has the formula:

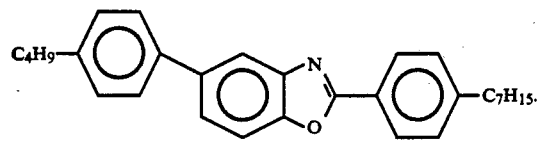

11. A composition according to claim 1, wherein said at least one mesomorphic compound has the formula:

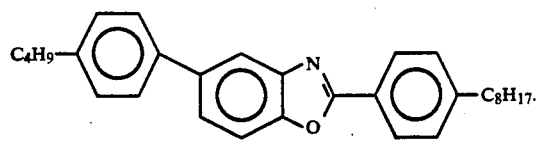

12. A composition according to claim 1, wherein said at least one mesomorphic compound has the formula:

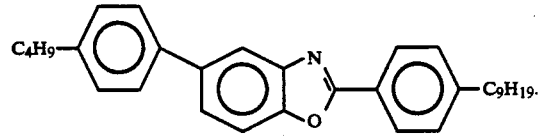

13. A composition according to claim 1, wherein said at least one mesomorphic compound has the formula:

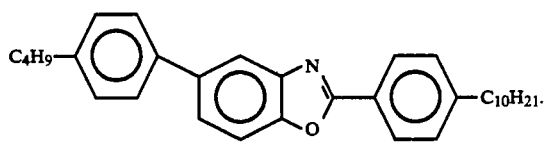

14. A composition according to claim 1, wherein said at least one mesomorphic compound has the formula:

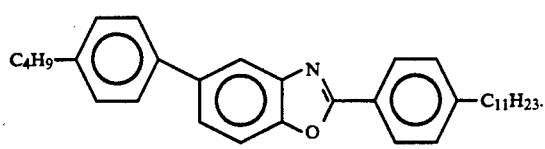

15. A composition according to claim 1, wherein said at least one mesomorphic compound has the formula:

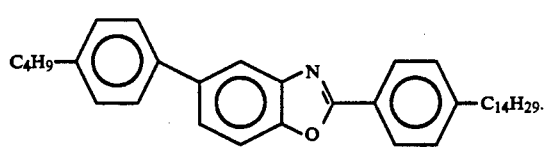

16. A composition according to claim 1, wherein said at least one mesomorphic compound has the formula:

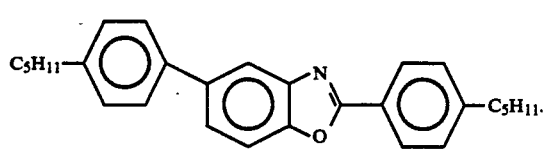

17. A composition according to claim 1, wherein said at least one mesomorphic compound has the formula:

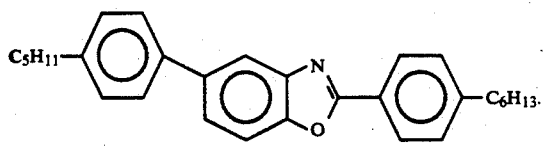

18. A composition according to claim 1, wherein said at least one mesomorphic compound has the formula:

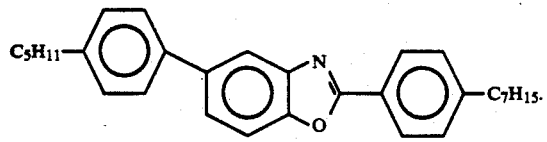

19. A composition according to claim 1, wherein said at least one mesomorphic compound has the formula:

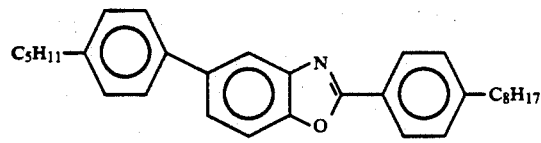

20. A composition according to claim 1, wherein said at least one mesomorphic compound has the formula:

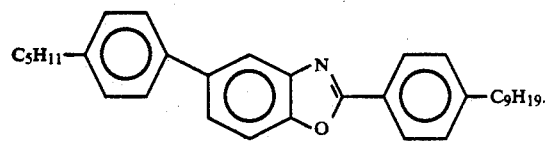

21. A composition according to claim 1, wherein said at least one mesomorphic compound has the formula:

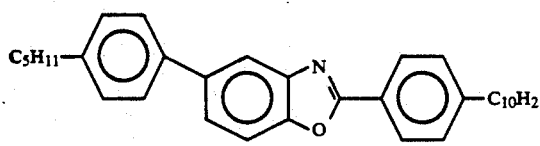

22. A composition according to claim 1, wherein said at least one mesomorphic compound has the formula:

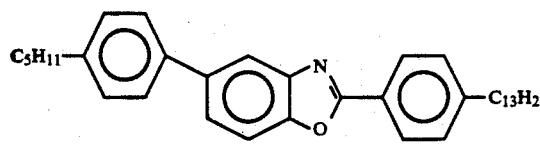

23. A composition according to claim 1, wherein said at least one mesomorphic compound has the formula:

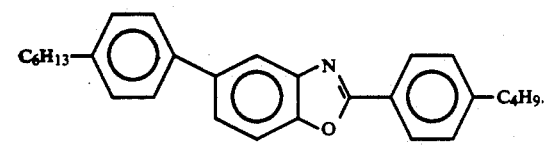

24. A composition according to claim 1, wherein said at least one mesomorphic compound has the formula:

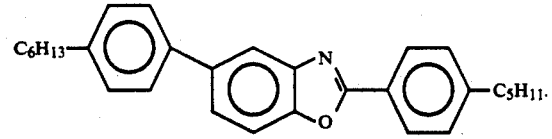

25. A composition according to claim 1, wherein said at least one mesomorphic compound has the formula:

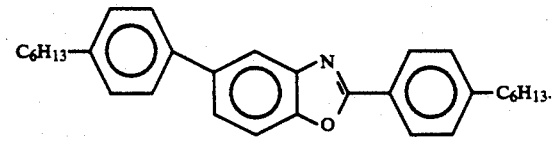

26. A composition according to claim 1, wherein said at least one mesomorphic compound has the formula:

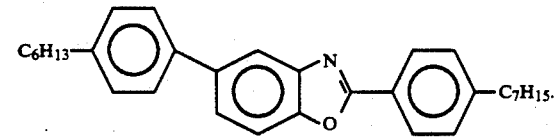

27. A composition according to claim 1, wherein said at least one mesomorphic compound has the formula:

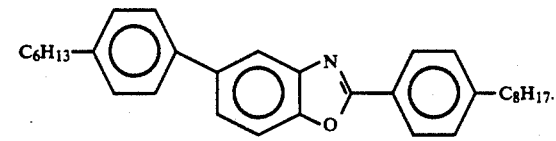

28. A composition according to claim 1, wherein said at least one mesomorphic compound has the formula:

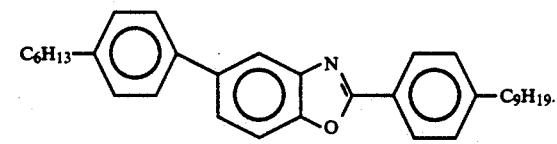

29. A composition according to claim 1, wherein said at least one mesomorphic compound has the formula:

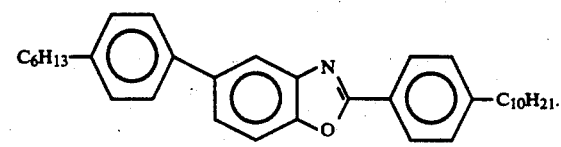

30. A composition according to claim 1, wherein said at least one mesomorphic compound has the formula:

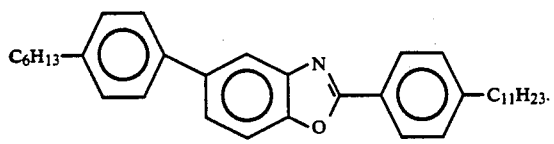

31. A composition according to claim 1, wherein said at least one mesomorphic compound has the formula:

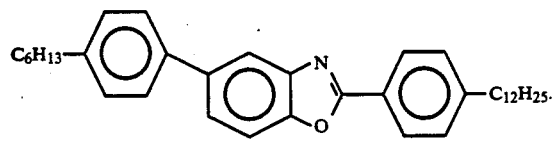

32. A composition according to claim 1, wherein said at least one mesomorphic compound has the formula:

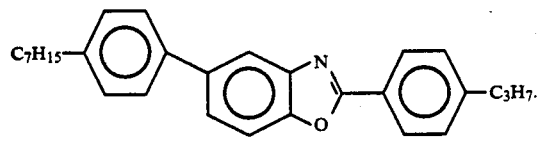

33. A composition according to claim 1, wherein said at least one mesomorphic compound has the formula:

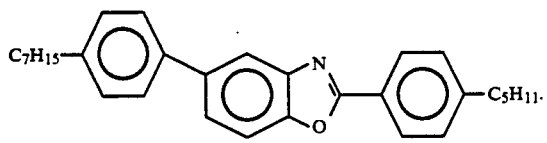

34. A composition according to claim 1, wherein said at least one mesomorphic compound has the formula:

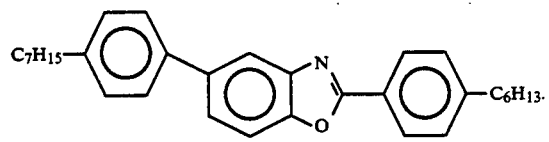

35. A composition according to claim 1, wherein said at least one mesomorphic compound has the formula:

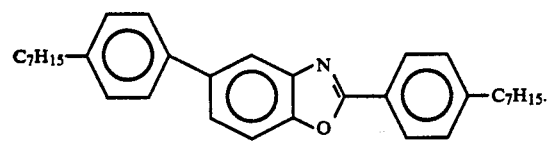

36. A composition according to claim 1, wherein said at least one mesomorphic compound has the formula:

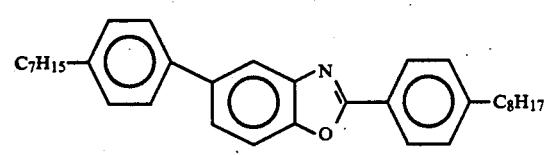

37. A composition according to claim 1, wherein said at least one mesomorphic compound has the formula:

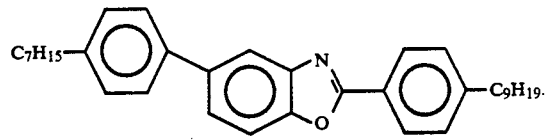

38. A composition according to claim 1, wherein said at least one mesomorphic compound has the formula:

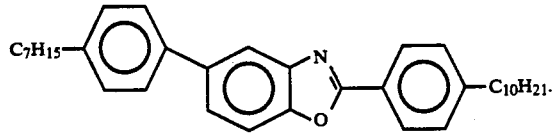

39. A composition according to claim 1, wherein said at least one mesomorphic compound has the formula:

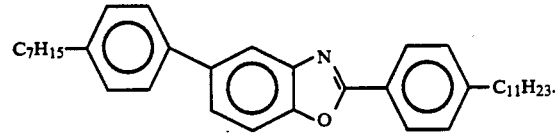

40. A composition according to claim 1, wherein said at least one mesomorphic compound has the formula:

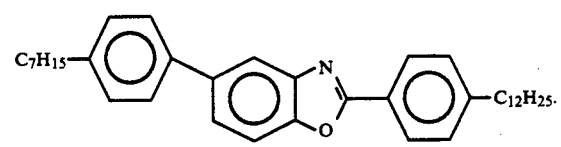

41. A composition according to claim 1, wherein said at least one mesomorphic compound has the formula:

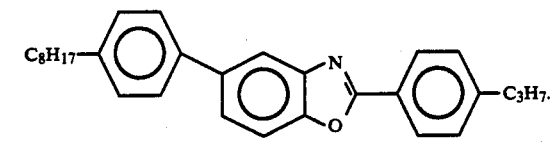

42. A composition according to claim 1, wherein said at least one mesomorphic compound has the formula:

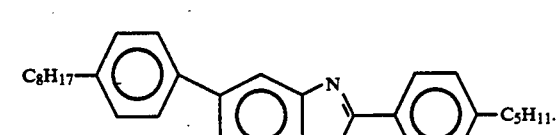

43. A composition according to claim 1, wherein said at least one mesomorphic compound has the formula:

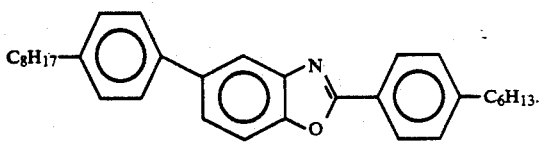

44. A composition according to claim 1, wherein said at least one mesomorphic compound has the formula:

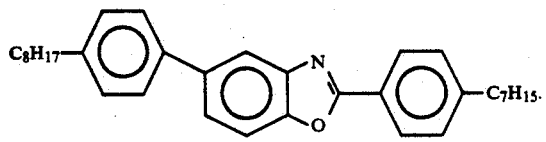

45. A composition according to claim 1, wherein said at least one mesomorphic compound has the formula:

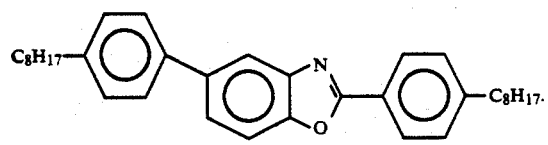

46. A composition according to claim 1, wherein said at least one mesomorphic compound has the formula:

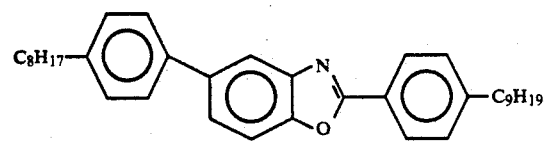

47. A composition according to claim 1, wherein said at least one mesomorphic compound has the formula:

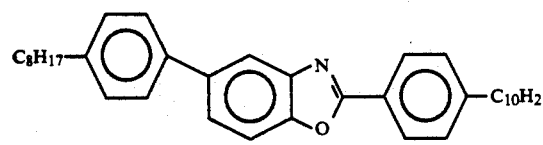

48. A composition according to claim 1, wherein said at least one mesomorphic compound has the formula:

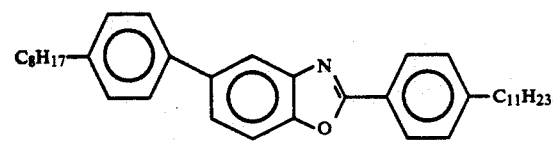

49. A composition according to claim 1, wherein said at least one mesomorphic compound has the formula:

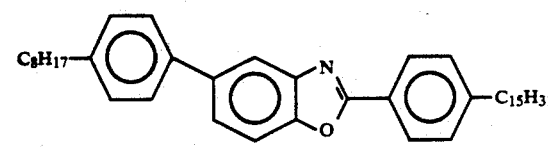

50. A composition according to claim 1, wherein said at least one mesomorphic compound has the formula:

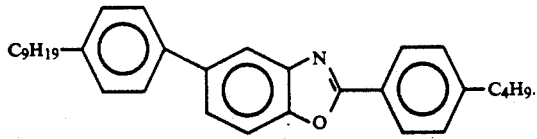

51. A composition according to claim 1, wherein said at least one mesomorphic compound has the formula:

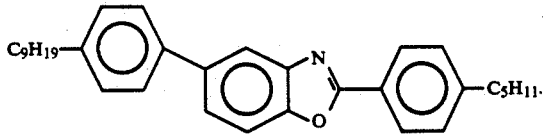

52. A composition according to claim 1, wherein said at least one mesomorphic compound has the formula:

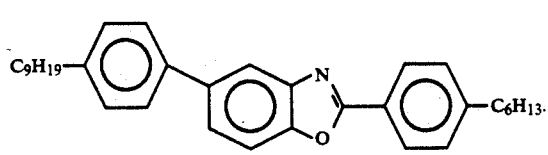

53. A composition according to claim 1, wherein said at least one mesomorphic compound has the formula:

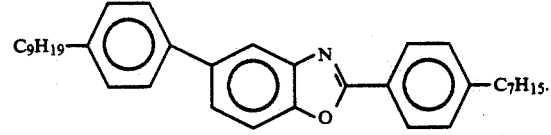

54. A composition according to claim 1, wherein said at least one mesomorphic compound has the formula:

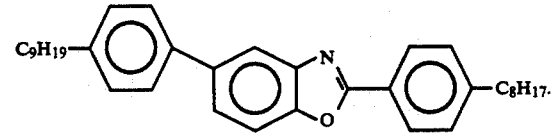

55. A composition according to claim 1, wherein said at least one mesomorphic compound has the formula:

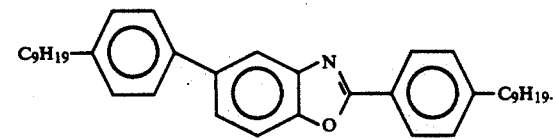

56. A composition according to claim 1, wherein said at least one mesomorphic compound has the formula:

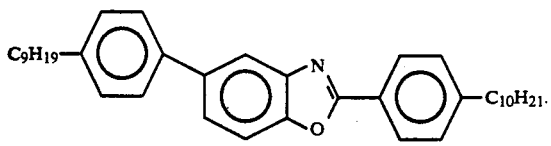

57. A composition according to claim 1, wherein said at least one mesomorphic compound has the formula:

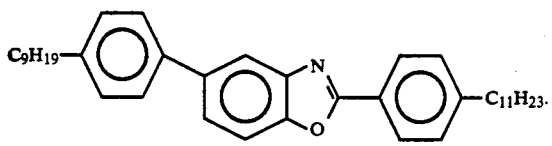

58. A composition according to claim 1, wherein said at least one mesomorphic compound has the formula:

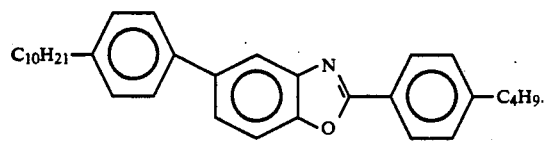

59. A composition according to claim 1, wherein said at least one mesomorphic compound has the formula:

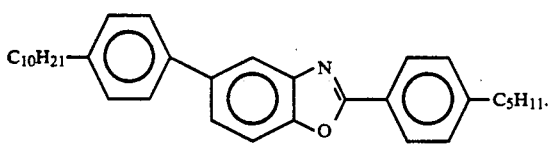

60. A composition according to claim 1, wherein said at least one mesomorphic compound has the formula:

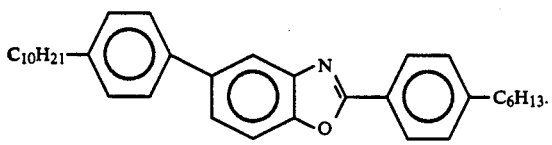

61. A composition according to claim 1, wherein said at least one mesomorphic compound has the formula:

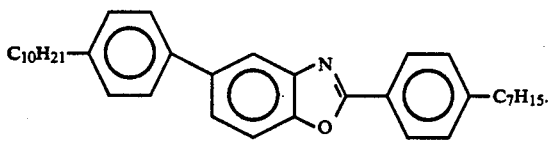

62. A composition according to claim 1, wherein said at least one mesomorphic compound has the formula:

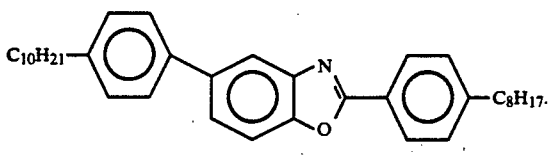

63. A composition according to claim 1, wherein said at least one mesomorphic compound has the formula:

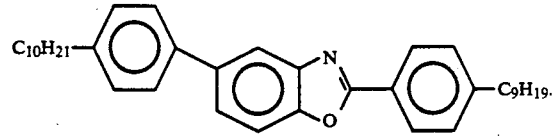

64. A composition according to claim 1, wherein said at least one mesomorphic compound has the formula:

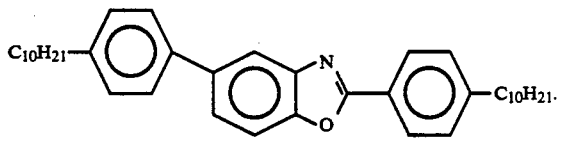

65. A composition according to claim 1, wherein said at least one mesomorphic compound has the formula:

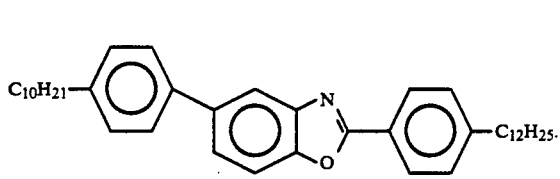

66. A composition according to claim 1, wherein said at least one mesomorphic compound has the formula:

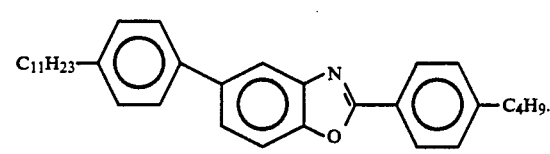

67. A composition according to claim 1, wherein said at least one mesomorphic compound has the formula:

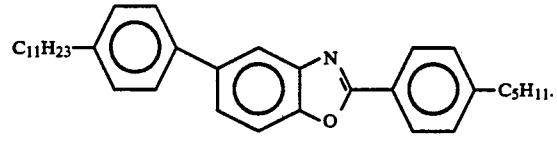

68. A composition according to claim 1, wherein said at least one mesomorphic compound has the formula:

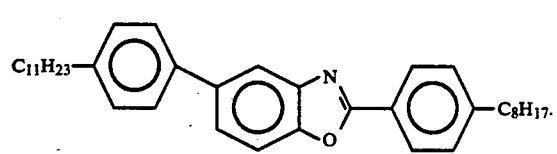

69. A composition according to claim 1, wherein said at least one mesomorphic compound has the formula:

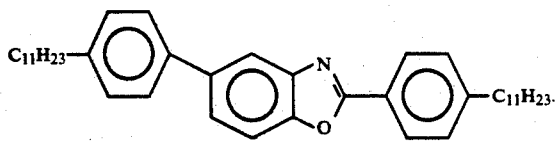

70. A composition according to claim 1, wherein said at least one mesomorphic compound has the formula:

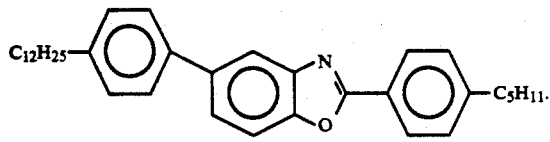

71. A composition according to claim 1, wherein said at least one mesomorphic compound has the formula:

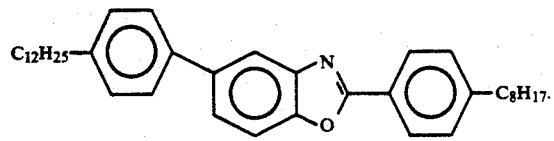

72. A composition according to claim 1, wherein said at least one mesomorphic compound has the formula:

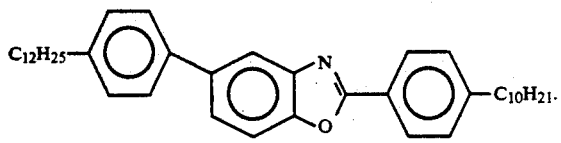

73. A composition according to claim 1, wherein said at least one mesomorphic compound has the formula:

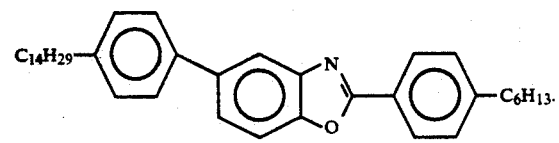

74. A composition according to claim 1, wherein said at least one mesomorphic compound has the formula:

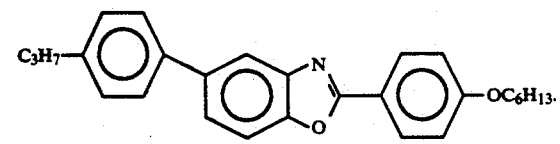

75. A composition according to claim 1, wherein said at least one mesomorphic compound has the formula:

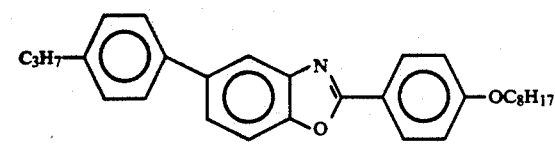

76. A composition according to claim 1, wherein said at least one mesomorphic compound has the formula:

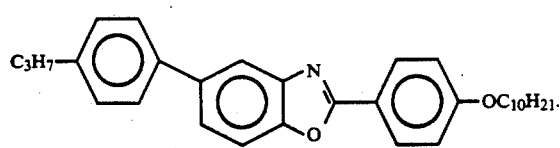

77. A composition according to claim 1, wherein said at least one mesomorphic compound has the formula:

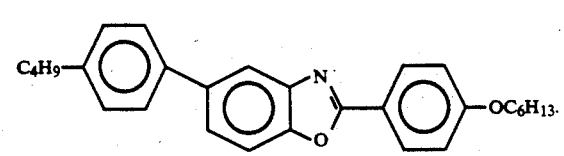

78. A composition according to claim 1, wherein said at least one mesomorphic compound has the formula:

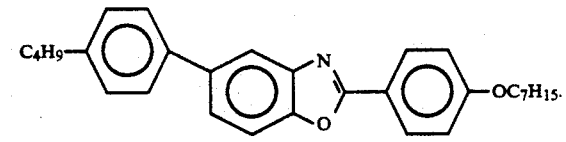

79. A composition according to claim 1, wherein said at least one mesomorphic compound has the formula:

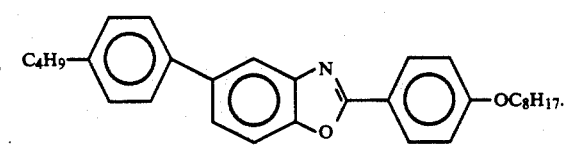

80. A composition according to claim 1, wherein said at least one mesomorphic compound has the formula:

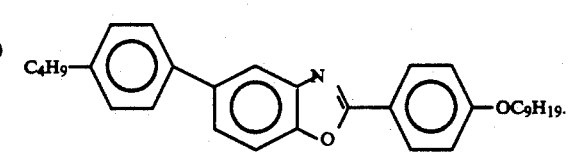

81. A composition according to claim 1, wherein said at least one mesomorphic compound has the formula:

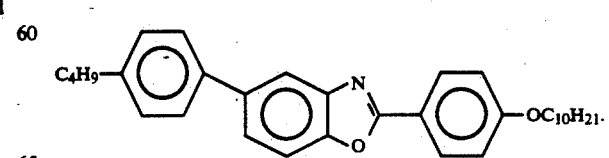

82. A composition according to claim 1, wherein said at least one mesomorphic compound has the formula:

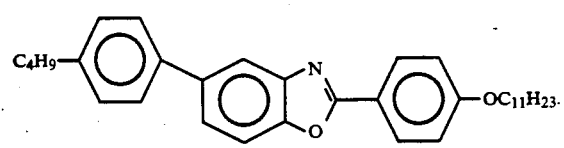

83. A composition according to claim 1, wherein said at least one mesomorphic compound has the formula:

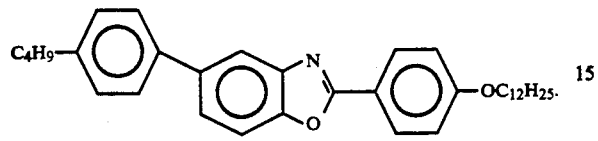

84. A composition according to claim 1, wherein said at least one mesomorphic compound has the formula:

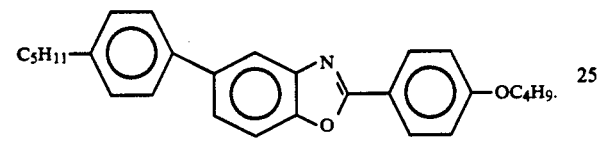

85. A composition according to claim 1, wherein said at least one mesomorphic compound has the formula:

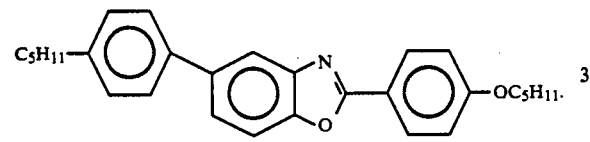

86. A composition according to claim 1, wherein said at least one mesomorphic compound has the formula:

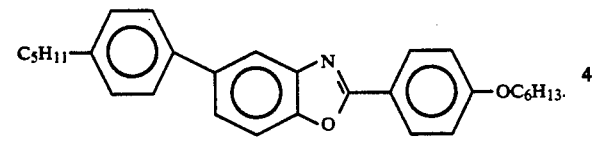

87. A composition according to claim 1, wherein said at least one mesomorphic compound has the formula:

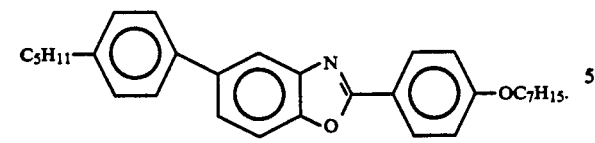

88. A composition according to claim 1, wherein said at least one mesomorphic compound has the formula:

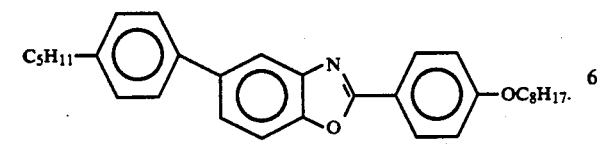

89. A composition according to claim 1, wherein said at least one mesomorphic compound has the formula:

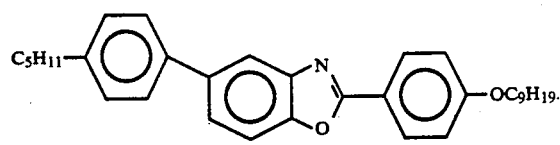

90. A composition according to claim 1, wherein said at least one mesomorphic compound has the formula:

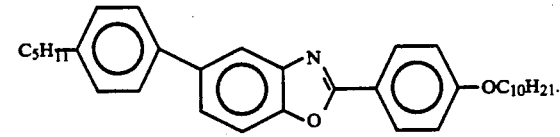

91. A composition according to claim 1, wherein said at least one mesomorphic compound has the formula:

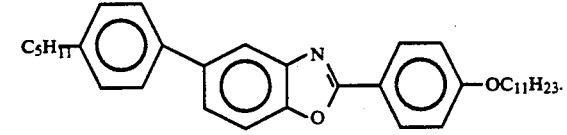

92. A composition according to claim 1, wherein said at least one mesomorphic compound has the formula:

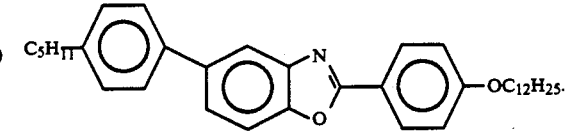

93. A composition according to claim 1, wherein said at least one mesomorphic compound has the formula:

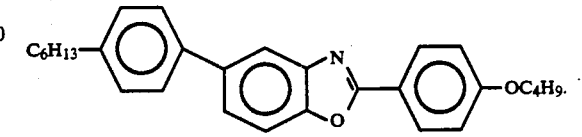

94. A composition according to claim 1, wherein said at least one mesomorphic compound has the formula:

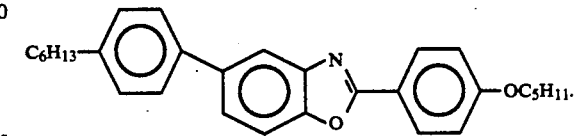

95. A composition according to claim 1, wherein said at least one mesomorphic compound has the formula:

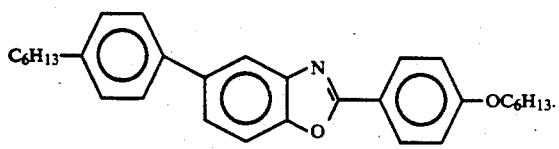

96. A composition according to claim 1, wherein said at least one mesomorphic compound has the formula:

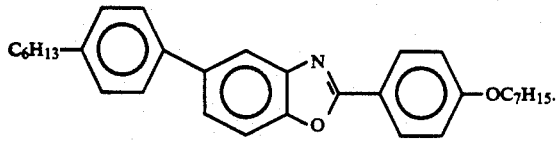

97. A composition according to claim 1, wherein said at least one mesomorphic compound has the formula:

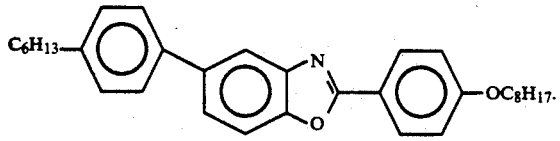

98. A composition according to claim 1, wherein said at least one mesomorphic compound has the formula:

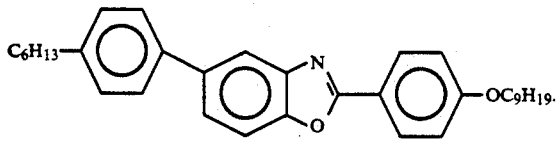

99. A composition according to claim 1, wherein said at least one mesomorphic compound has the formula:

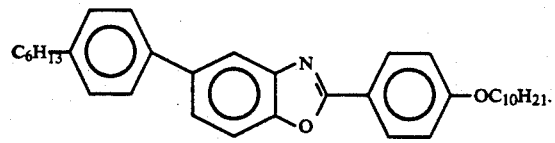

100. A composition according to claim 1, wherein said at least one mesomorphic compound has the formula:

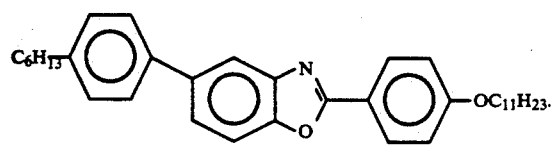

101. A composition according to claim 1, wherein said at least one mesomorphic compound has the formula:

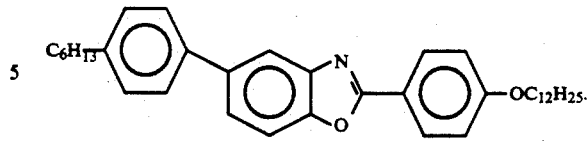

102. A composition according to claim 1, wherein said at least one mesomorphic compound has the formula:

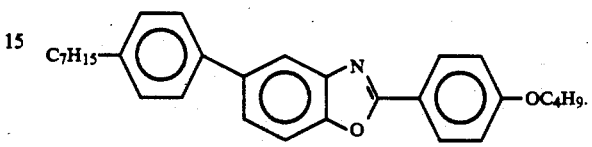

103. A composition according to claim 1, wherein said at least one mesomorphic compound has the formula:

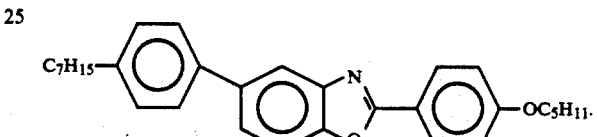

104. A composition according to claim 1, wherein said at least one mesomorphic compound has the formula:

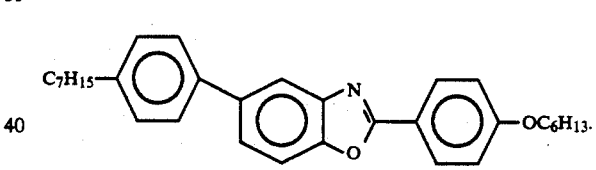

105. A composition according to claim 1, wherein said at least one mesomorphic compound has the formula:

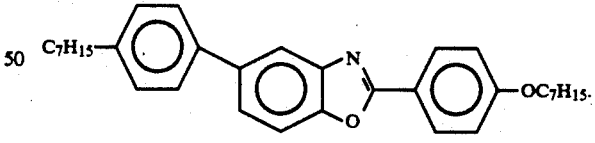

106. A composition according to claim 1, wherein said at least one mesomorphic compound has the formula:

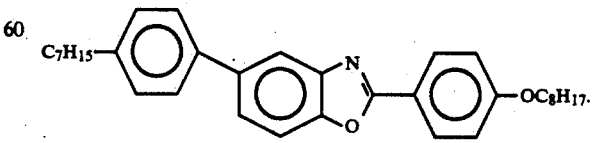

107. A composition according to claim 1, wherein said at least one mesomorphic compound has the formula:

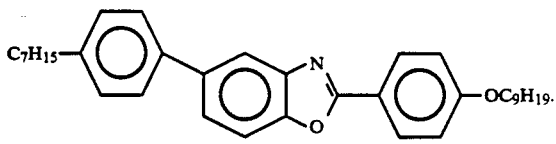

108. A composition according to claim 1, wherein said at least one mesomorphic compound has the formula:

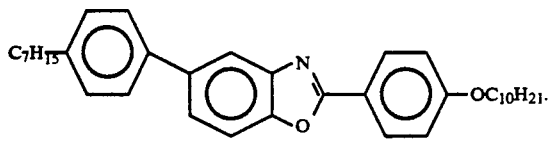

109. A composition according to claim 1, wherein said at least one mesomorphic compound has the formula:

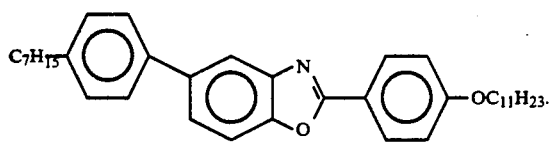

110. A composition according to claim 1, wherein said at least one mesomorphic compound has the formula:

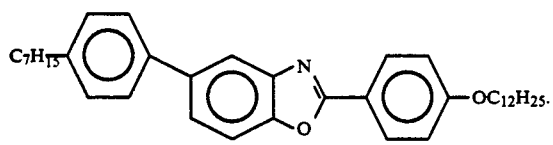

111. A composition according to claim 1, wherein said at least one mesomorphic compound has the formula:

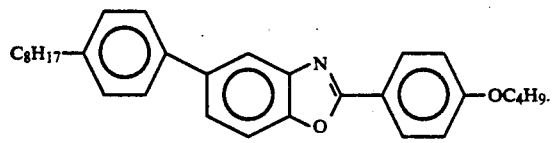

112. A composition according to claim 1, wherein said at least one mesomorphic compound has the formula:

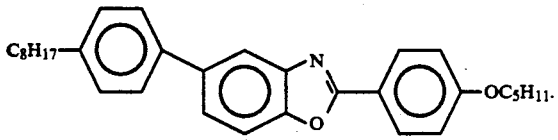

113. A composition according to claim 1, wherein said at least one mesomorphic compound has the formula:

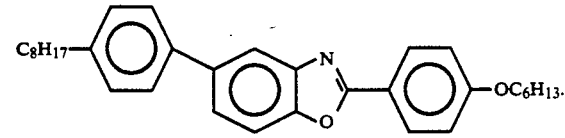

114. A composition according to claim 1, wherein said at least one mesomorphic compound has the formula:

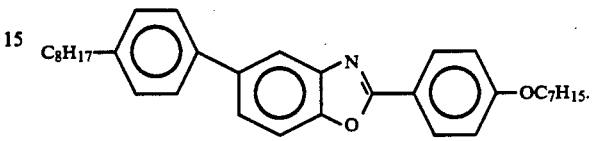

115. A composition according to claim 1, wherein said at least one mesomorphic compound has the formula:

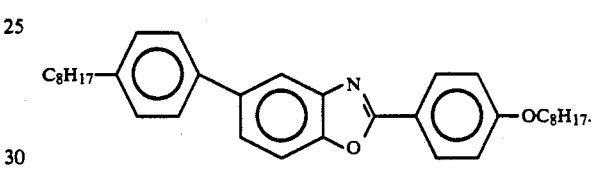

116. A composition according to claim 1, wherein said at least one mesomorphic compound has the formula:

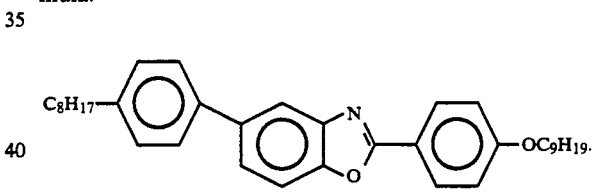

117. A composition according to claim 1, wherein said at least one mesomorphic compound has the formula:

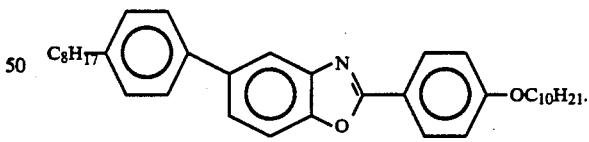

118. A composition according to claim 1, wherein said at least one mesomorphic compound has the formula:

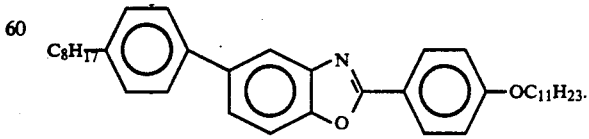

119. A composition according to claim 1, wherein said at least one mesomorphic compound has the formula:

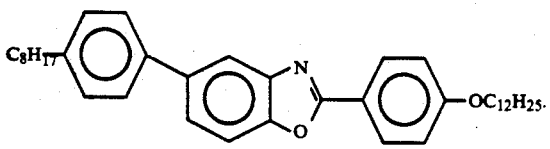

120. A composition according to claim 1, wherein said at least one mesomorphic compound has the formula:

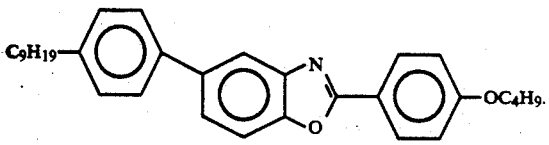

121. A composition according to claim 1, wherein said at least one mesomorphic compound has the formula:

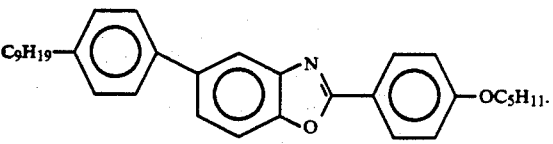

122. A composition according to claim 1, wherein said at least one mesomorphic compound has the formula:

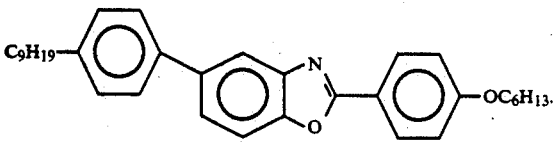

123. A composition according to claim 1, wherein said at least one mesomorphic compound has the formula:

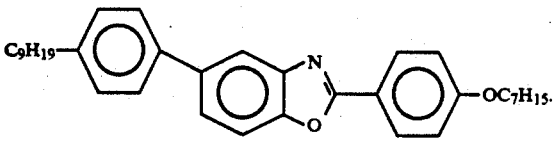

124. A composition according to claim 1, wherein said at least one mesomorphic compound has the formula:

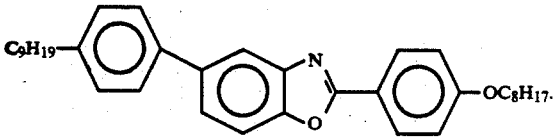

125. A composition according to claim 1, wherein said at least one mesomorphic compound has the formula:

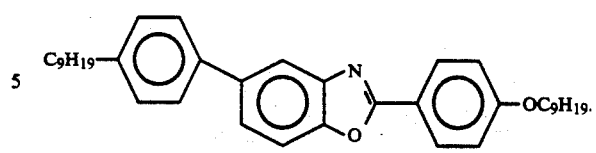

126. A composition according to claim 1, wherein said at least one mesomorphic compound has the formula:

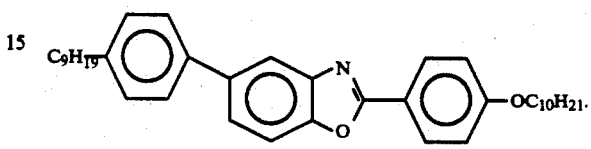

127. A composition according to claim 1, wherein said at least one mesomorphic compound has the formula:

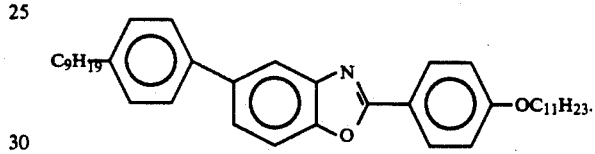

128. A composition according to claim 1, wherein said at least one mesomorphic compound has the formula:

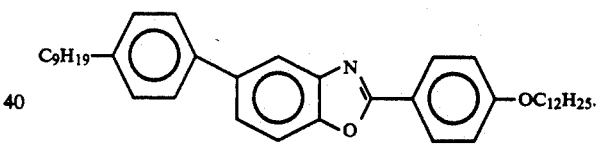

129. A composition according to claim 1, wherein said at least one mesomorphic compound has the formula:

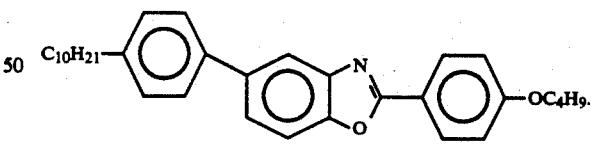

130. A composition according to claim 1, wherein said at least one mesomorphic compound has the formula:

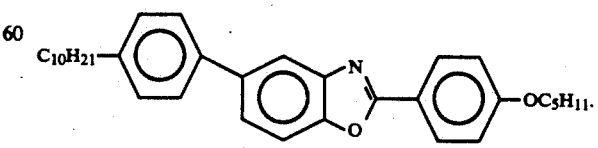

131. A composition according to claim 1, wherein said at least one mesomorphic compound has the formula:

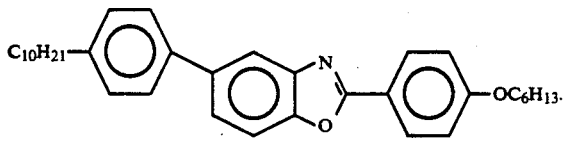

132. A composition according to claim 1, wherein said at least one mesomorphic compound has the formula:

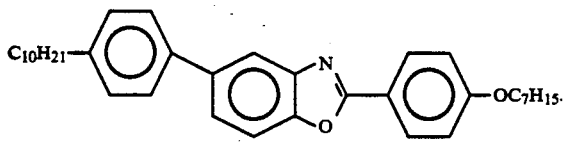

133. A composition according to claim 1, wherein said at least one mesomorphic compound has the formula:

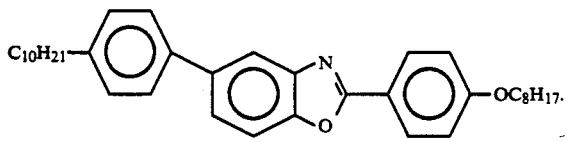

134. A composition according to claim 1, wherein said at least one mesomorphic compound has the formula:

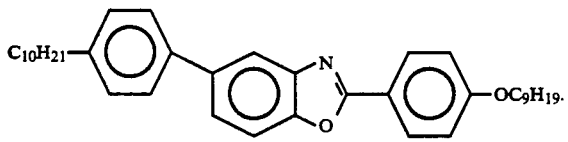

135. A composition according to claim 1, wherein said at least one mesomorphic compound has the formula:

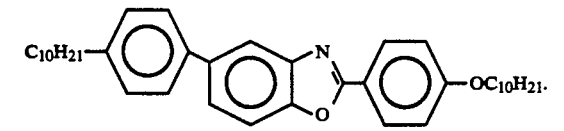

136. A composition according to claim 1, wherein said at least one mesomorphic compound has the formula:

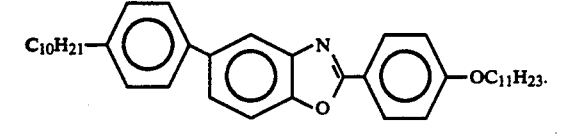

137. A composition according to claim 1, wherein said at least one mesomorphic compound has the formula:

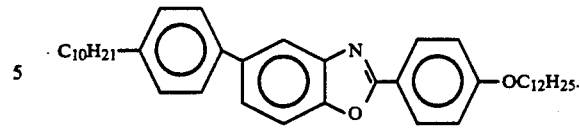

138. A composition according to claim 1, wherein said at least one mesomorphic compound has the formula:

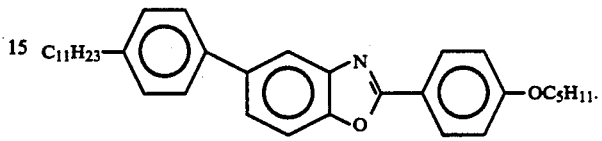

139. A composition according to claim 1, wherein said at least one mesomorphic compound has the formula:

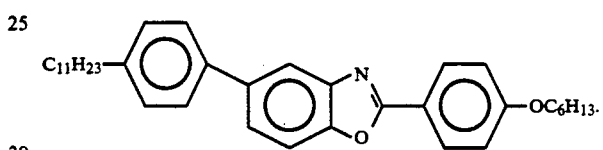

140. A composition according to claim 1, wherein said at least one mesomorphic compound has the formula:

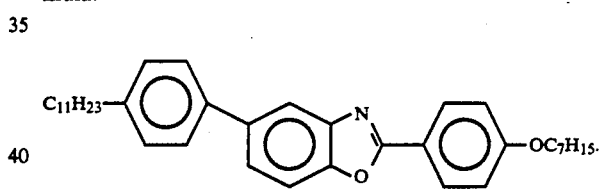

141. A composition according to claim 1, wherein said at least one mesomorphic compound has the formula:

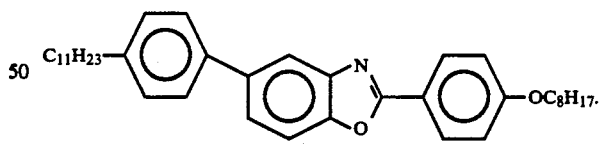

142. A composition according to claim 1, wherein said at least one mesomorphic compound has the formula:

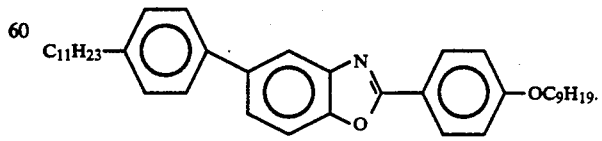

143. A composition according to claim 1, wherein said at least one mesomorphic compound has the formula:

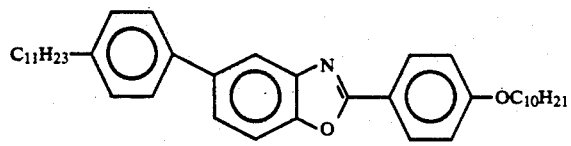

144. A composition according to claim 1, wherein said at least one mesomorphic compound has the formula:

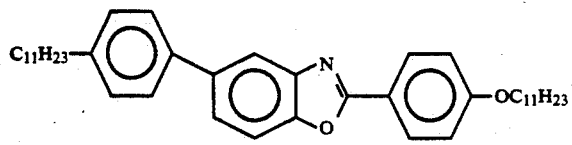

145. A composition according to claim 1, wherein said at least one mesomorphic compound has the formula:

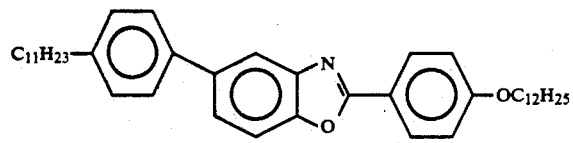

146. A composition according to claim 1, wherein said at least one mesomorphic compound has the formula:

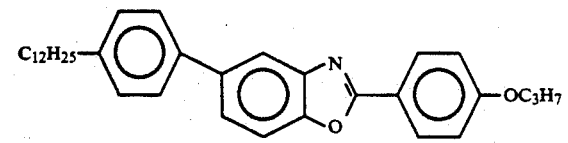

147. A composition according to claim 1, wherein said at least one mesomorphic compound has the formula:

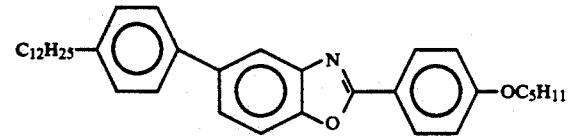

148. A composition according to claim 1, wherein said at least one mesomorphic compound has the formula:

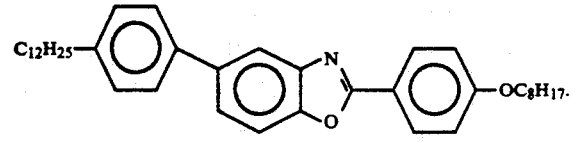

149. A composition according to claim 1, wherein said at least one mesomorphic compound has the formula:

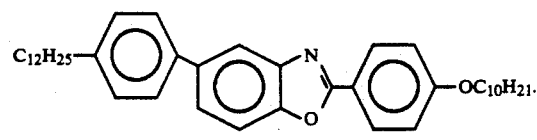

150. A composition according to claim 1, wherein said at least one mesomorphic compound has the formula:

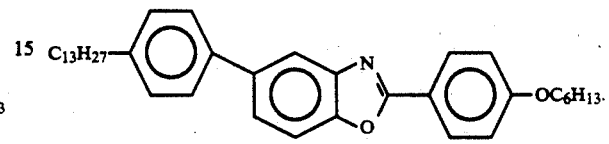

151. A composition according to claim 1, wherein said at least one mesomorphic compound has the formula:

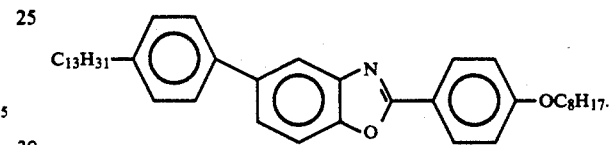

152. A composition according to claim 1, wherein said at least one mesomorphic compound has the formula:

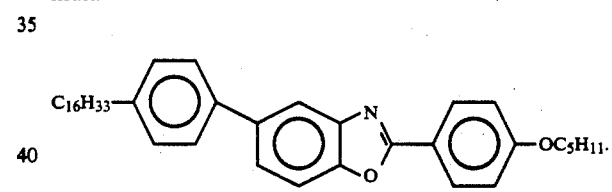

153. A composition according to claim 1, wherein said at least one mesomorphic compound has the formula:

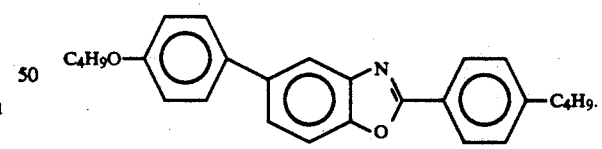

154. A composition according to claim 1, wherein said at least one mesomorphic compound has the formula:

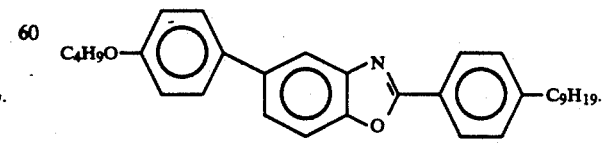

155. A composition according to claim 1, wherein said at least one mesomorphic compound has the formula:

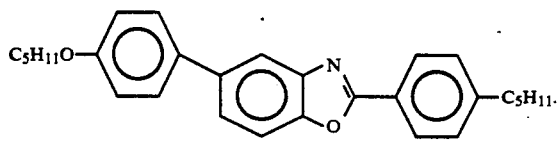

156. A composition according to claim 1, wherein said at least one mesomorphic compound has the formula:

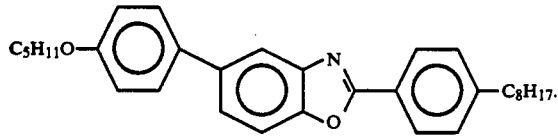

157. A composition according to claim 1, wherein said at least one mesomorphic compound has the formula:

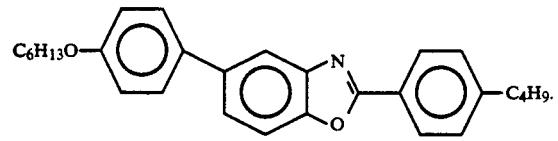

158. A composition according to claim 1, wherein said at least one mesomorphic compound has the formula:

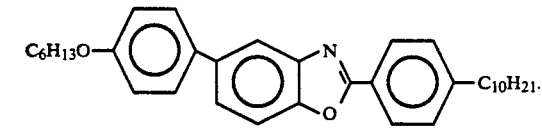

159. A composition according to claim 1, wherein said at least one mesomorphic compound has the formula:

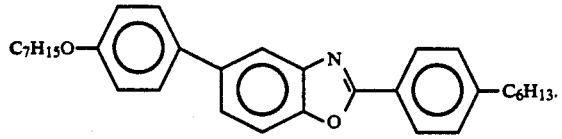

160. A composition according to claim 1, wherein said at least one mesomorphic compound has the formula:

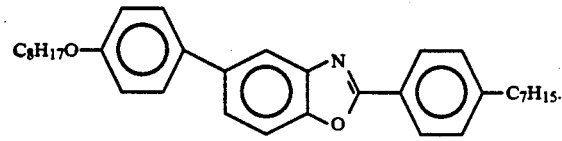

161. A composition according to claim 1, wherein said at least one mesomorphic compound has the formula:

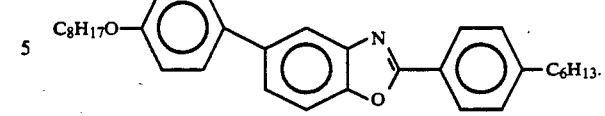

162. A composition according to claim 1, wherein said at least one mesomorphic compound has the formula:

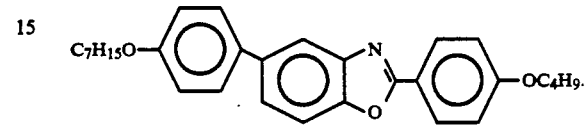

163. A composition according to claim 1, wherein said at least one mesomorphic compound has the formula:

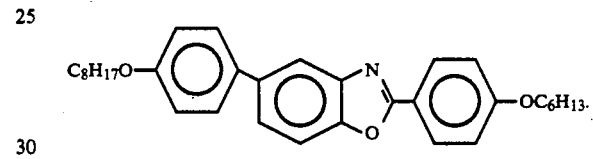

164. A composition according to claim 1, wherein said at least one mesomorphic compound has the formula:

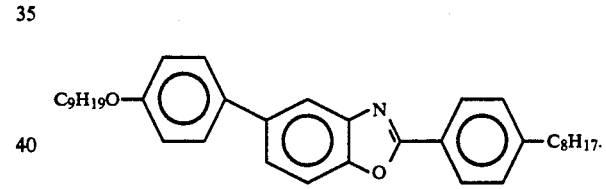

165. A composition according to claim 1, wherein said at least one mesomorphic compound has the formula:

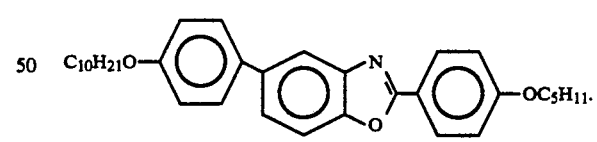

166. A composition according to claim 1, wherein said at least one mesomorphic compound has the formula:

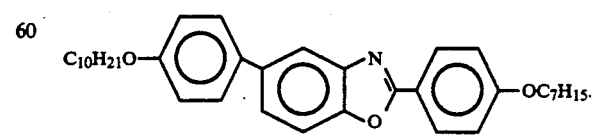

167. A composition according to claim 1, wherein said at least one mesomorphic compound has the formula:

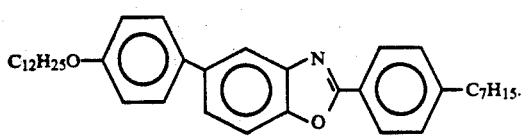

168. A composition according to claim 1, wherein said at least one mesomorphic compound has the formula:

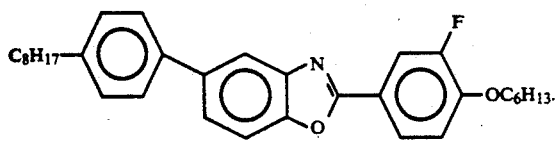

169. A composition according to claim 1, wherein said at least one mesomorphic compound has the formula:

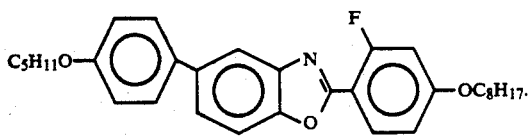

170. A composition according to claim 1, wherein said at least one mesomorphic compound has the formula:

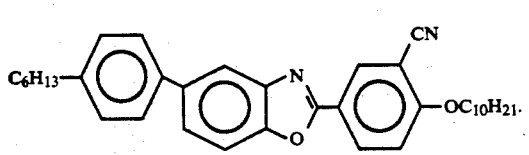

171. A composition according to claim 1, wherein said at least one mesomorphic compound has the formula:

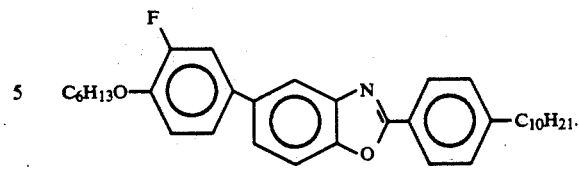

172. A composition according to claim 1, wherein said at least one mesomorphic compound has the formula:

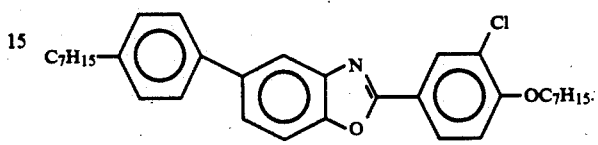

173. A composition according to claim 1, wherein said at least one mesomorphic compound has the formula:

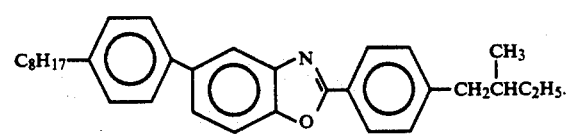

174. A composition according to claim 1, wherein said at least one mesomorphic compound has the formula:

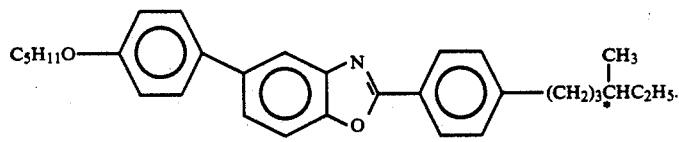

175. A composition according to claim 1, wherein said at least one mesomorphic compound has the formula:

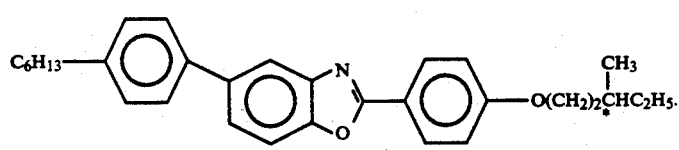

176. A composition according to claim 1, wherein said at least one mesomorphic compound has the formula:

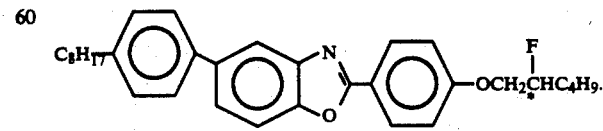

177. A composition according to claim 1, wherein said at least one mesomorphic compound has the formula:

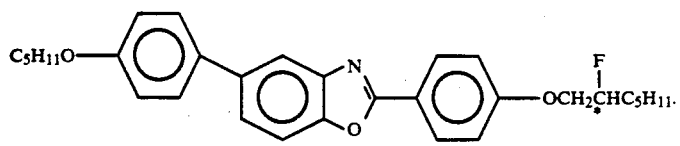

178. A composition according to claim 1, wherein said at least one mesomorphic compound has the formula:

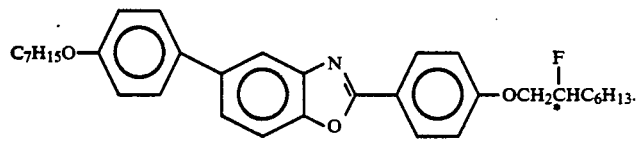

179. A composition according to claim 1, wherein said at least one mesomorphic compound has the formula:

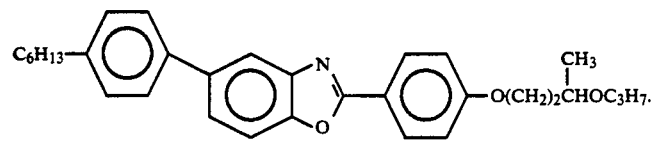

180. A composition according to claim 1, wherein said at least one mesomorphic compound has the formula:

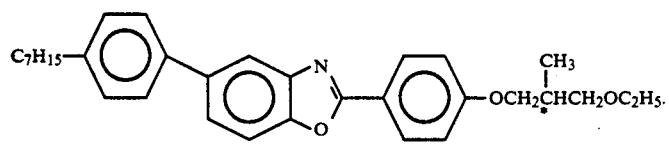

181. A composition according to claim 1, wherein said at least one mesomorphic compound has the formula:

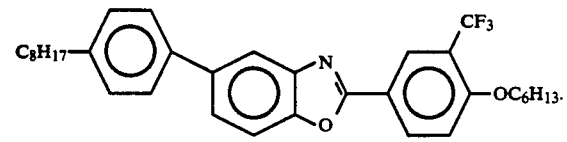

182. A composition according to claim 1, wherein said at least one mesomorphic compound has the formula:

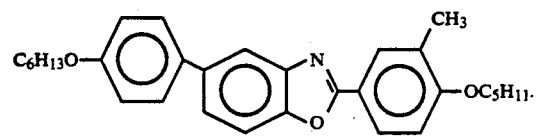

183. A composition according to claim 1, wherein said at least one mesomorphic compound has the formula:

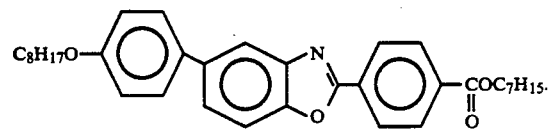

184. A composition according to claim 1, wherein said at least one mesomorphic compound has the formula:

185. A composition according to claim 1, wherein said at least one mesomorphic compound has the formula:

186. A composition according to claim 1, wherein said at least one mesomorphic compound has the formula:

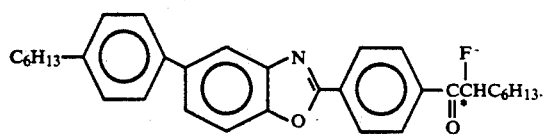

187. A composition according to claim 1, wherein said at least one mesomorphic compound has the formula:

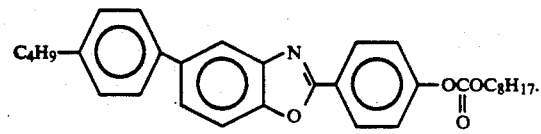

188. A composition according to claim 1, wherein said at least one mesomorphic compound has the formula:

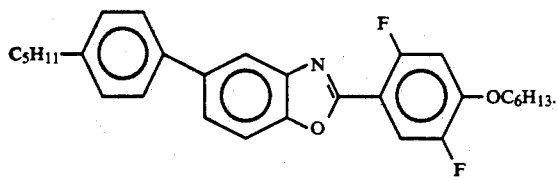

189. A composition according to claim 1, wherein said at least one mesomorphic compound has the formula:

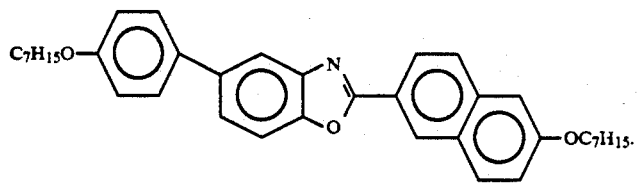

190. A composition according to claim 1, wherein said at least one mesomorphic compound has the formula:

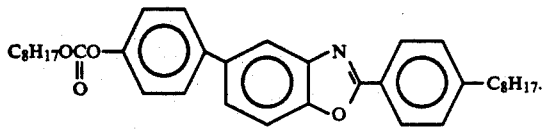

191. A composition according to claim 1, wherein said at least one mesomorphic compound has the formula:

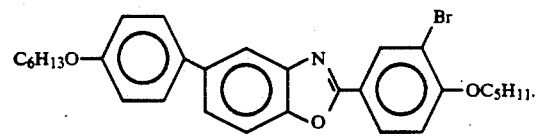

192. A composition according to claim 1, wherein said at least one mesomorphic compound has the formula:

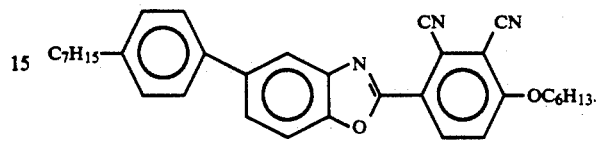

193. A composition according to claim 1, wherein said at least one mesomorphic compound has the formula:

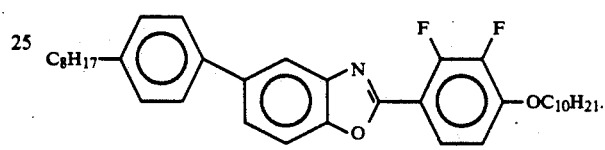

194. A composition according to claim 1, wherein said at least one mesomorphic compound has the formula:

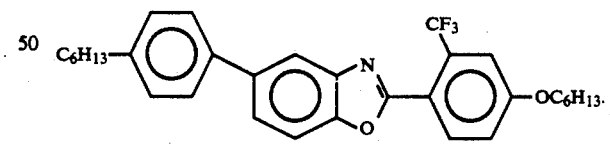

195. A composition according to claim 1, wherein said at least one mesomorphic compound has the formula:

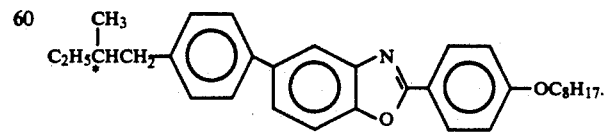

196. A composition according to claim 1, wherein said at least one mesomorphic compound has the formula:

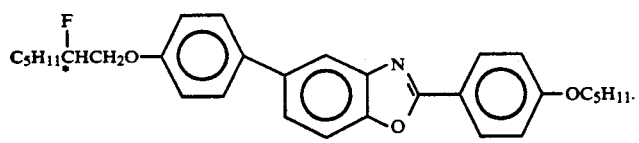

197. A composition according to claim 1, wherein said at least one mesomorphic compound has the formula:

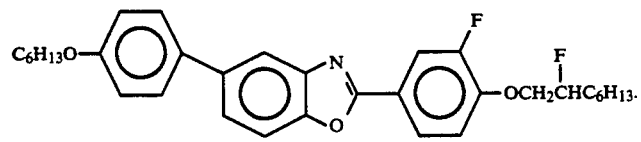

198. A composition according to claim 1, wherein said at least one mesomorphic compound has the formula:

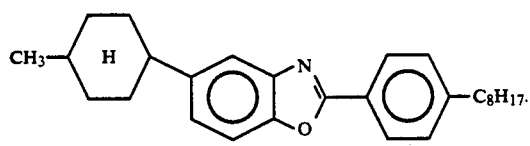

199. A composition according to claim 1, wherein said at least one mesomorphic compound has the formula:

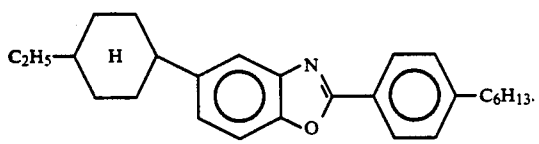

200. A composition according to claim 1, wherein said at least one mesomorphic compound has the formula:

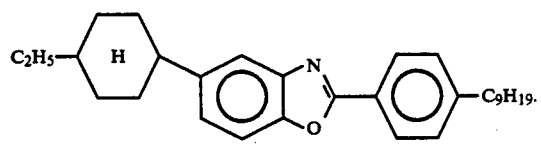

201. A composition according to claim 1, wherein said at least one mesomorphic compound has the formula:

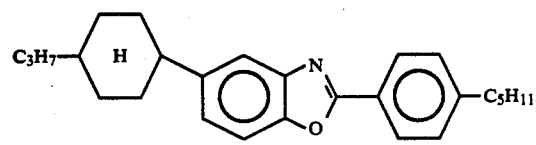

202. A composition according to claim 1, wherein said at least one mesomorphic compound has the formula:

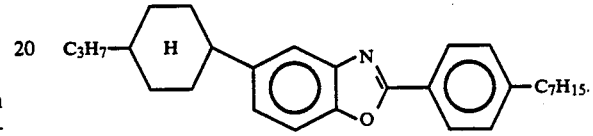

203. A composition according to claim 1, wherein said at least one mesomorphic compound has the formula:

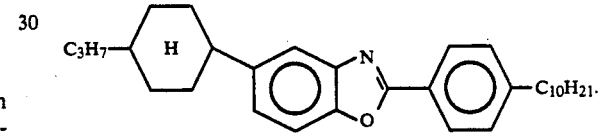

204. A composition according to claim 1, wherein said at least one mesomorphic compound has the formula:

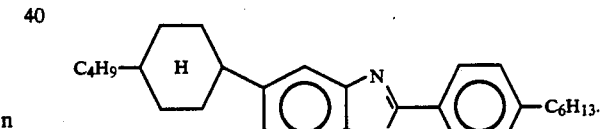

205. A composition according to claim 1, wherein said at least one mesomorphic compound has the formula:

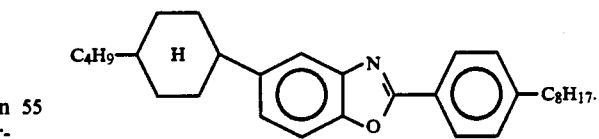

206. A composition according to claim 1, wherein said at least one mesomorphic compound has the formula:

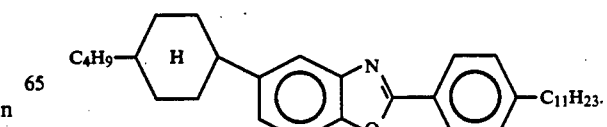

207. A composition according to claim 1, wherein said at least one mesomorphic compound has the formula:

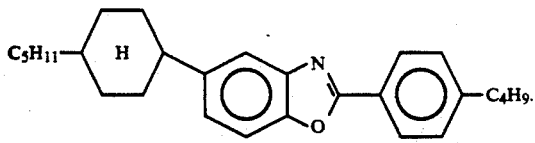

208. A composition according to claim 1, wherein said at least one mesomorphic compound has the formula:

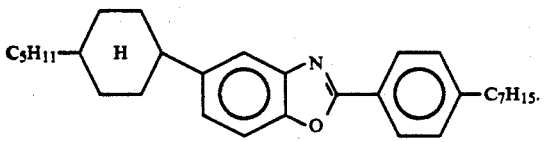

209. A composition according to claim 1, wherein said at least one mesomorphic compound has the formula:

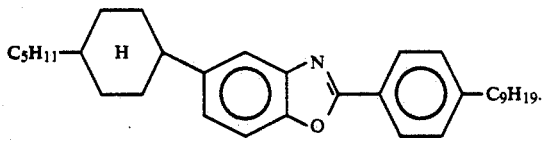

210. A composition according to claim 1, wherein said at least one mesomorphic compound has the formula:

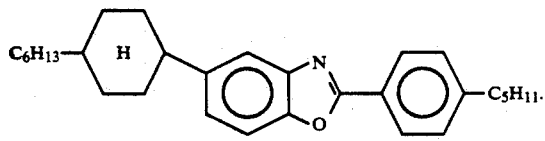

211. A composition according to claim 1, wherein said at least one mesomorphic compound has the formula:

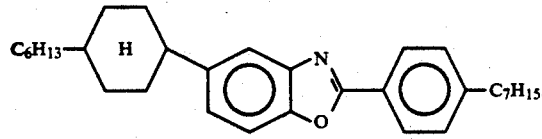

212. A composition according to claim 1, wherein said at least one mesomorphic compound has the formula:

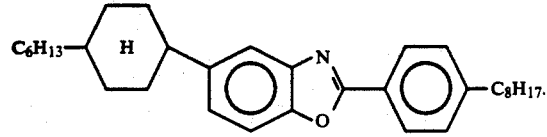

213. A composition according to claim 1, wherein said at least one mesomorphic compound has the formula:

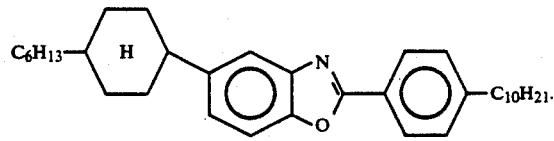

214. A composition according to claim 1, wherein said at least one mesomorphic compound has the formula:

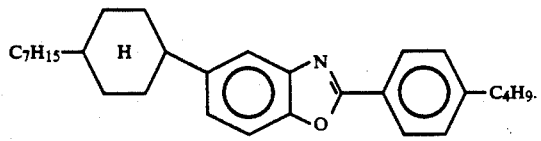

215. A composition according to claim 1, wherein said at least one mesomorphic compound has the formula:

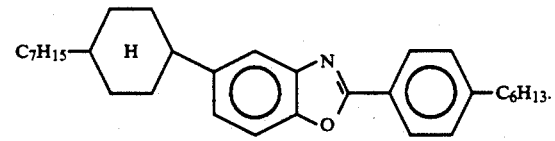

216. A composition according to claim 1, wherein said at least one mesomorphic compound has the formula:

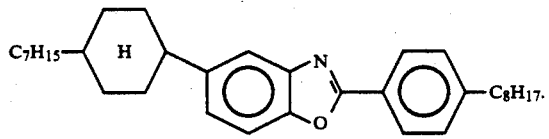

217. A composition according to claim 1, wherein said at least one mesomorphic compound has the formula:

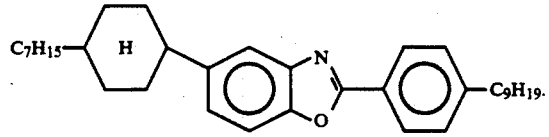

218. A composition according to claim 1, wherein said at least one mesomorphic compound has the formula: -

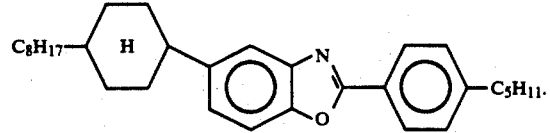

219. A composition according to claim 1, wherein said at least one mesomorphic compound has the formula:

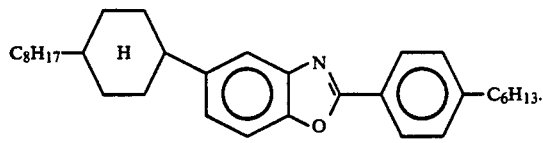

220. A composition according to claim 1, wherein said at least one mesomorphic compound has the formula:

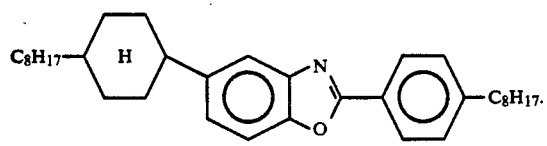

221. A composition according to claim 1, wherein said at least one mesomorphic compound has the formula:

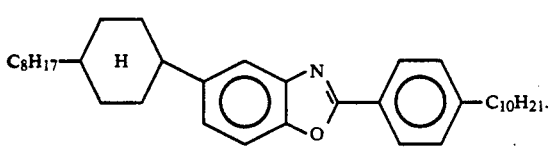

222. A composition according to claim 1, wherein said at least one mesomorphic compound has the formula:

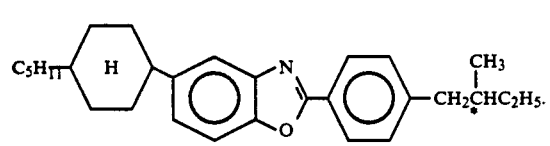

223. A composition according to claim 1, wherein said at least one mesomorphic compound has the formula:

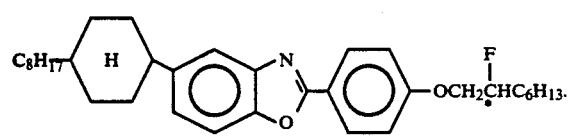

224. A composition according to claim 1, wherein said at least one mesomorphic compound has the formula:

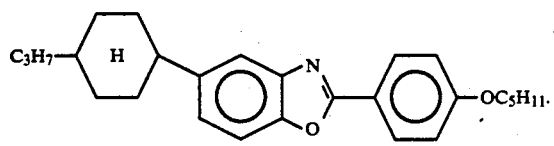

225. A composition according to claim 1, wherein said at least one mesomorphic compound has the formula:

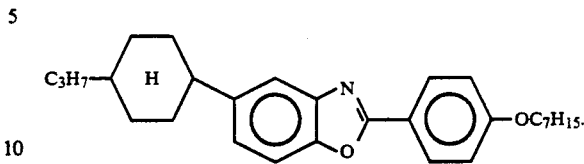

226. A composition according to claim 1, wherein said at least one mesomorphic compound has the formula:

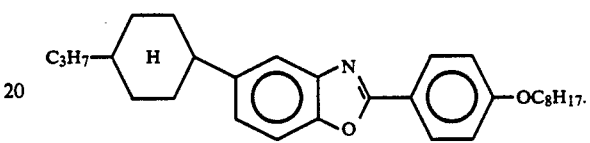

227. A composition according to claim 1, wherein said at least one mesomorphic compound has the formula:

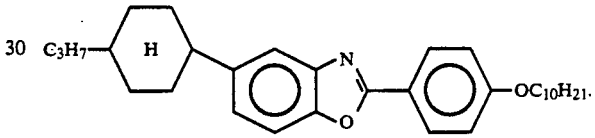

228. A composition according to claim 1, wherein said at least one mesomorphic compound has the formula:

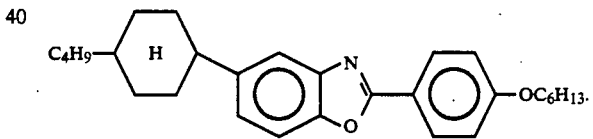

229. A composition according to claim 1, wherein said at least one mesomorphic compound has the formula:

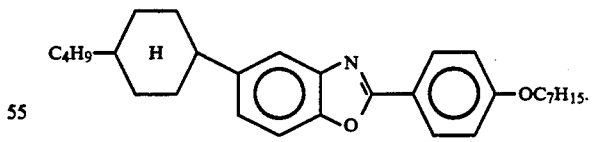

230. A composition according to claim 1, wherein said at least one mesomorphic compound has the formula:

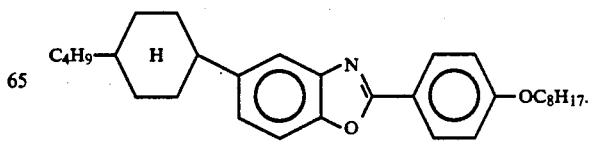

231. A composition according to claim 1, wherein said at least one mesomorphic compound has the formula:

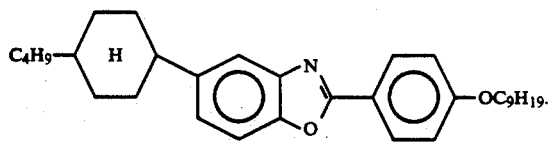

232. A composition according to claim 1, wherein said at least one mesomorphic compound has the formula:

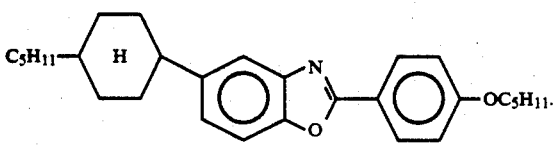

233. A composition according to claim 1, wherein said at least one mesomorphic compound has the formula:

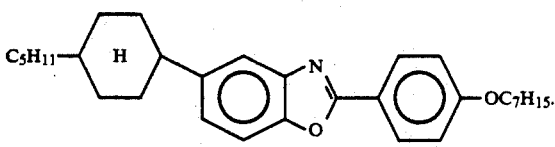

234. A composition according to claim 1, wherein said at least one mesomorphic compound has the formula:

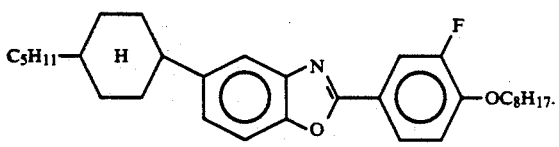

235. A composition according to claim 1, wherein said at least one mesomorphic compound has the formula:

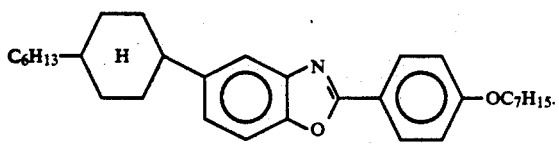

236. A composition according to claim 1, wherein said at least one mesomorphic compound has the formula:

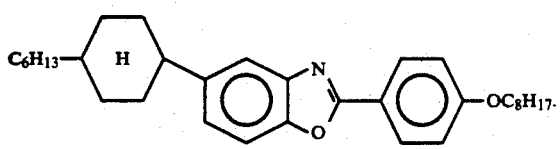

237. A composition according to claim 1, wherein said at least one mesomorphic compound has the formula:

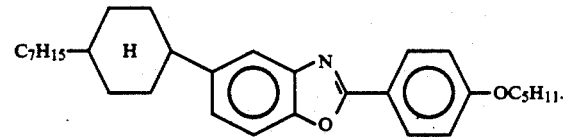

238. A composition according to claim 1, wherein said at least one mesomorphic compound has the formula:

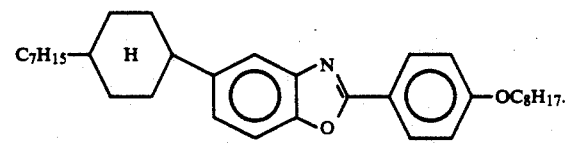

239. A composition according to claim 1, wherein said at least one mesomorphic compound has the formula:

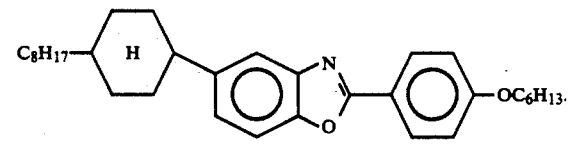

240. A composition according to claim 1, wherein said at least one mesomorphic compound has the formula:

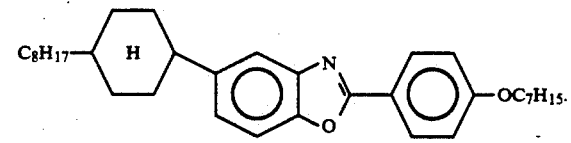

241. A composition according to claim 1, wherein said at least one mesomorphic compound has the formula:

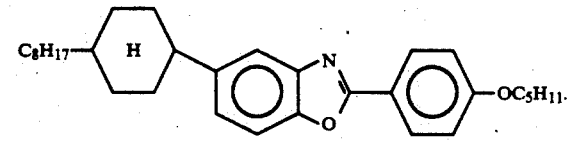

242. A composition according to claim 1, wherein said at least one mesomorphic compound has the formula:

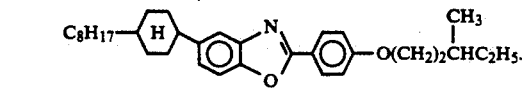

243. A composition according to claim 1, wherein said at least one mesomorphic compound has the formula:

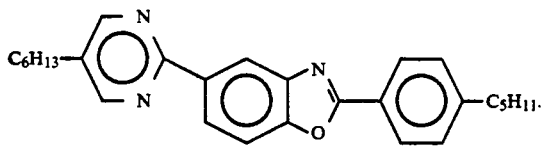

244. A composition according to claim 1, wherein said at least one mesomorphic compound has the formula:

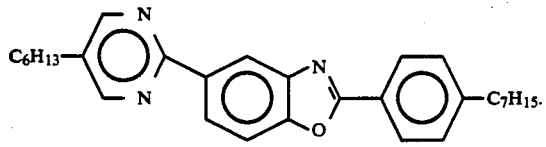

245. A composition according to claim 1, wherein said at least one mesomorphic compound has the formula:

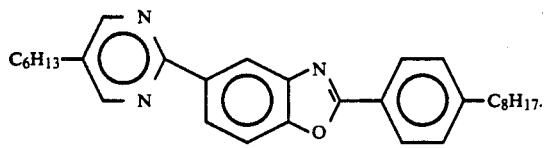

246. A composition according to claim 1, wherein said at least one mesomorphic compound has the formula:

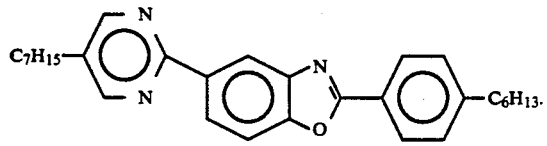

247. A composition according to claim 1, wherein said at least one mesomorphic compound has the formula:

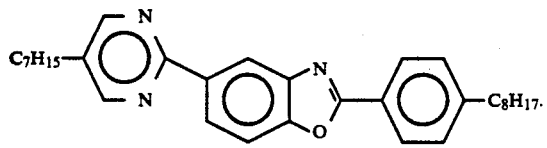

248. A composition according to claim 1, wherein said at least one mesomorphic compound has the formula:

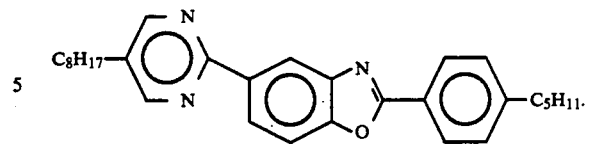

249. A composition according to claim 1, wherein said at least one mesomorphic compound has the formula:

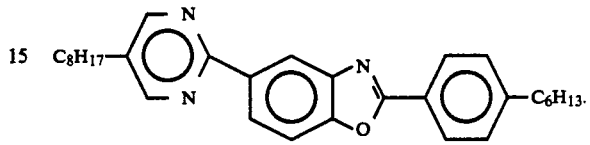

250. A composition according to claim 1, wherein said at least one mesomorphic compound has the formula:

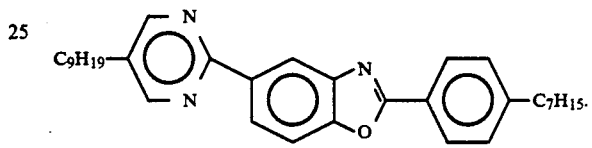

251. A composition according to claim 1, wherein said at least one mesomorphic compound has the formula:

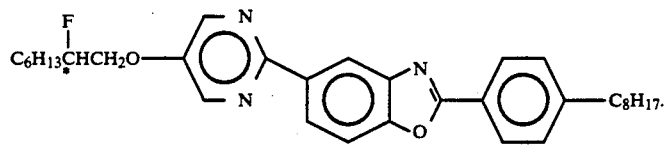

252. A composition according to claim 1, wherein said at least one mesomorphic compound has the formula:

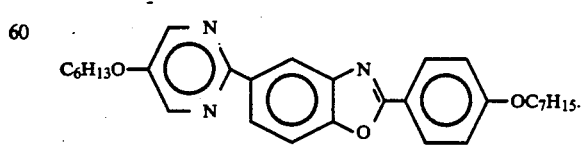

253. A composition according to claim 1, wherein said at least one mesomorphic compound has the formula:

254. A composition according to claim 1, wherein said at least one mesomorphic compound has the formula:

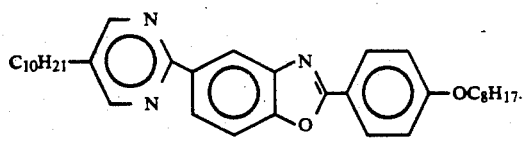

255. A composition according to claim 1, wherein said at least one mesomorphic compound has the formula:

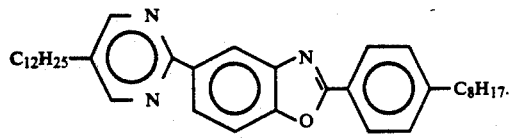

256. A composition according to claim 1, wherein said at least one mesomorphic compound has the formula:

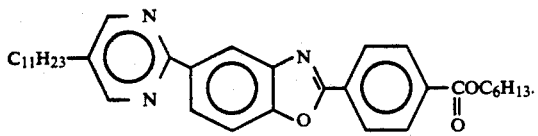

257. A composition according to claim 1, wherein said at least one mesomorphic compound has the formula:

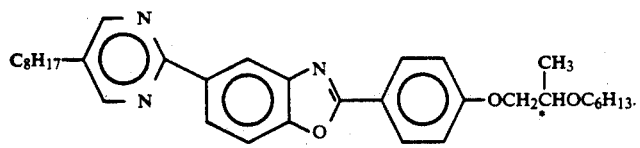

258. A composition according to claim 1, wherein said at least one mesomorphic compound has the formula:

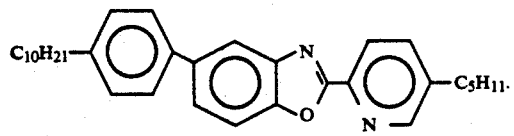

259. A composition according to claim 1, wherein said at least one mesomorphic compound has the formula:

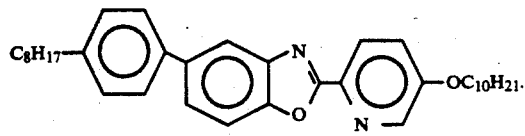

260. A composition according to claim 1, wherein said at least one mesomorphic compound has the formula:

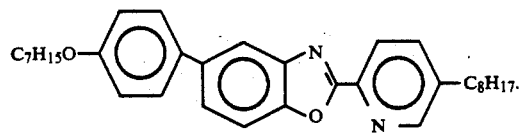

261. A composition according to claim 1, wherein said at least one mesomorphic compound has the formula:

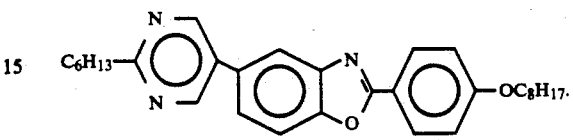

262. A composition according to claim 1, wherein said at least one mesomorphic compound has the formula:

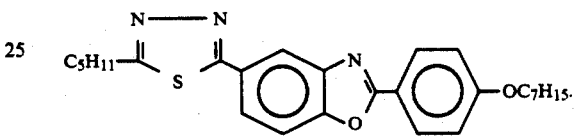

263. A composition according to claim 1, wherein said at least one mesomorphic compound has the formula:

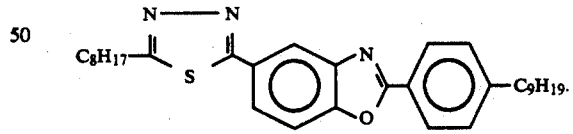

264. A composition according to claim 1, wherein said at least one mesomorphic compound has the formula:

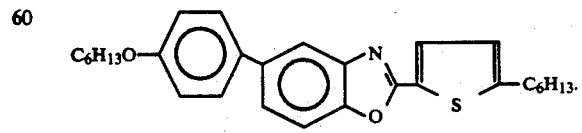

265. A composition according to claim 1, wherein said at least one mesomorphic compound has the formula:

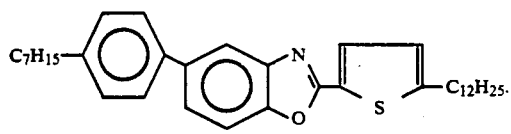

266. A composition according to claim 1, wherein said at least one mesomorphic compound has the formula:

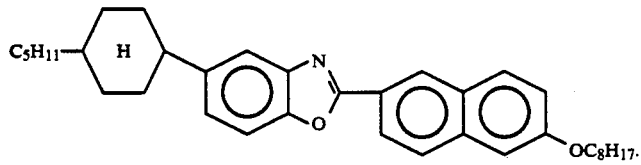

267. A composition according to claim 1, wherein said at least one mesomorphic compound has the formula:

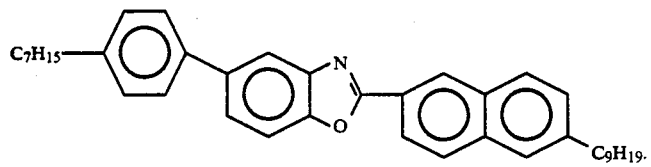

268. A composition according to claim 1, wherein said at least one mesomorphic compound has the formula:

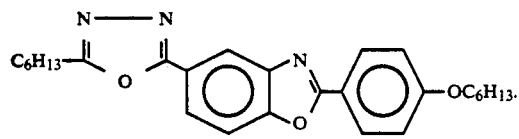

269. A composition according to claim 1, wherein said at least one mesomorphic compound has the formula:

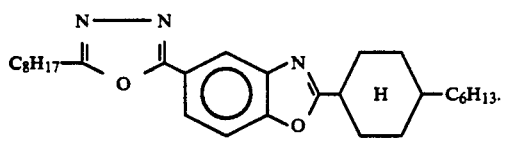

270. A composition according to claim 1, wherein said at least one mesomorphic compound has the formula:

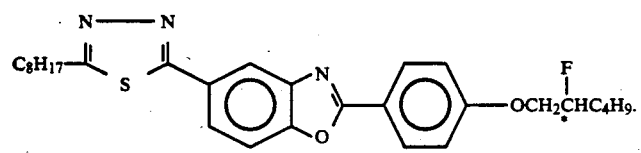

271. A composition according to claim 1, wherein said at least one mesomorphic compound has the formula:

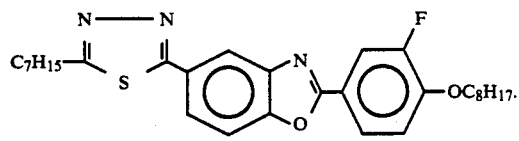

272. A composition according to claim 1, wherein said at least one mesomorphic compound has the formula:

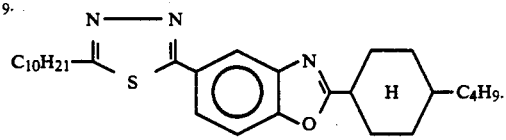

273. A composition according to claim 1, wherein said at least one mesomorphic compound has the formula:

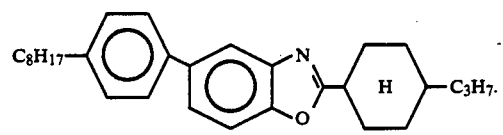

274. A composition according to claim 1, wherein said at least one mesomorphic compound has the formula:

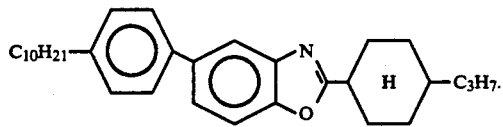

275. A composition according to claim 1, wherein said at least one mesomorphic compound has the formula:

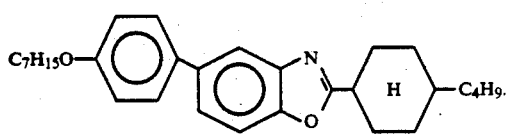

276. A composition according to claim 1, wherein said at least one mesomorphic compound has the formula:

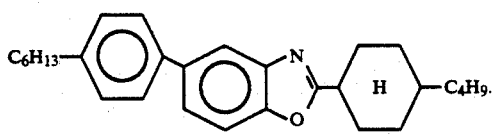

277. A composition according to claim 1, wherein said at least one mesomorphic compound has the formula:

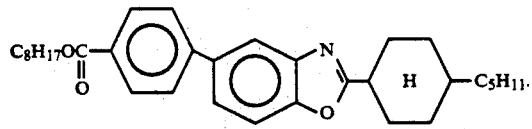

278. A composition according to claim 1, wherein said at least one mesomorphic compound has the formula:

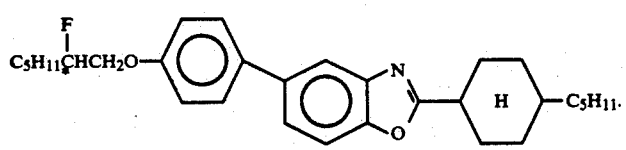

279. A composition according to claim 1, wherein said at least one mesomorphic compound has the formula:

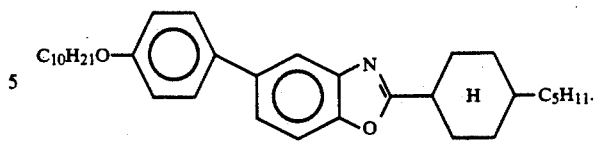

280. A composition according to claim 1, wherein said at least one mesomorphic compound has the formula:

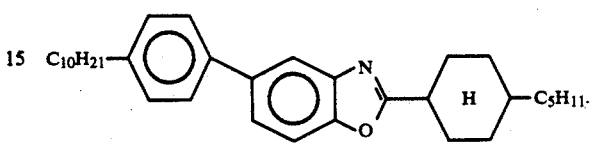

281. A composition according to claim 1, wherein said at least one mesomorphic compound has the formula:

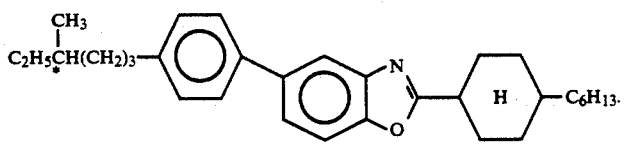

282. A composition according to claim 1, wherein said at least one mesomorphic compound has the formula:

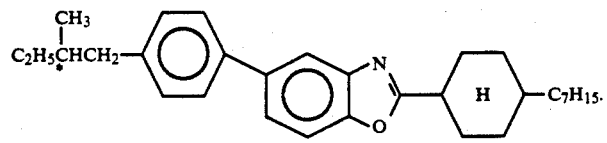

283. A composition according to claim 1, wherein said at least one mesomorphic compound has the formula:

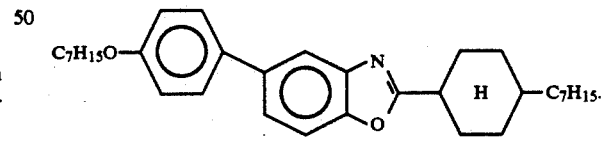

284. A composition according to claim 1, wherein said at least one mesomorphic compound has the formula:

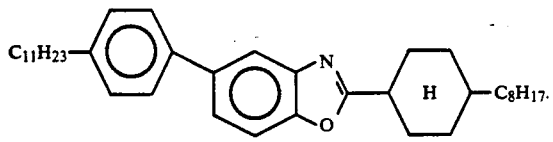

285. A composition according to claim 1, wherein said at least one mesomorphic compound has the formula:

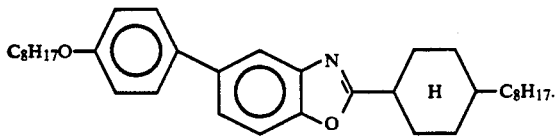

286. A composition according to claim 1, wherein said at least one mesomorphic compound has the formula:

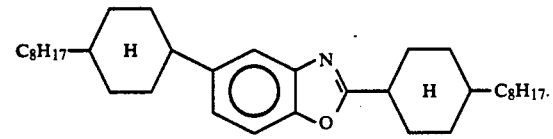

287. A composition according to claim 1, wherein said at least one mesomorphic compound has the formula:

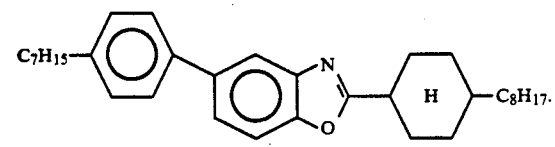

288. A composition according to claim 1, wherein said at least one mesomorphic compound has the formula:

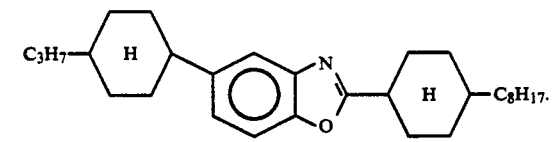

289. A composition according to claim 1, wherein said at least one mesomorphic compound has the formula:

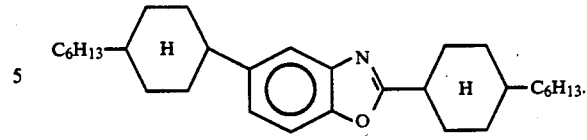

290. A composition according to claim 1, wherein said at least one mesomorphic compound has the formula:

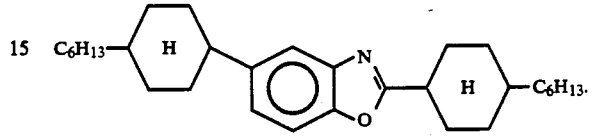

291. A composition according to claim 1, wherein said at least one mesomorphic compound has the formula:

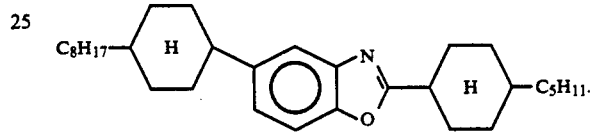

292. A composition according to claim 1, wherein said at least one mesomorphic compound has the formula:

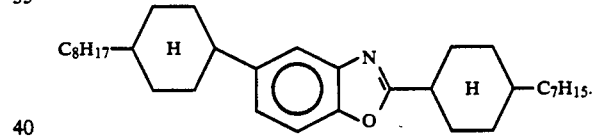

293. A composition according to claim 1, wherein said at least one mesomorphic compound has the formula:

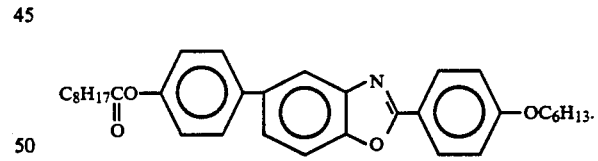

294. A composition according to claim 1, wherein said at least one mesomorphic compound has the formula:

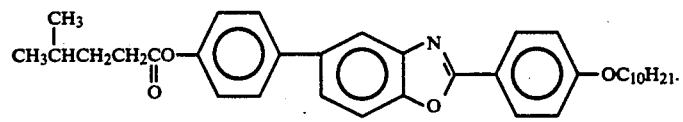

295. A composition according to claim 1, wherein said at least one mesomorphic compound has the formula:

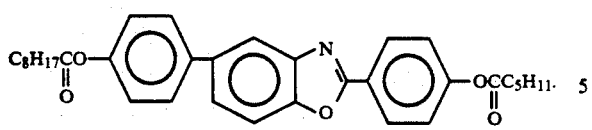

296. A composition according to claim 1, wherein said at least one mesomorphic compound has the formula:

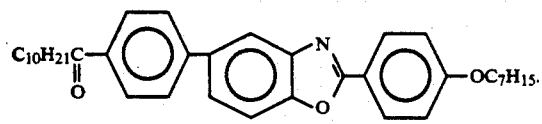

297. A composition according to claim 1, wherein said at least one mesomorphic compound has the formula:

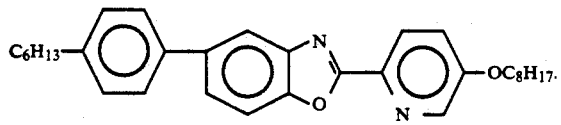

298. A composition according to claim 1, wherein said at least one mesomorphic compound has the formula:

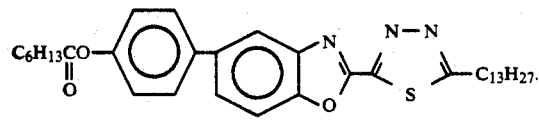

299. A composition according to claim 1, wherein said at least one mesomorphic compound has the formula:

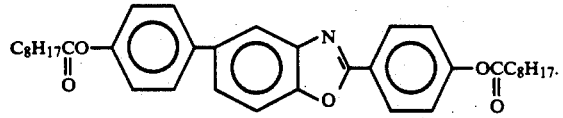

300. A composition according to claim 1, wherein said at least one mesomorphic compound has the formula:

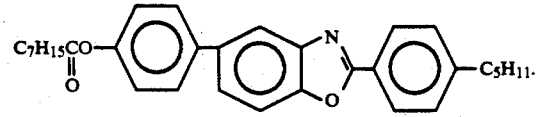

301. A liquid crystal device, comprising a pair of electrode plates and a liquid crystal composition according to claim 1 disposed between the electrode plates.

302. A mesomorphic composition according to claim 2, wherein the n-alkyl group in said at least one mesomorphic compound has 3–12 carbon atoms.

303. A liquid crystal device according to claim 301, which contains 1–500 wt. parts of said mesomorphic compound of the formula (I) per 100 wt. parts of at least one type of another mesomorphic compound.

304. A liquid crystal device according to claim 301, which contains 2–100 wt. parts of said mesomorphic compound of the formula (I) per 100 wt. parts of at least one type of another mesomorphic compound.

305. A liquid crystal composition comprising at least two mesomorphic compounds, at least one of said mesomorphic compounds being a mesomorphic compound represented by a formula selected from the group consisting of:

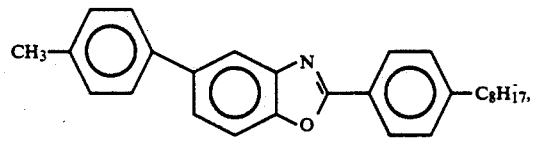

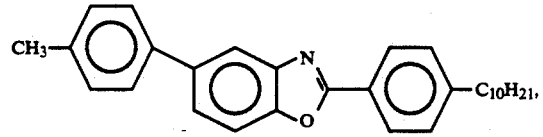

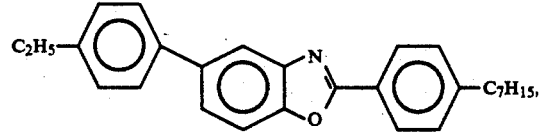

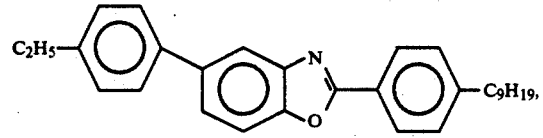

-continued
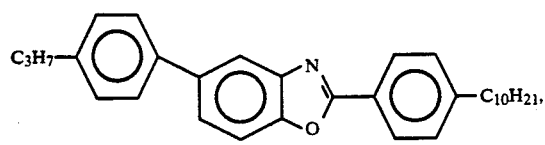
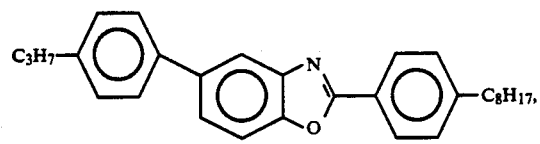
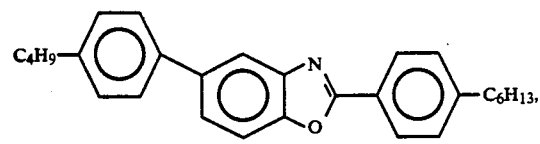
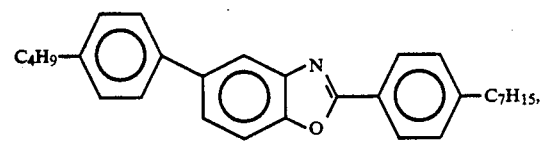
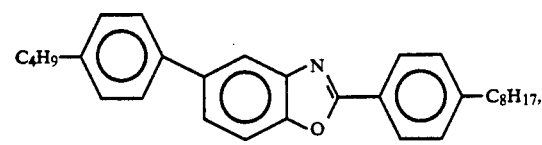
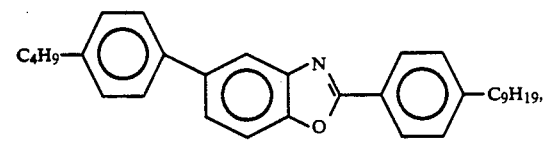
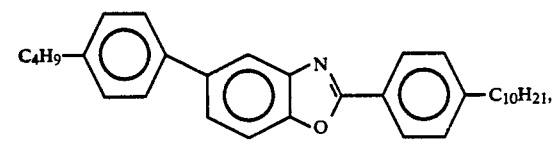
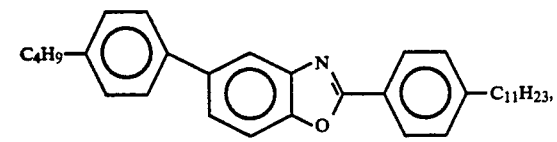
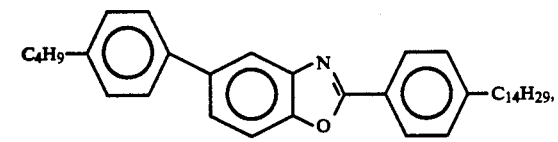
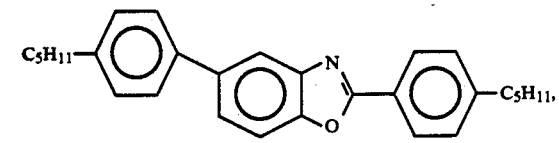

-continued
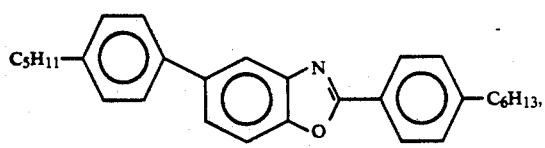
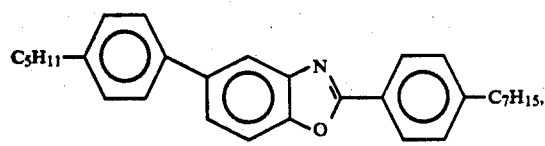
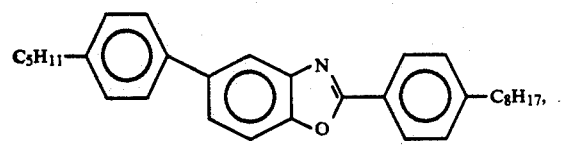
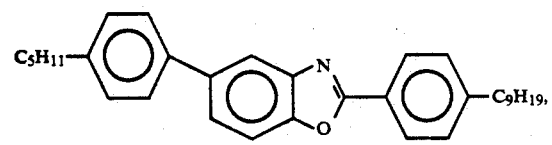
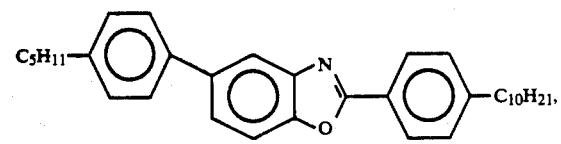
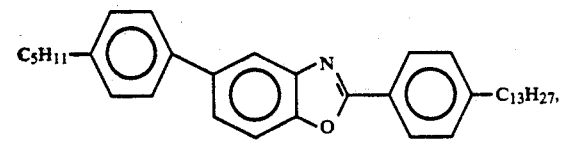
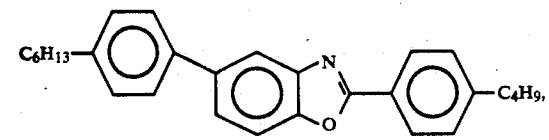
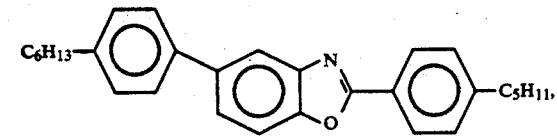
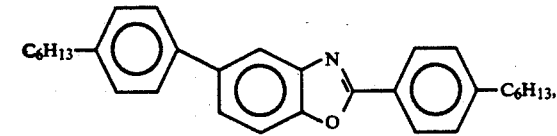
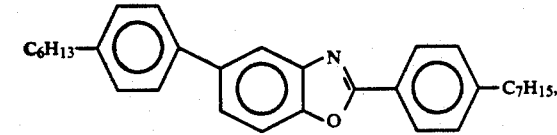

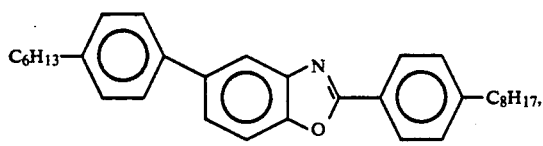
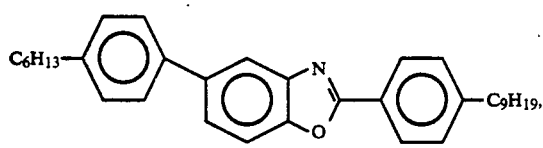
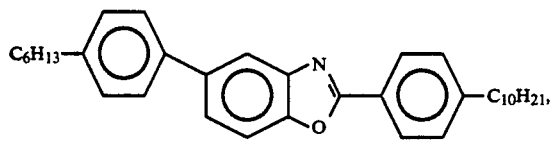
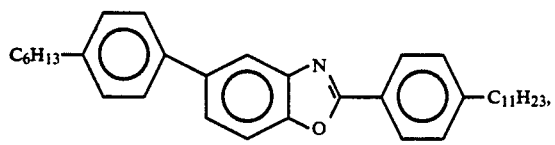
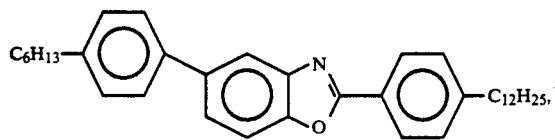
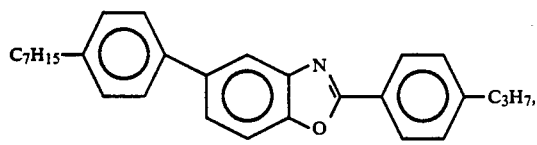
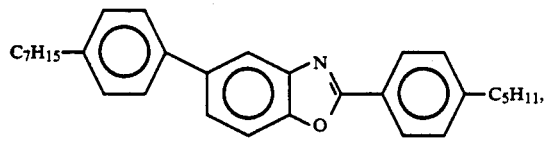
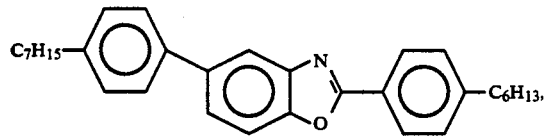
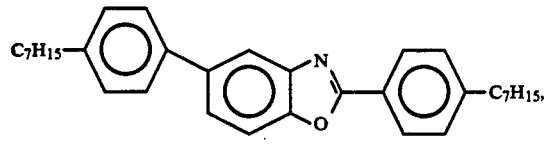
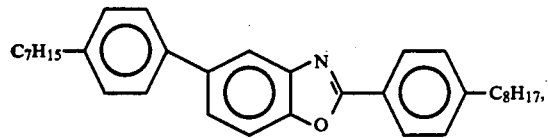

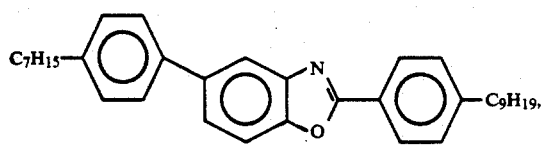
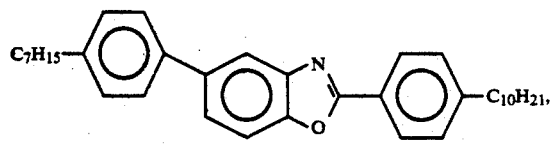
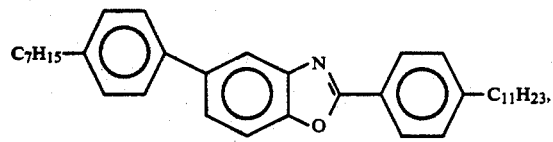
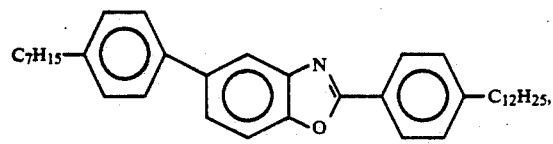
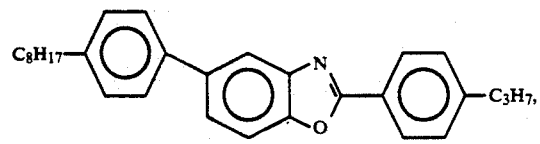
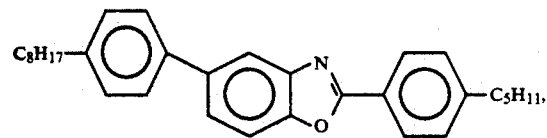
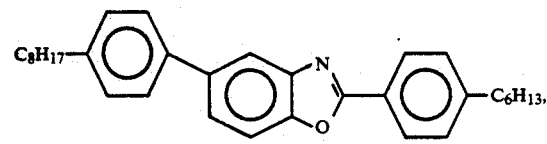
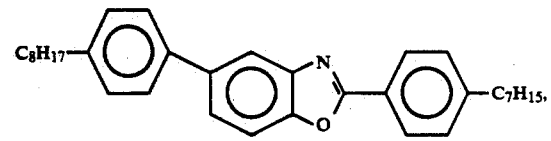
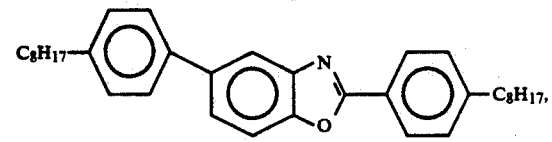
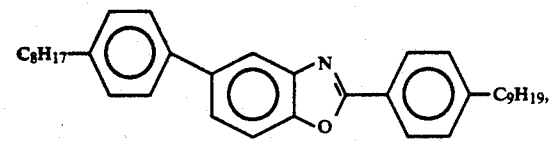

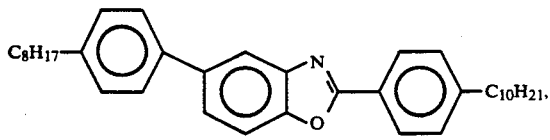
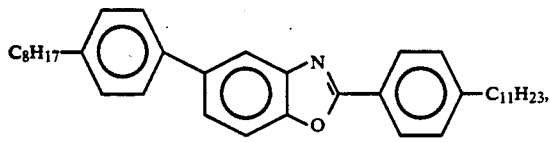
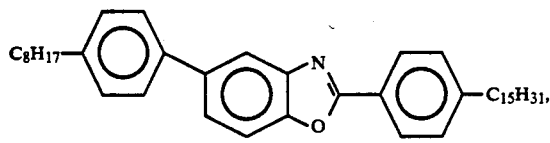
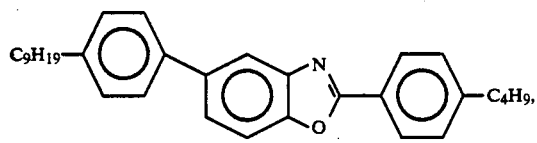
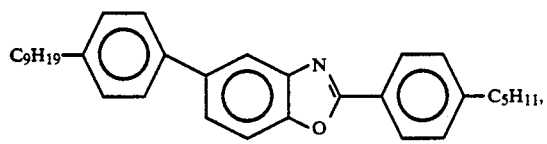
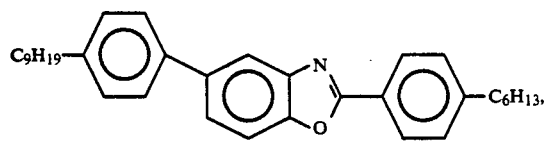
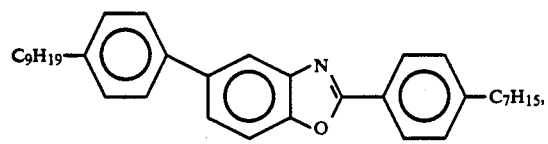
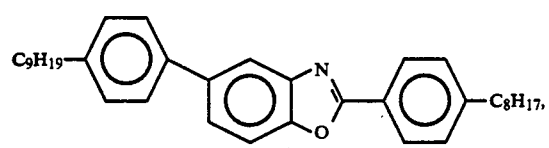
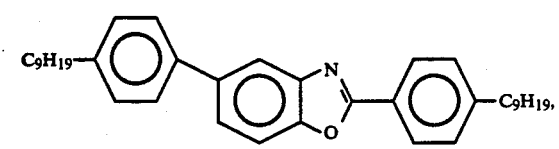
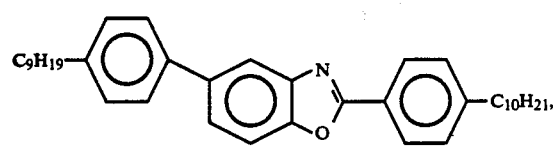

-continued
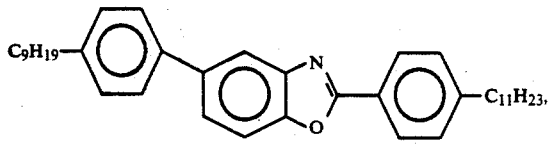
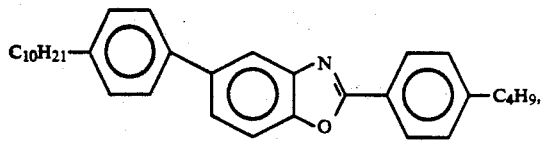
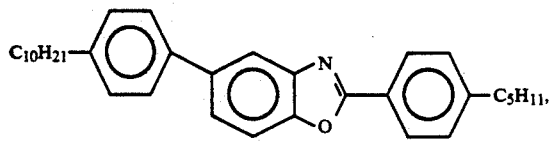
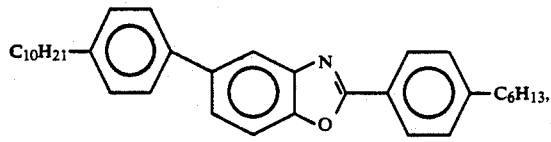
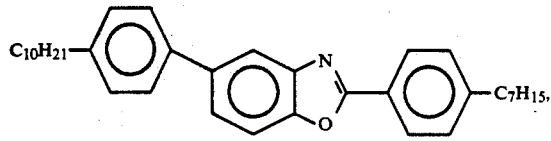
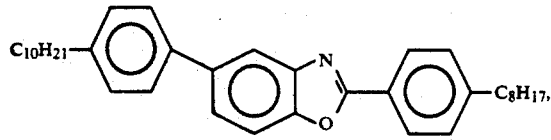
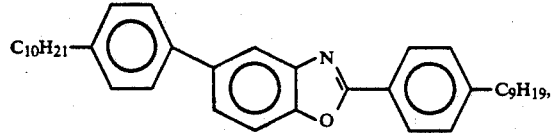
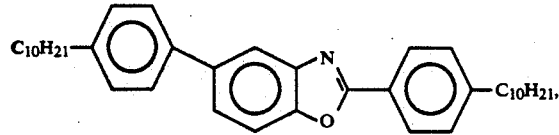
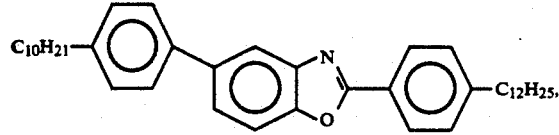
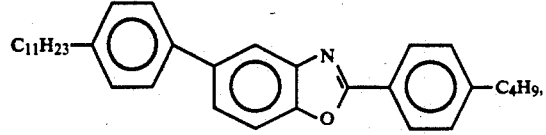

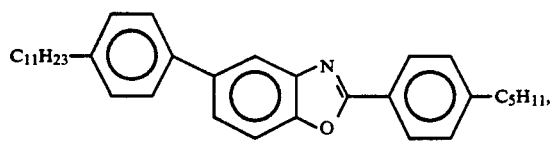
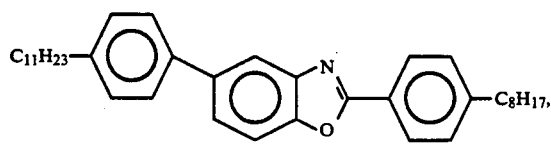
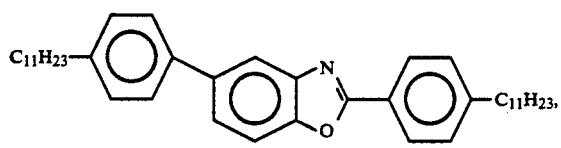
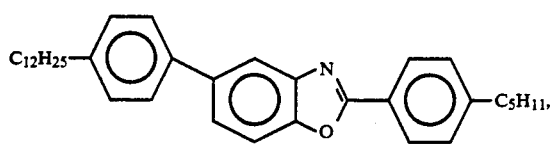
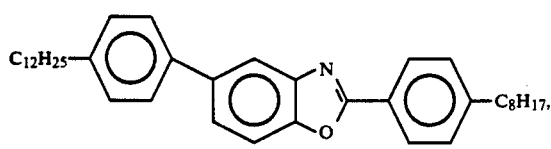
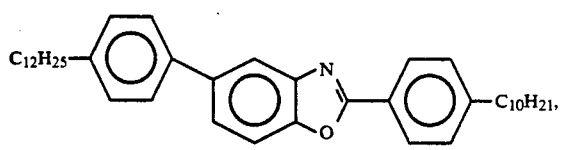
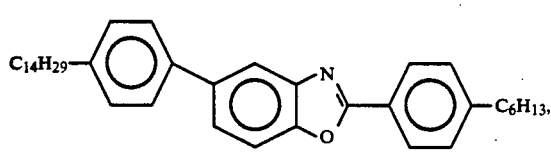
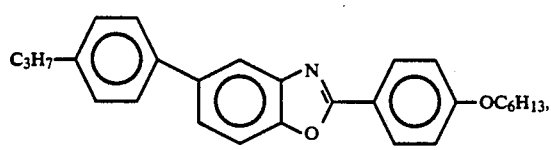
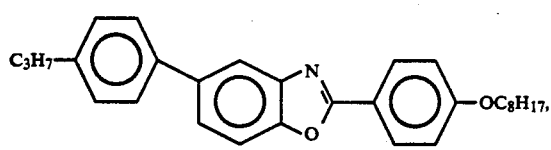
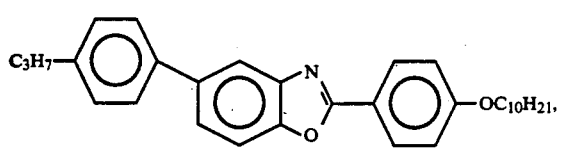

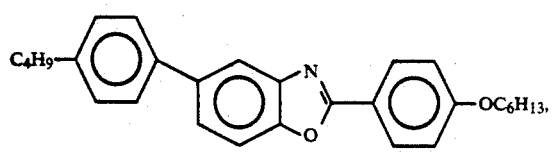
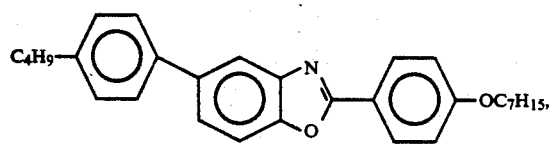
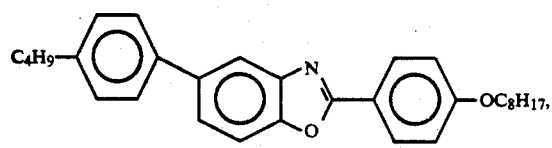
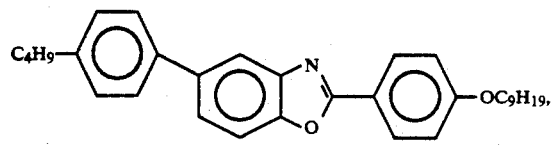
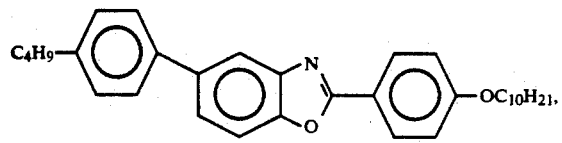
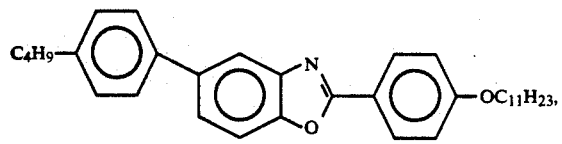
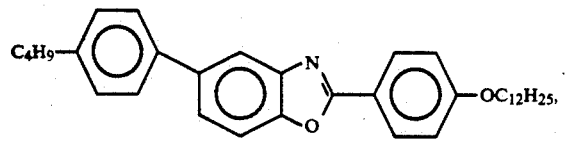
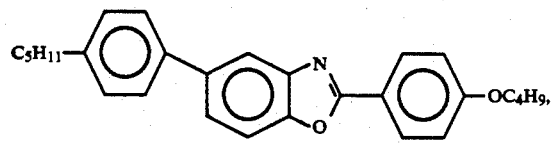
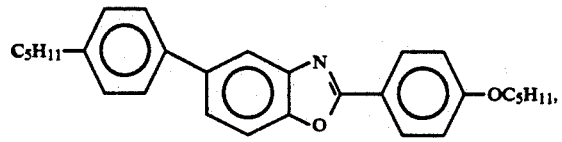
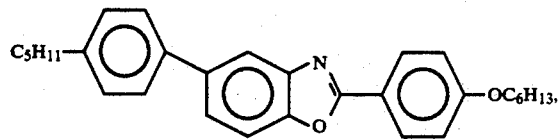

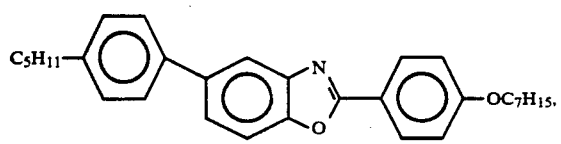
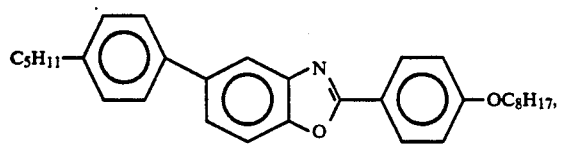
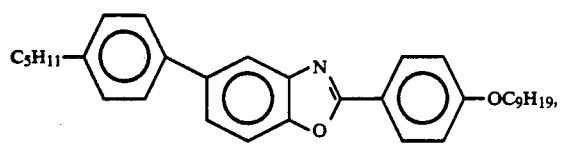
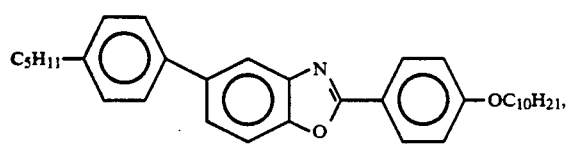
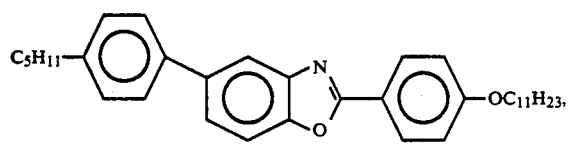
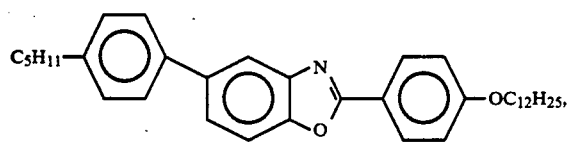
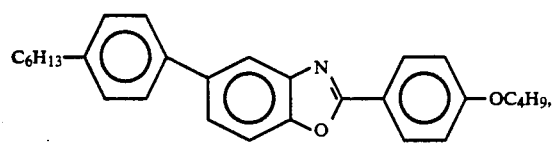
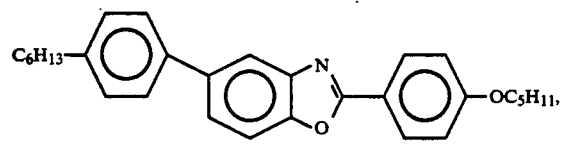
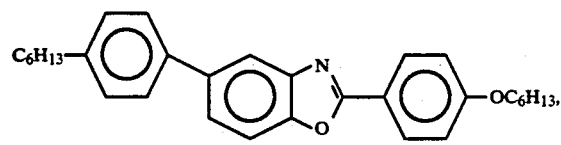
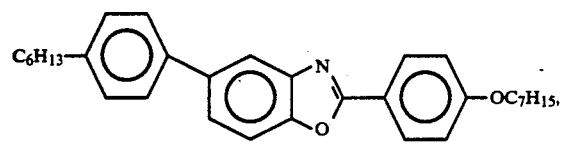

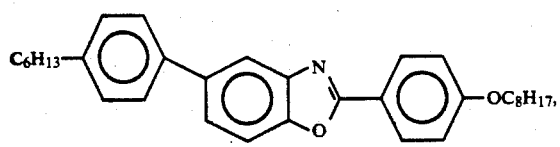
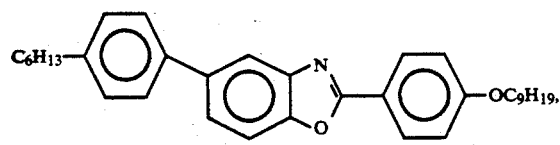
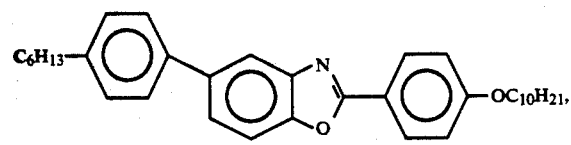
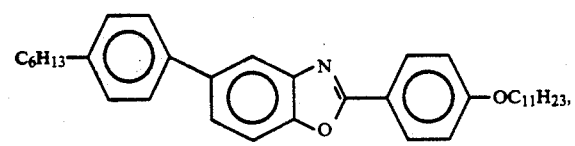
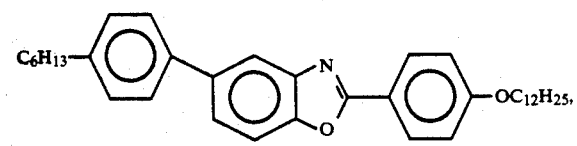
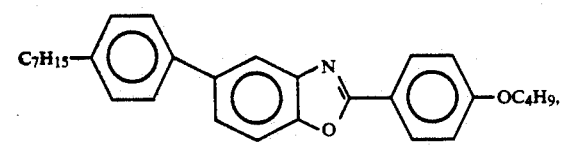
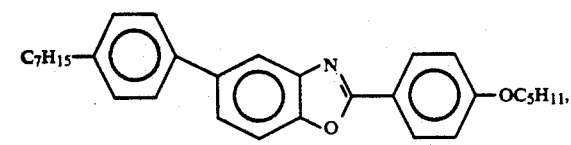
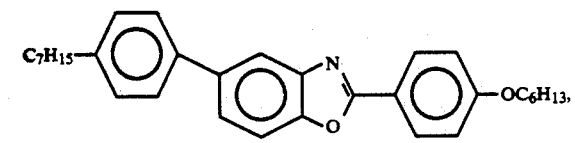
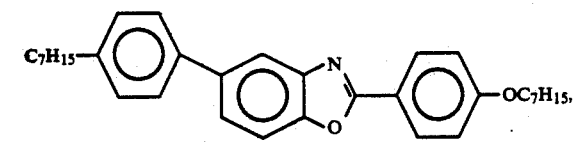
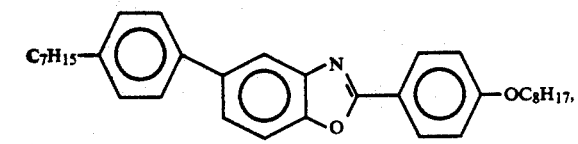

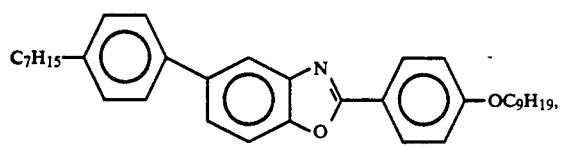
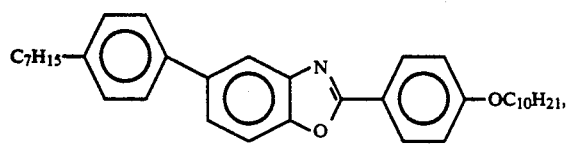
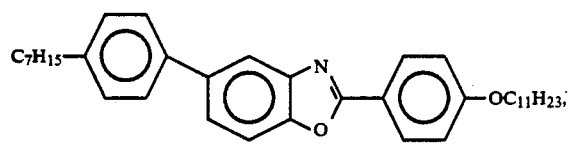
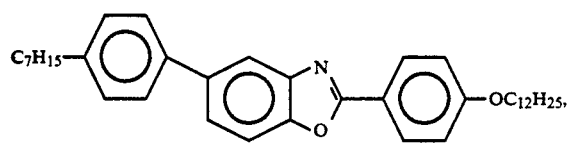
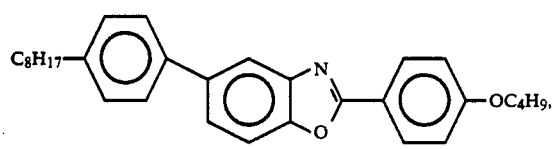
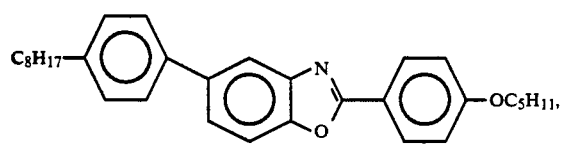
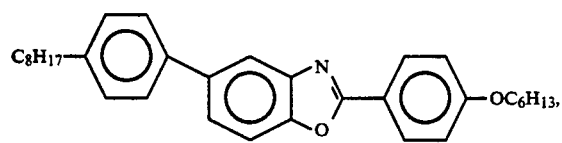
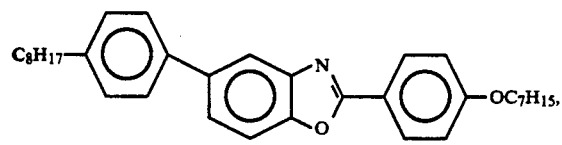
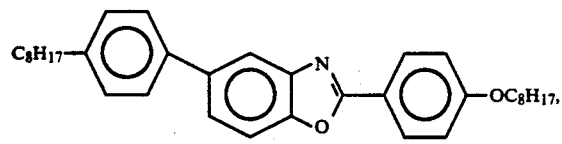
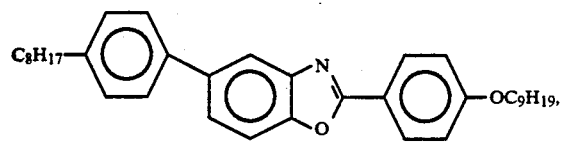

-continued
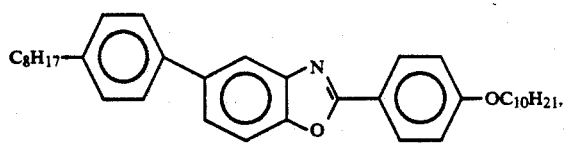
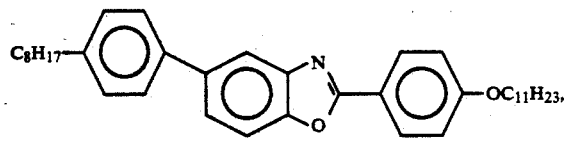
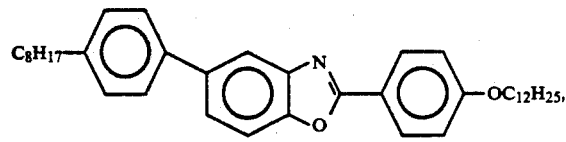
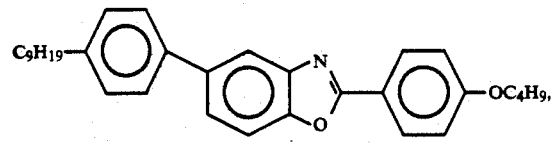
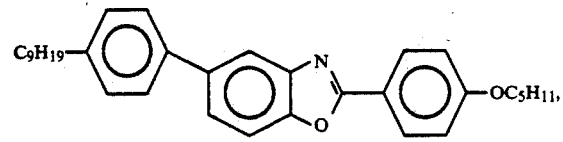
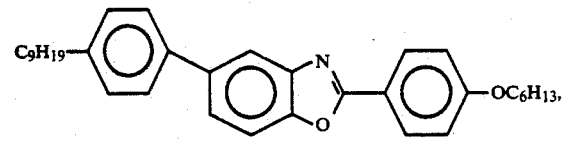
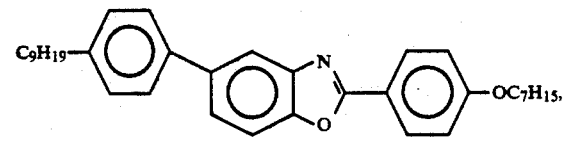
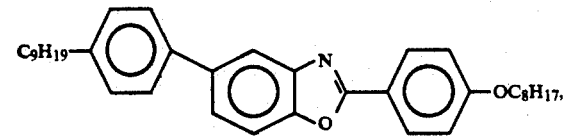
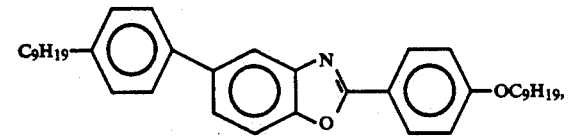
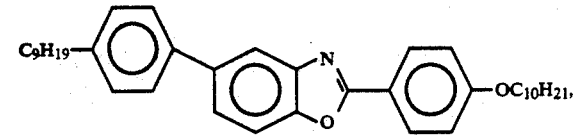

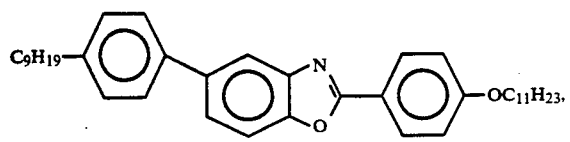
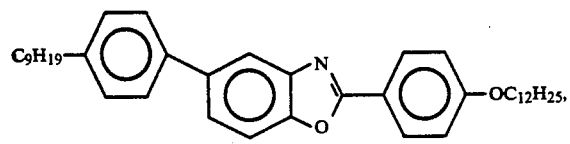
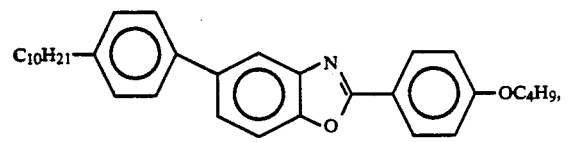
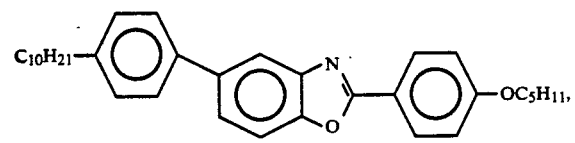
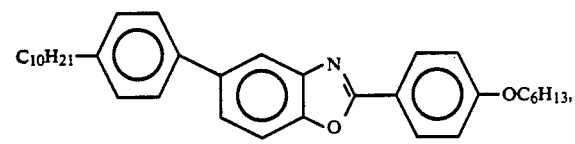
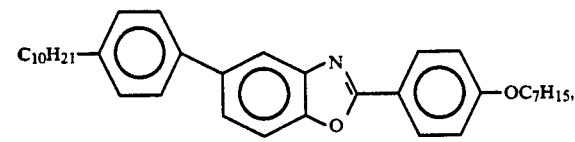
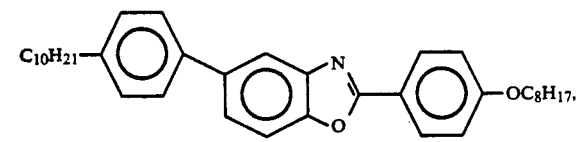
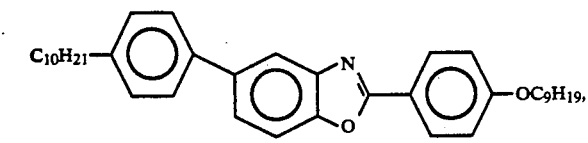
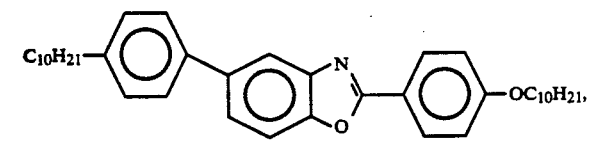
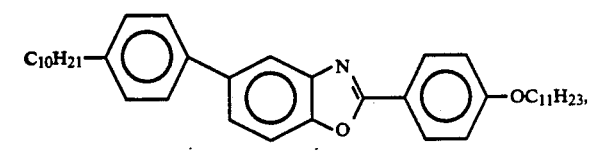

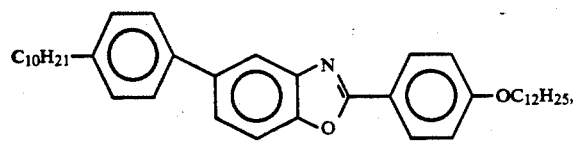
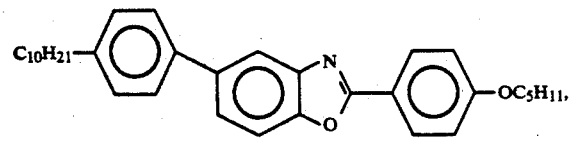
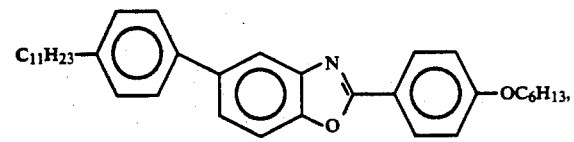
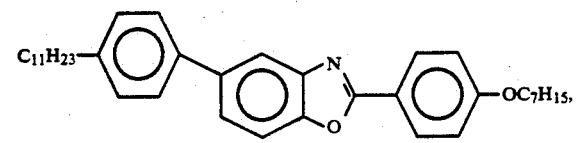
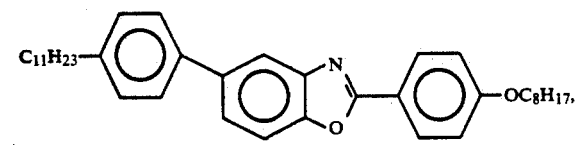
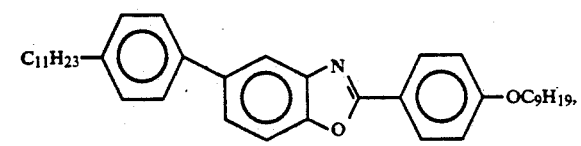
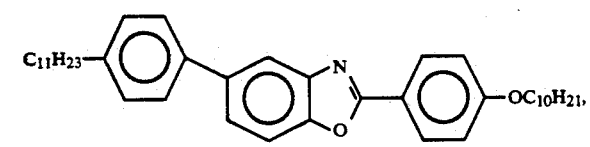
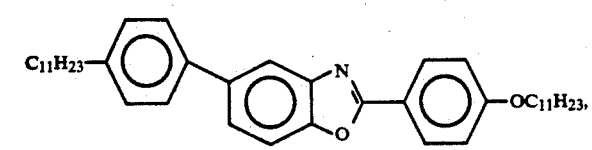
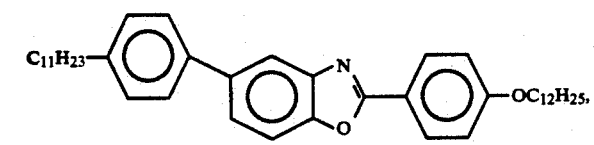
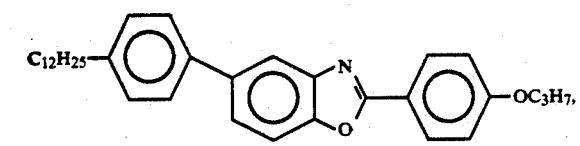

-continued
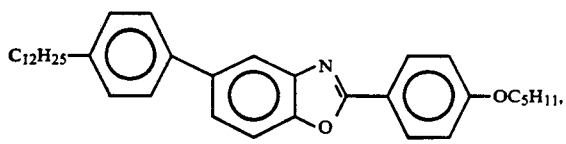
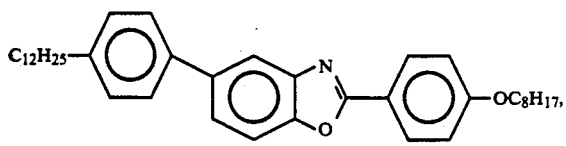
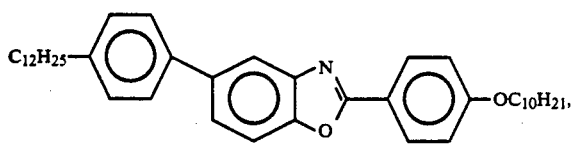
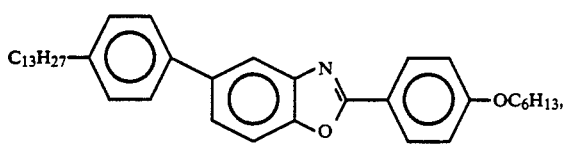
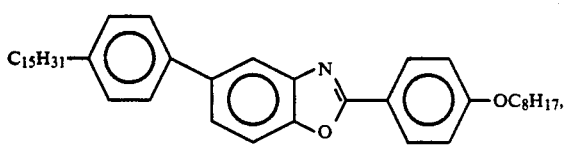
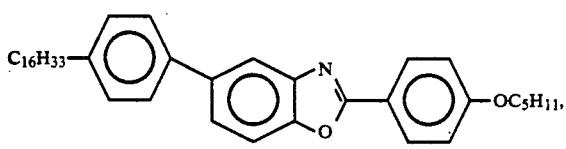
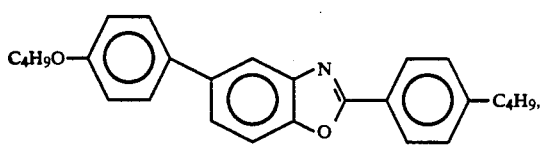
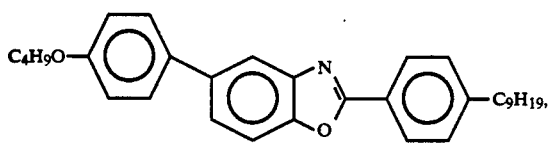
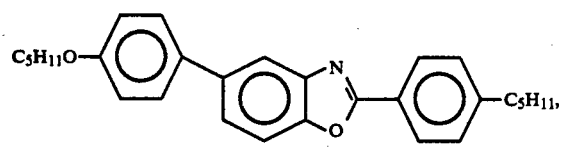
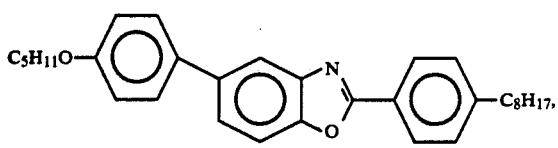

-continued
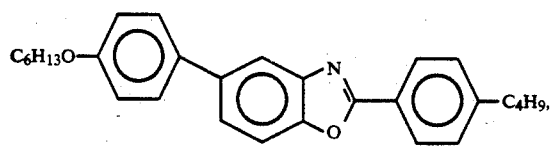
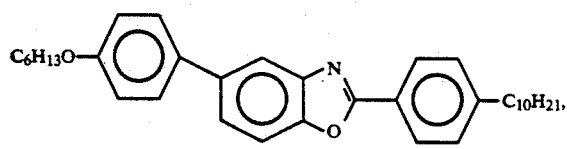
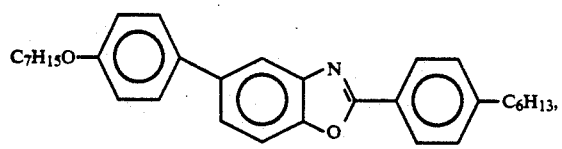
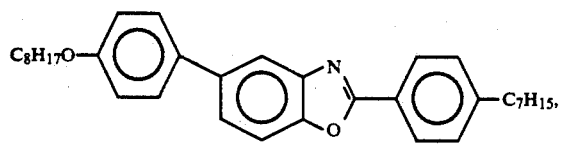
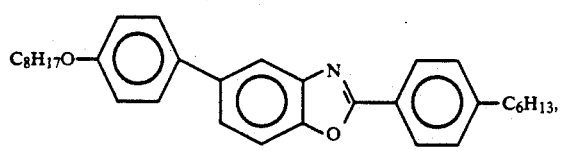
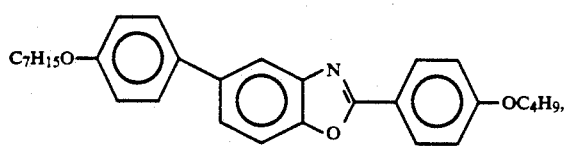
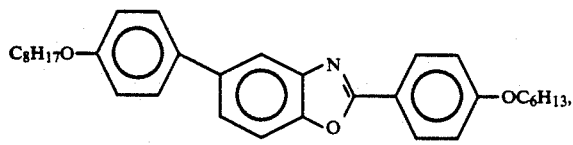
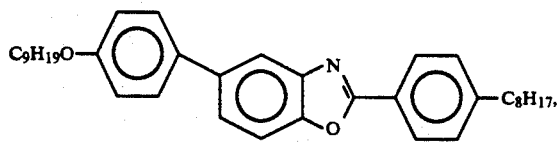
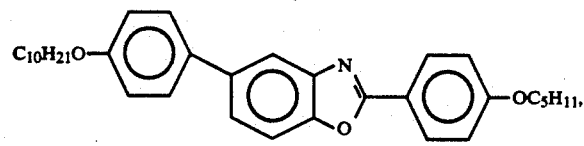
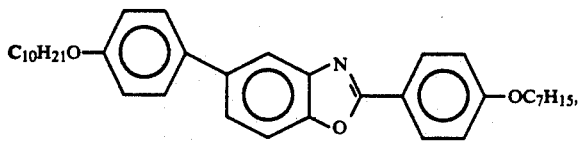

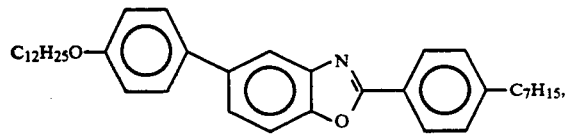
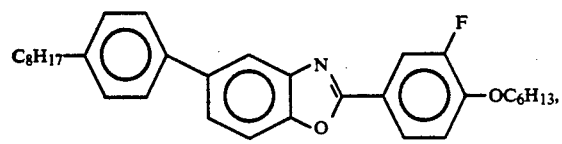
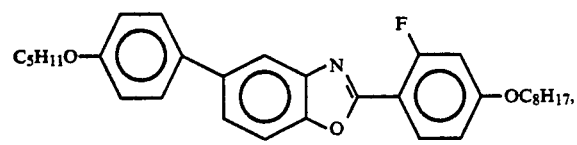
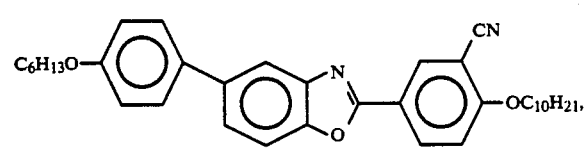
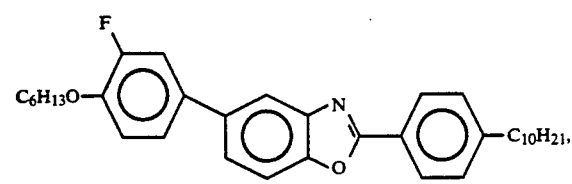
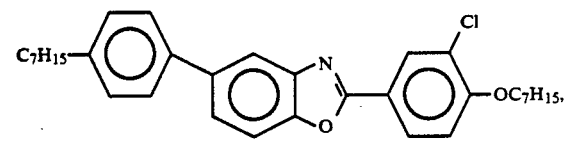
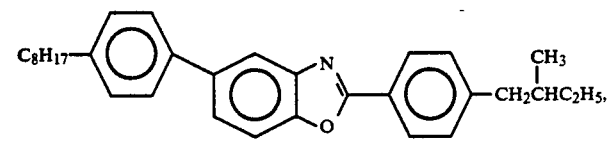
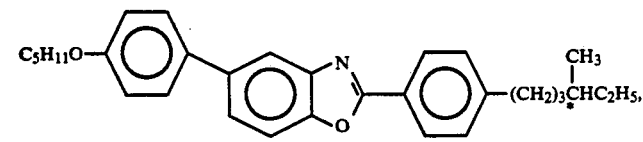
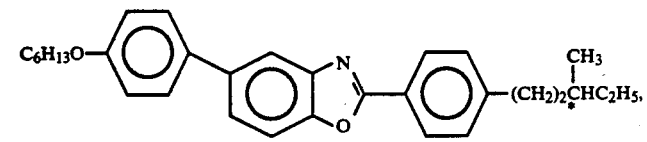
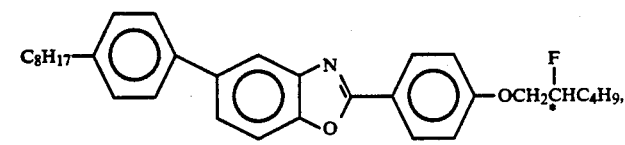

-continued
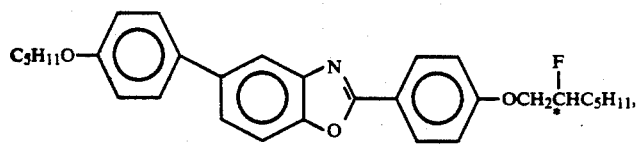
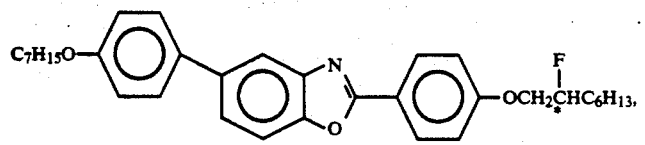
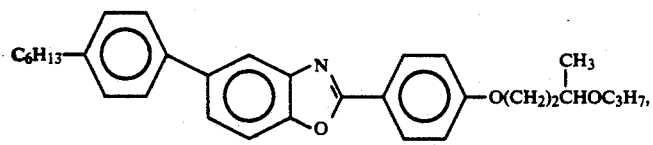
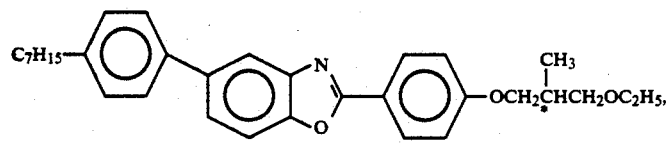
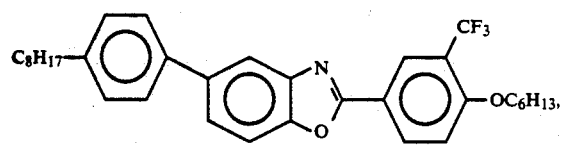
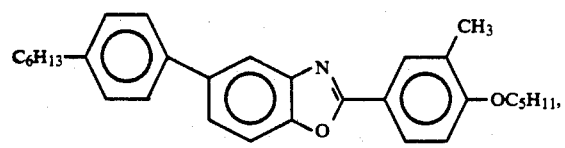
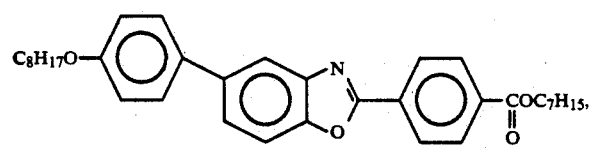
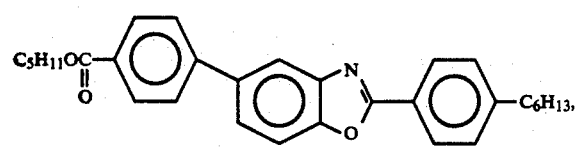
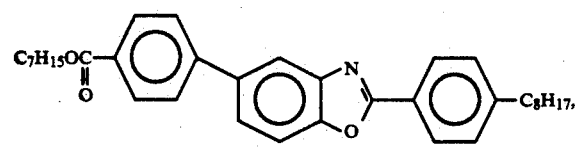
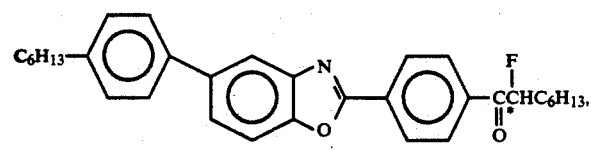

-continued
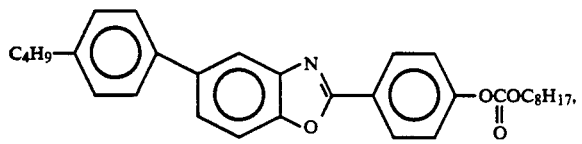
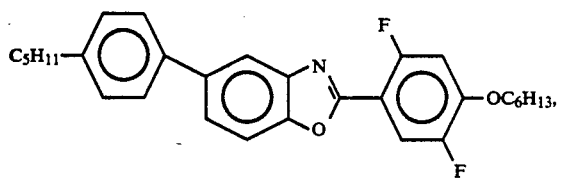
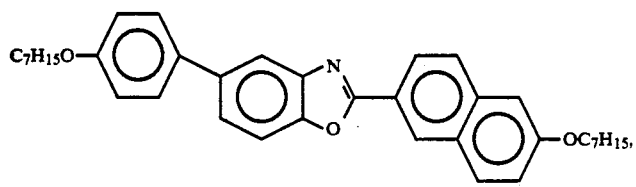
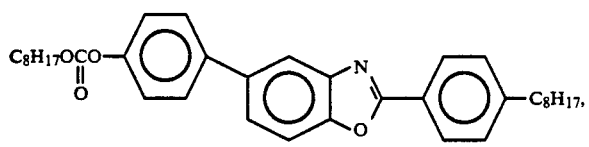
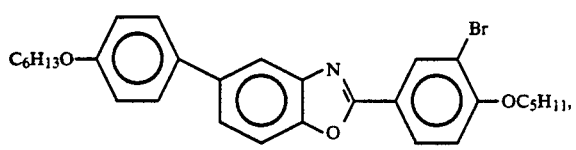
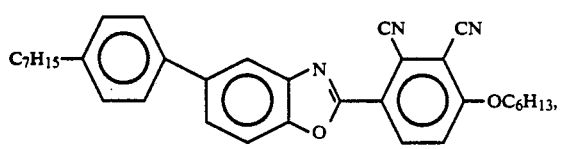
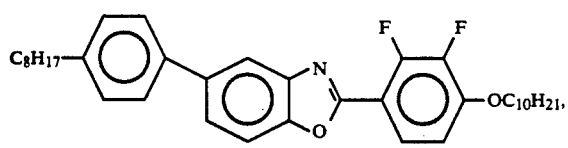
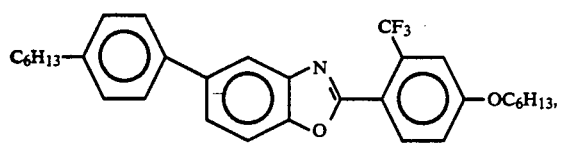
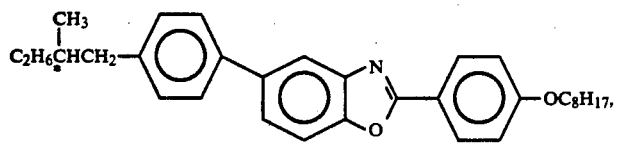
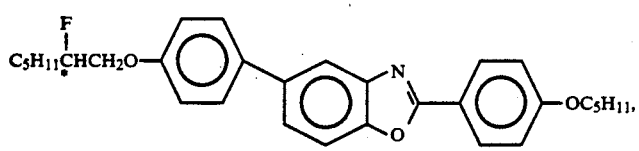

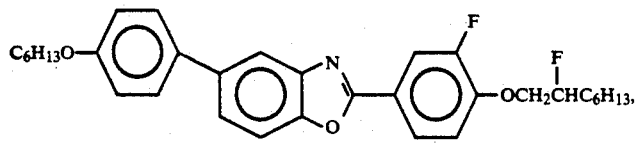
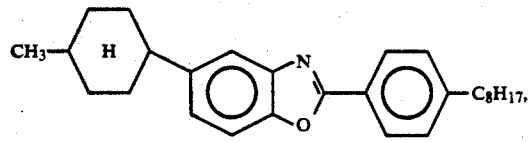
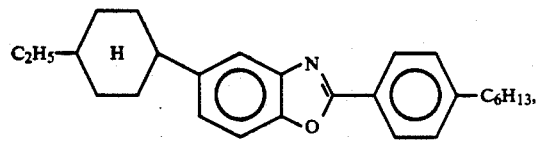
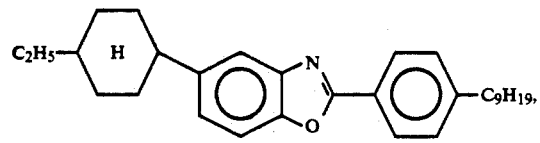
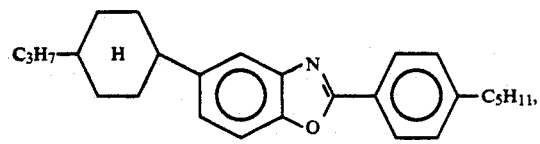
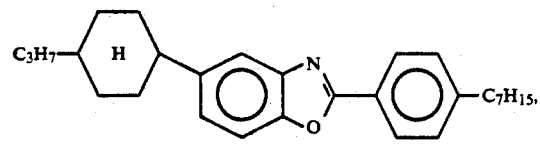
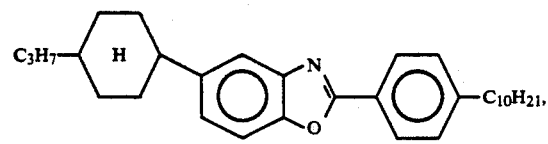
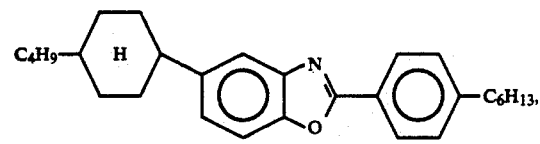
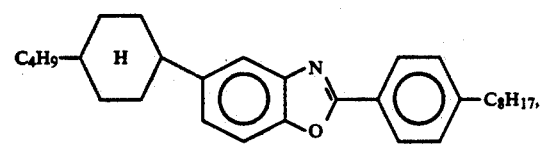
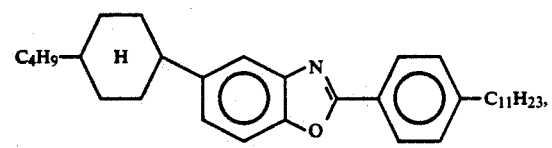

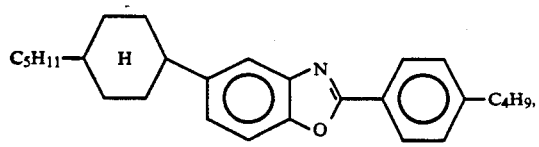
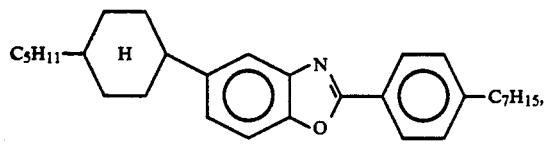
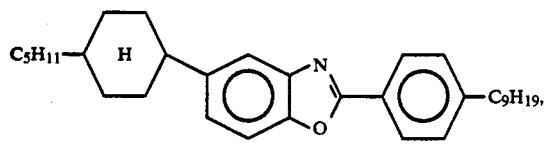
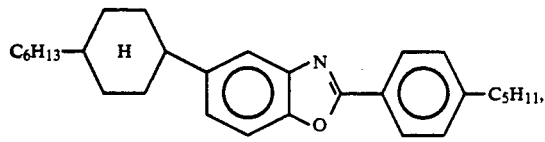
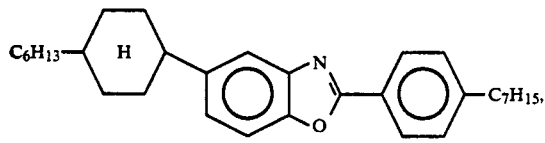
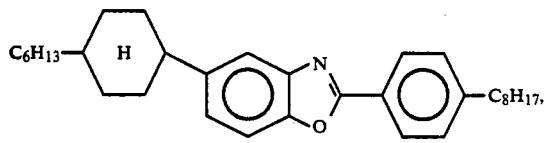
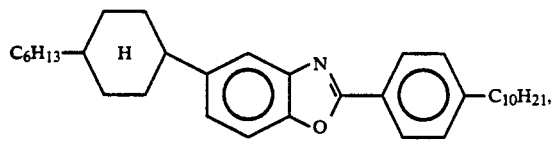
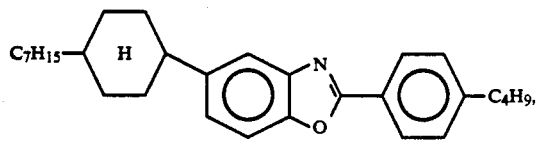
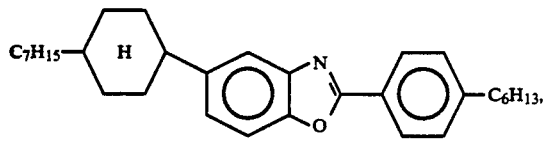
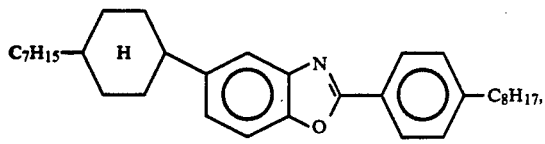

-continued
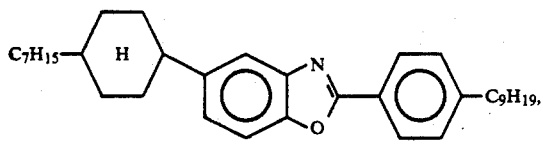
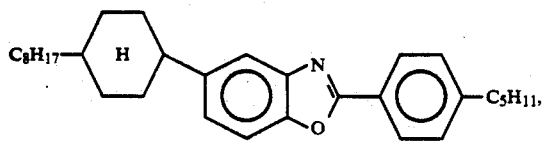
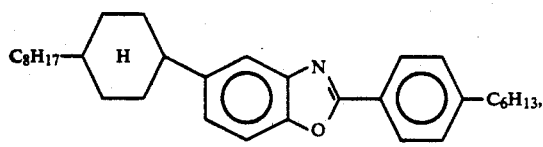
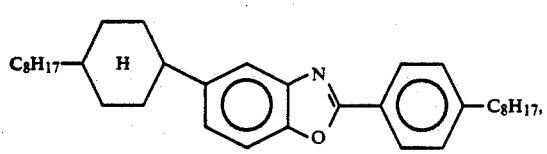
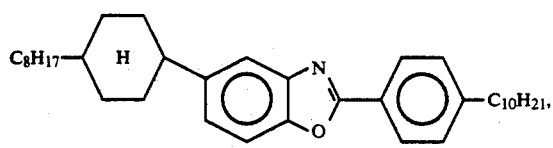
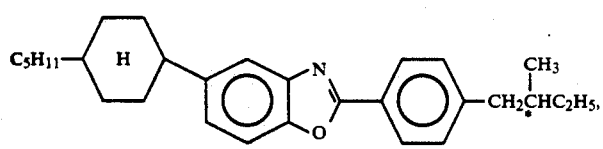
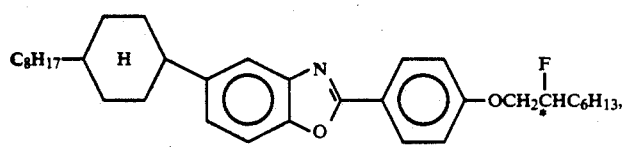
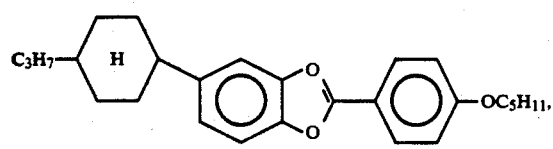
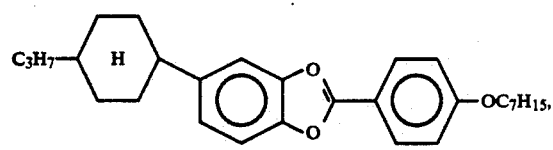
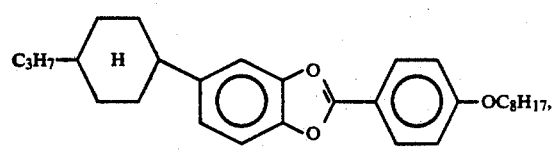

-continued
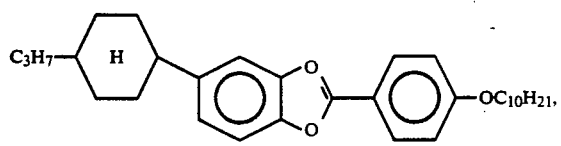
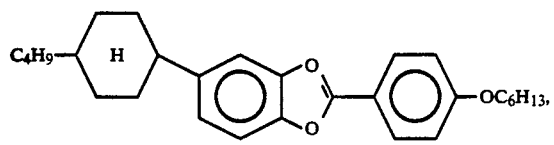
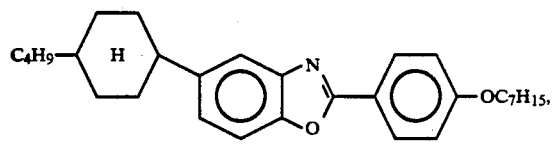
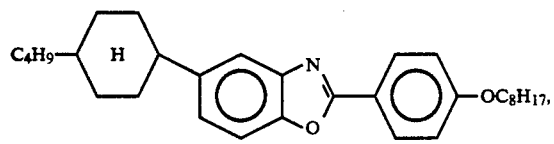
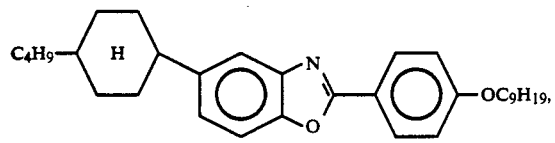
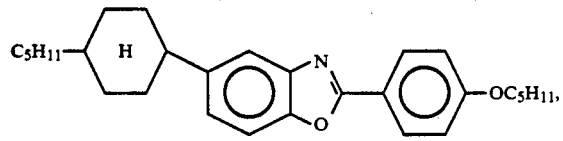
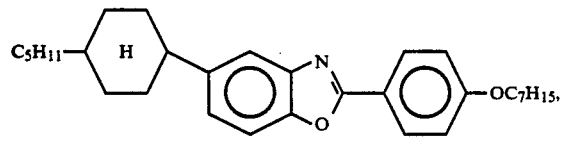
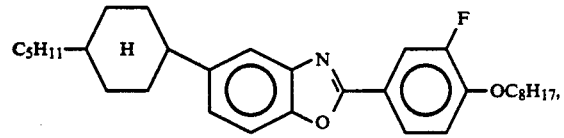
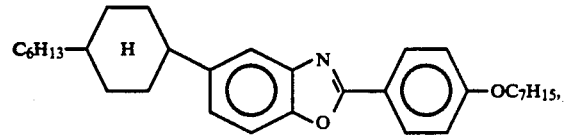
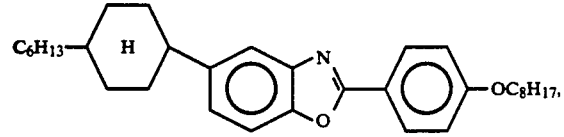

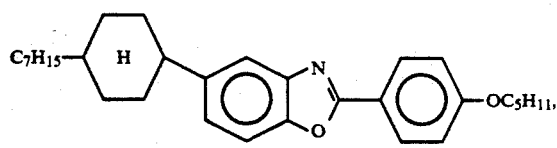
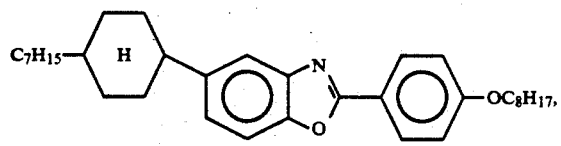
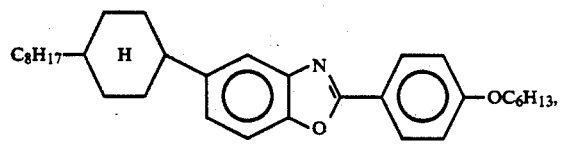
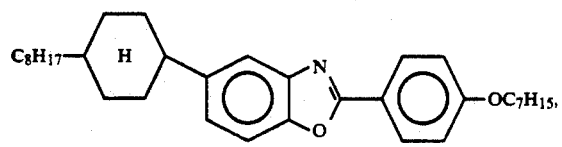
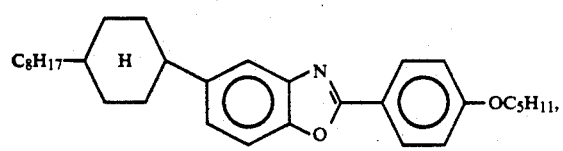
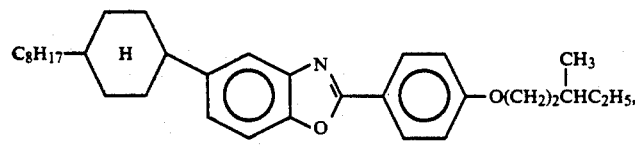
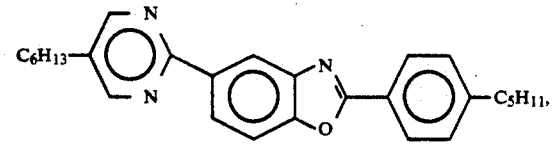
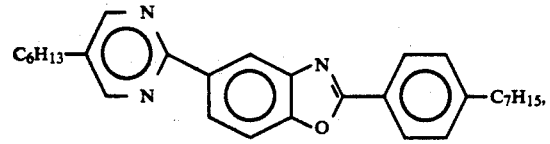
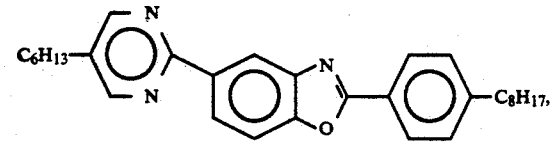
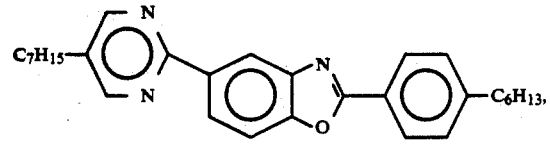

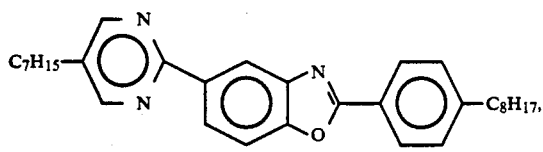
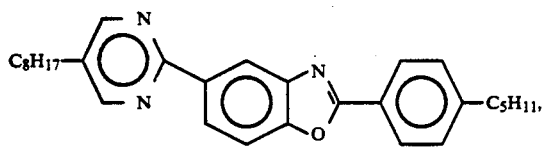
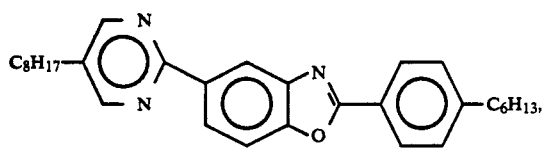
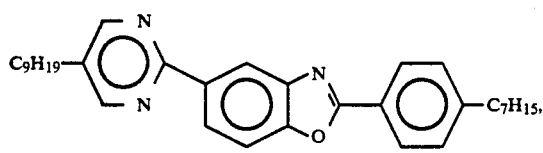
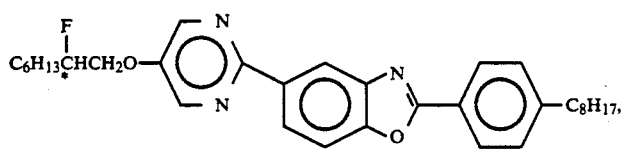
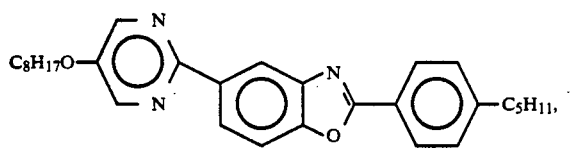
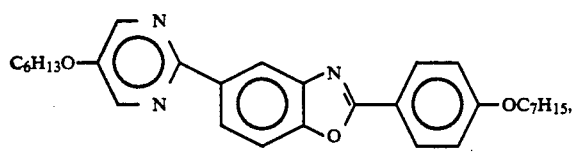
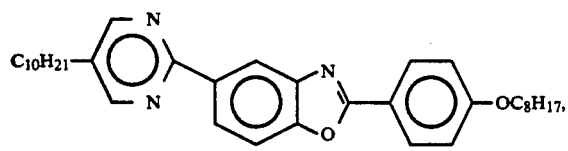
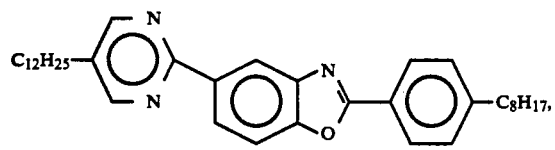
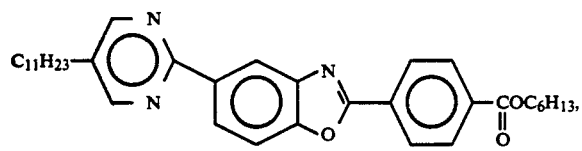

-continued
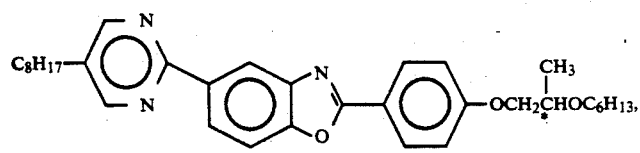
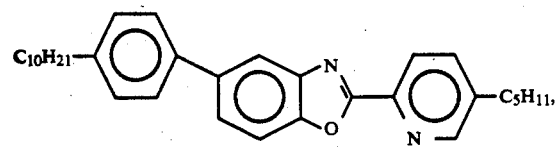
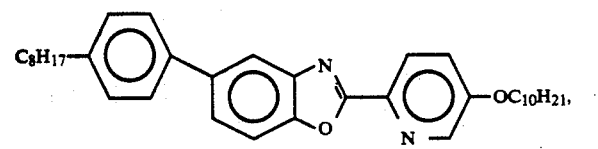
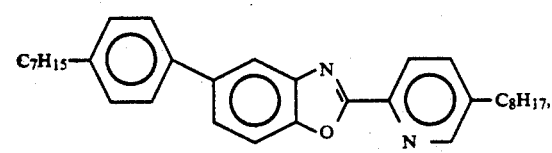
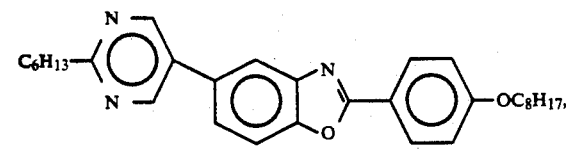
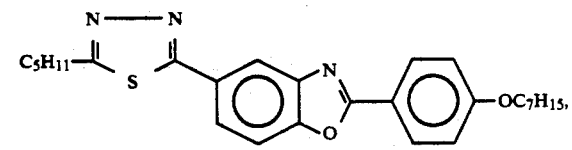
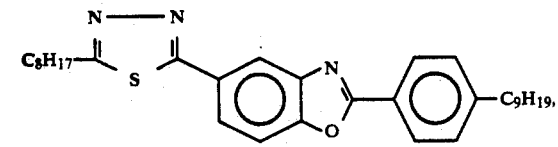
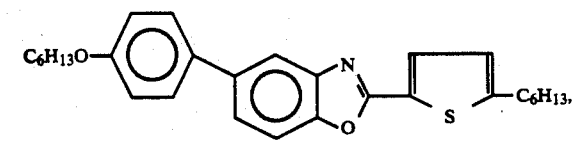
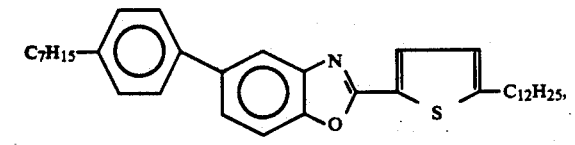
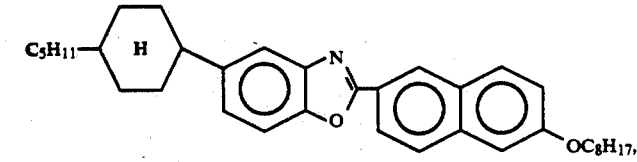

-continued
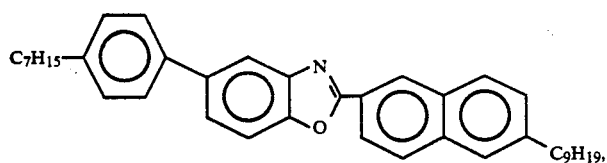
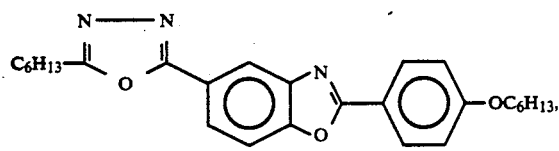
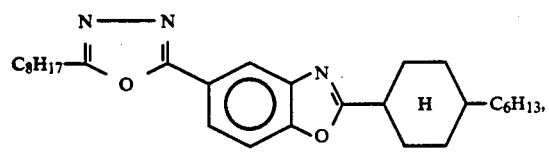
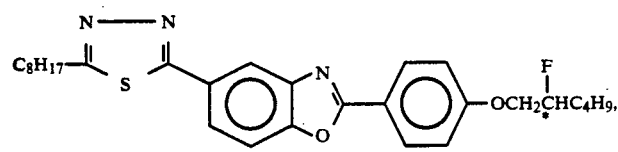
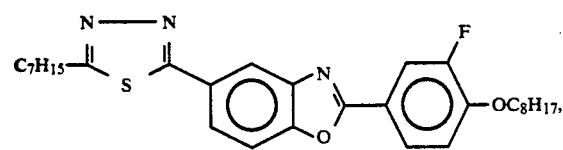
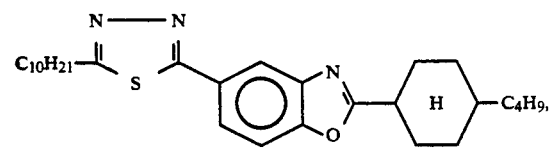
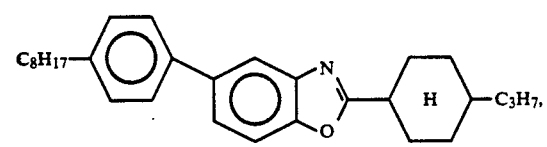
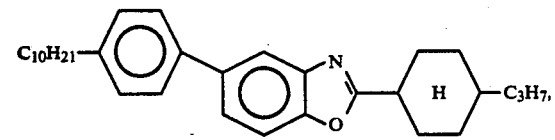
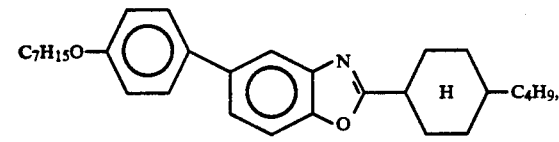
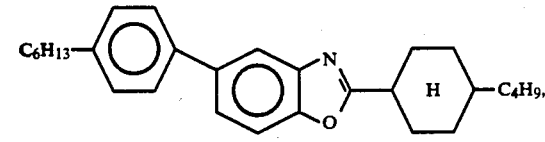

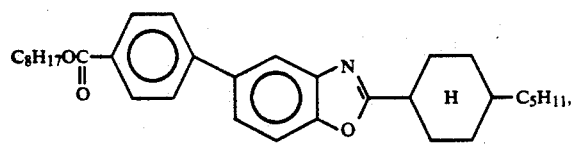
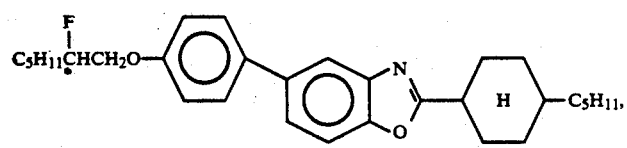
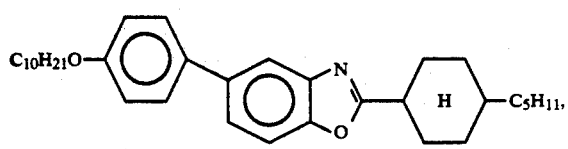
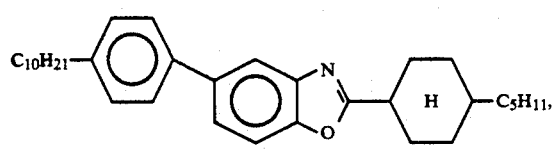
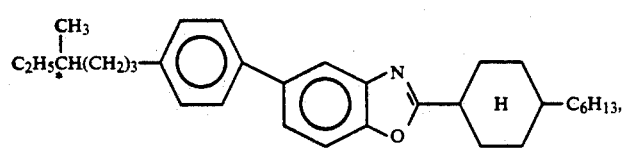
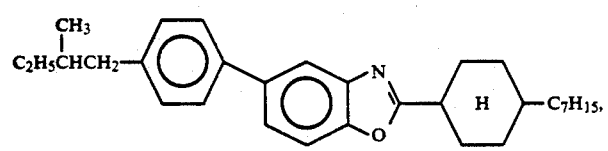
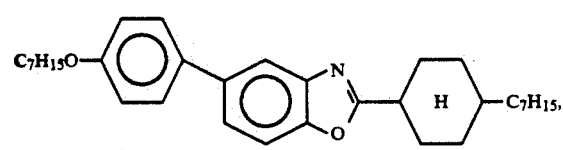
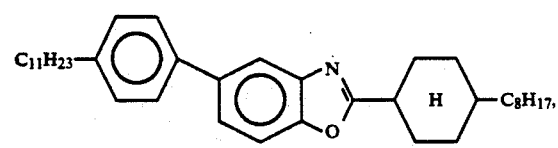
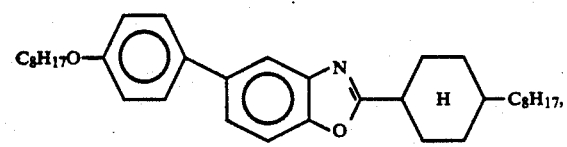
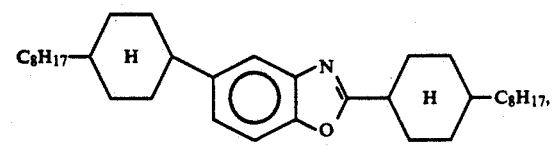

-continued
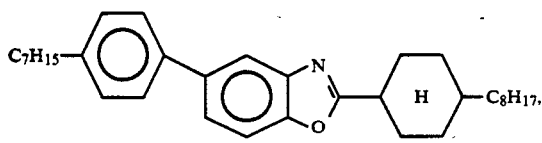
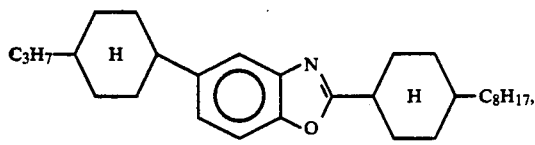
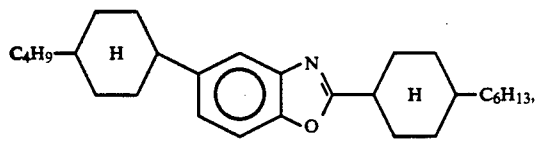
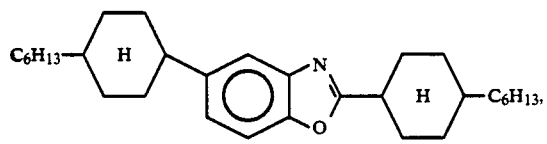
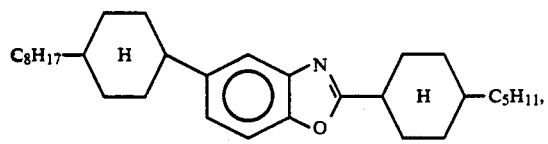
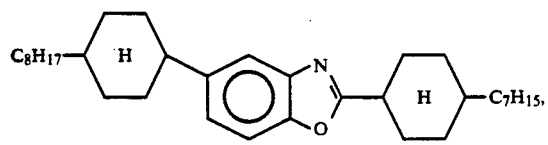
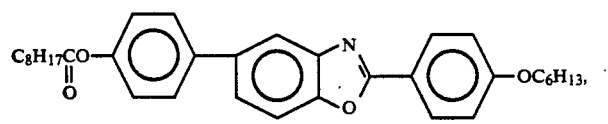
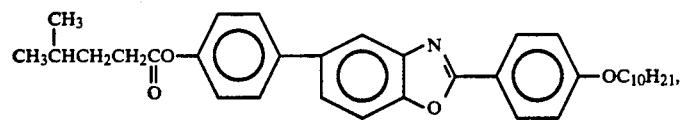
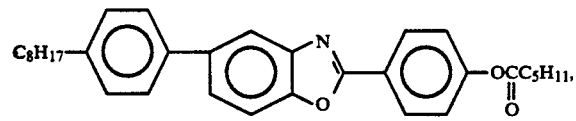
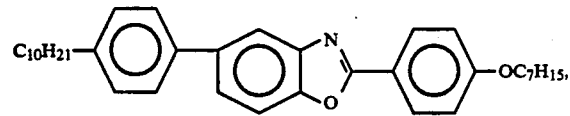
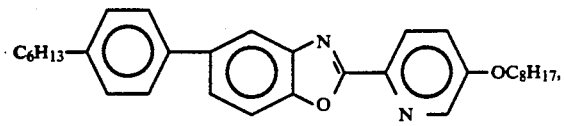

-continued
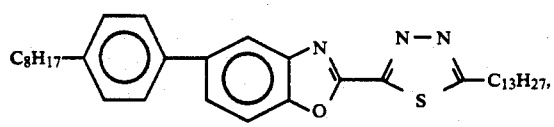
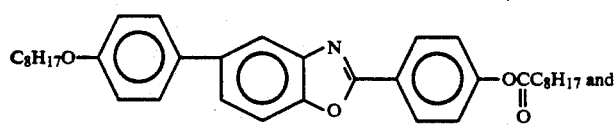
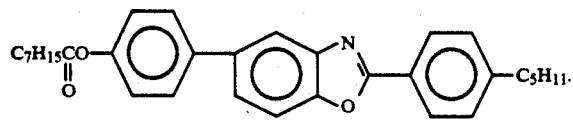
306. A liquid crystal device comprising a pair of electrode plates and a liquid crystal composition according to claim 305 disposed between the electrode plates.

UNITED STATES PATENT AND TRADEMARK OFFICE
CERTIFICATE OF CORRECTION

PATENT NO. : 5,190,690
DATED : March 2, 1993
INVENTOR(S) : TAKAO TAKIGUCHI, ET AL.

Page 1 of 4

It is certified that error appears in the above-identified patent and that said Letters Patent is hereby corrected as shown below:

On title page, item

[56] REFERENCES CITED

Under FOREIGN PATENT DOCUMENTS, insert:
 --156046  8/1985  Japan .--.

COLUMN 5

Line 5, "$R_2-X_2-Z_2-\overset{\overset{O}{\|}}{C}Cl$" should --$R_2-X_2-A_2-\overset{\overset{O}{\|}}{C}Cl$--.

Line 28, "respectively" should be deleted.

COLUMN 6

Line 53, "1-12) optically" should read --1-12 (optically--.
Line 54, "inactive;" should read --inactive);--.

COLUMN 39

Formula (1-162), "$OC_8H_{17}$" should read --$C_8H_{17}$--.

COLUMN 51

Formula (1-224), "$OC_7H_{17}$" should read --$OC_8H_{17}$--.

COLUMN 65

Formula (1-298), "$O\overset{\overset{}{}}{\underset{\underset{O}{\|}}{C}}C_5H_{11}$" should read --$C_5H_{11}$--.

UNITED STATES PATENT AND TRADEMARK OFFICE
CERTIFICATE OF CORRECTION

PATENT NO. : 5,190,690
DATED : March 2, 1993
INVENTOR(S) : TAKAO TAKIGUCHI, ET AL.

It is certified that error appears in the above-identified patent and that said Letters Patent is hereby corrected as shown below:

COLUMN 93

Formula (179), "$C_6H_{13}$" should read --$C_6H_{13}O$--.
Formula (180), "$C_8H_{17}$" should read --$C_8H_{17}O$--.
Formula (181), "$C_9H_{19}$" should read --$C_9H_{19}O$--.
Formula (182), "$C_{11}H_{23}$" should read --$C_{11}H_{23}O$--.

COLUMN 97

Formula (206), "$C_7H_{15}$" should read --$OC_7H_{15}$--.
Formula (207), "$C_5H_{11}$" should read --$OC_5H_{11}$--.
Formula (208), "$C_6H_{13}$" should read --$OC_6H_{13}$--.

COLUMN 103

Formula (240), "$CH_2O$-⟨◯⟩" should read --⟨◯⟩-$CH_2O$--.

Formula (246), "$CH_2\overset{*}{C}HC_2H_5$" should read --"$OCH_2\overset{*}{C}HC_2H_5$--.

COLUMN 105

Line 11, "form" should read --from--.

COLUMN 106

Line 26, "(P) 24" should read --(P⊥) 24--.

COLUMN 107

Line 31, "Step i)" should read --¶ Step i)--.

UNITED STATES PATENT AND TRADEMARK OFFICE
CERTIFICATE OF CORRECTION

PATENT NO. : 5,190,690

DATED : March 2, 1993

INVENTOR(S) : TAKAO TAKIGUCHI, ET AL.

It is certified that error appears in the above-identified patent and that said Letters Patent is hereby corrected as shown below:

COLUMN 111

Line 19, "second" should read --seconds--.

COLUMN 112

Line 38, close up right margin.
Line 39, close up left margin.
Line 67, "EXAM-" should read --Exam- --.
Line 68, "PLE 5" should read --ple 5--.

COLUMN 123

Line 16, close up right margin.
Line 17, close up left margin.

COLUMN 133

Line 3, "(4decylphenyl)phenol," should read
--(4-decylphenyl)phenol,--.
Line 50, "$X_4$" should read --$X_{4a}$--.

COLUMN 184

Line 4, "$C_6H_{13}$" should read --$C_4H_9$--.

COLUMN 185

Line 4, "$C_8H_{17}\underset{\underset{O}{\|}}{C}O$" should read --$C_8H_{17}$--.

UNITED STATES PATENT AND TRADEMARK OFFICE
CERTIFICATE OF CORRECTION

PATENT NO. : 5,190,690
DATED : March 2, 1993
INVENTOR(S) : TAKAO TAKIGUCHI, ET AL.

It is certified that error appears in the above-identified patent and that said Letters Patent is hereby corrected as shown below:

COLUMN 185

Line 34, "$C_6H_{13}\underset{\underset{O}{\|}}{C}O$" should read --$C_8H_{17}$--.

COLUMN 213

Line 12, "$C_{10}H_{21}$" should read --$C_{11}H_{23}$--.

COLUMN 221

Line 58, "$C_7H_{15}\underset{\underset{O}{\|}}{O}C$" should read --$C_7H_{15}\underset{\underset{O}{\|}}{C}$--.

COLUMN 223

Line 55, " $\underset{C_2H_6\overset{*}{C}HCH_2}{\overset{CH_3}{|}}$ " should read -- $\underset{C_2H_5\overset{*}{C}HCH_2}{\overset{CH_3}{|}}$ --.

Signed and Sealed this

Third Day of May, 1994

Attest:

BRUCE LEHMAN

Attesting Officer

Commissioner of Patents and Trademarks